(12) United States Patent
Stewart et al.

(10) Patent No.: US 7,587,284 B2
(45) Date of Patent: Sep. 8, 2009

(54) GENE SYNTHESIS SOFTWARE

(75) Inventors: Lansing J. Stewart, Bainbridge Island, WA (US); Alex Burgin, Kingston, WA (US); John W. Walchli, Seattle, WA (US); Kathryn Hjerrild, Bainbridge Island, WA (US)

(73) Assignee: deCODE biostructures, Inc., Bainbridge Island, WA (US)

( * ) Notice: Subject to any disclaimer, the term of this patent is extended or adjusted under 35 U.S.C. 154(b) by 0 days.

(21) Appl. No.: 11/338,861

(22) Filed: Jan. 24, 2006

(65) Prior Publication Data

US 2006/0235626 A1     Oct. 19, 2006

Related U.S. Application Data

(60) Provisional application No. 60/646,660, filed on Jan. 24, 2005.

(51) Int. Cl.
*G01N 33/50* (2006.01)
(52) U.S. Cl. ........................................................ 702/20
(58) Field of Classification Search ....................... None
See application file for complete search history.

(56) References Cited

U.S. PATENT DOCUMENTS

2004/0166567 A1*   8/2004   Santi et al. .................... 435/76

OTHER PUBLICATIONS

Hoover et al. DNAWorks: an automated method for designing oligonucleotides for PCR-based gene synthesis, Nucleic acids Research, vol. 30, No. 10, e43, 2002 [7pages].*
GCG manual, GCG Version 10.3 manual Accelrys, Inc., [retrieved Aug. 31, 2006 from helix.nih.gov/docs/gcg], published 2002.*
Silent mutation, Encyclopedia of Molecular Biology, John Wiley & Sons, Inc., 1999, [available online Jan. 15, 2002, accessed Aug. 31, 2006].*
Hoover (Guide to DNA works, vers. 2-2.4, Jan. 4, 2004, mc1.ncifcrf. gov/dnaworks/dnaworks2_help.html, accessed on Monday Jan. 22, 2007, [11 pages]).*
Seligmann et al (DNA and Cell Biology, vol. 23, No. 10, p. 701-705, 2004).*
Rouillard et al (Nucleic Acids Research, vol. 32, p. W176-W180, 2004).*
Baranov et al., Nucleic Acids Research, vol. 29, No. 1, p. 264-267, 2001.*
Farabaugh, Annual Rev. of Genetics, vol. 30, p. 507-28, 1996.*
Presnell, S.R., and S.A. Benner, "The Design of Synthetic Genes," *Nucleic Acids Research* 16(5):1693-1702, 1988.
Raghava, G.P.S, and G. Sahni, "GMAP: A Multi-Purpose Computer Program to Aid Synthetic Gene Design, Cassette Mutagenesis and the Introduction of Potential Restriction Sites Into DNA Sequences," *BioTechniques* 16(6):1116-1120, 1994.

(Continued)

*Primary Examiner*—Marjorie Moran
*Assistant Examiner*—Karlheinz R Skowronek
(74) *Attorney, Agent, or Firm*—Christensen O'Connor Johnson Kindness PLLC

(57) ABSTRACT

Pieces of software and databases are used to facilitate the design and synthesis of genes. The synthesis techniques allow identification, quantification, transcription, translation, and manipulation of portions of the gene sequence represented as 0's and 1's in a computing system. These pieces of software and databases compile constraint information provided by a user to create synthetic genes to express proteins lacking disordered or variable regions and containing surface mutations that promote solubility and/or crystallization. Regions of the gene sequence that do not form stable structures can be removed and replaced by a short biological linker to improve crystallization of proteins.

8 Claims, 50 Drawing Sheets

OTHER PUBLICATIONS

Shankarappa, B., et al., "SILMUT: A Computer Program for the Identification of Regions Suitable for Silent Mutagenesis to Introduce Restriction Enzyme Recognition Sequences," *BioTechniques* 12(6):882-884, Jun. 1992.

Turchin, A., and J.F. Lawler, Jr., "The Primer Generator: A Program That Facilitates the Selection of Oligonucleotides for Site-Directed Mutagenesis," *BioTechniques* 26(4):672-676, Apr. 1999.

"Examples of How Gene Composer Software for Computer Aided Synthetic Gene Design Can Silently Introduce or Remove Stop Codons in 2nd and 3rd Reading Frames of a Gene Sequence, While Preserving the Amino Acid Coding of the 1st Reading Frame," Apr. 20, 2007, pp. 1-9, information relating to U.S. Appl. No. 11/338,861 entitled "Gene Synthesis Software."

"Search Results for Jan. 1, 1996-Apr. 21, 2007," Internet Archive Wayback Machine, <http://web.archive.org/web/*/http://mc11.nciferf.gov/dnaworks2_help.html> [retreived Apr. 20, 2007].

\* cited by examiner

Fig.3F. (312) — Stop Codon Introduction

| Location | AA Pair | Exists | Old Sequence | New Sequence |
|---|---|---|---|---|
| 36 | LA | TRUE | TTAGCG | TTAGCG |
| 78 | VG | TRUE | GTAGGT | GTAGGT |
| 180 | LV | TRUE | TTAGTG | TTAGTG |
| 246 | LS | FALSE | TTGTCA | TTAGC |
| 261 | LV | TRUE | TTAGTG | TTAGTG |
| 264 | VT | TRUE | GTAGCG | GTGACC |
| 276 | LS | TRUE | TTAAGC | TTAAGC |
| 282 | LI | TRUE | TTGATT | TTGATT |
| 327 | LV | TRUE | TTAGTG | TTAGTG |
| 369 | LV | TRUE | TTAGTG | TTAGTG |
| 372 | VR | TRUE | GTGAGA | GTGAGA |
| 405 | VS | TRUE | GTGAGC | GTGAGC |
| 501 | VT | TRUE | GTGACG | GTGACG |
| 510 | LA | TRUE | TTAGCG | TTAGCG |
| 516 | LR | FALSE | CTGCGC | TTGAGA |
| 522 | IV | TRUE | ATAGTG | ATAGTG |
| 525 | VS | TRUE | GTGAGC | GTGAGC |
| 564 | LK | TRUE | TTGAAG | TTGAAG |
| 570 | VI | TRUE | GTGATT | GTGATT |
| 573 | IG | FALSE | ATTGGC | ATAGGC |
| 579 | VR | FALSE | GTGCGC | GTGAGA |
| 585 | VV | FALSE | GTCGTG | GTAGTG |
| 639 | LI | TRUE | CTGATT | CTGATT |

Fig.3G. (314) — Stop Codon Introduction

| Location | AA Pair | Exists | Old Sequence | New Sequence |
|---|---|---|---|---|
| 9 | PR | TRUE | CCTAGA | CCTAGA |
| 21 | IS | FALSE | ATTTCA | ATTAGC |
| 27 | SS | FALSE | TCTTCA | TCTAGC |
| 54 | PS | TRUE | CCTAGC | CCTAGC |
| 90 | SS | FALSE | AGCTCG | TCTAGC |
| 117 | HS | TRUE | CATAGC | CATAGC |
| 126 | TK | FALSE | ACGAAG | ACTAAA |
| 135 | PS | TRUE | CCTAGC | CCTAGC |
| 141 | PR | FALSE | CCTCGA | CCTAGA |
| 159 | AS | FALSE | GCTTCC | GCTAGC |
| 165 | GR | FALSE | GGAAGA | GGTAGA |
| 189 | CS | FALSE | TGTTCA | TGTAGC |
| 198 | PE | FALSE | CCCGAA | CCTGAA |
| 267 | TN | FALSE | ACCAAC | ACTAAC |
| 297 | GS | FALSE | GGCTCG | GGTAGC |
| 303 | CR | FALSE | TGCAGA | TGTAGA |
| 309 | SS | FALSE | TCATCA | TCTAGC |
| 339 | GK | TRUE | GGTAAA | GGTAAA |
| 354 | GR | FALSE | GGCCGC | GGTAGA |
| 360 | PR | FALSE | CCTCGT | CCTAGA |
| 363 | RN | TRUE | CGTAAC | CGTAAC |
| 378 | GE | TRUE | GGTGAA | GGTGAA |
| 384 | GR | FALSE | GGTCGC | GGTAGA |

Fig.3H.

Shine-Dalgarno Locations — 316

| Location | Removable | Old Sequence | New Sequence |
|---|---|---|---|
| 588 | FALSE | GTGGAGAAGAAGCAATGGATTAAGATG | GTGGAGAAGAAGCAATGGATTAAGATG |
| 591 | FALSE | GAGAAGAAGCAATGGATTAAGATG | GAGAAGAAGCAATGGATTAAGATG |
| 594 | TRUE | AAGAAGCAATGGATTAAGATG | AAAAAACAATGGATTAAGATG |
| 597 | FALSE | AAGCAATGGATTAAGATG | AAACAATGGATTAAGATG |
| 603 | FALSE | TGGATTAAGATG | TGGATTAAGATG |
| 675 | FALSE | CAGGAGAACGGCATG | CAGGAGAACGGCATG |
| 675 | TRUE | CAGGAGAACGGCATG | CAGGAGAACGGCATG |
| 675 | FALSE | CAGGAGAACGGCATG | CAGGAGAACGGCATG |
| 687 | TRUE | ATGGAAGTGACGACACCCATG | ATGGAAGTGACGACACCCATG |
| 696 | TRUE | ACGACACCCATG | ACCACCCATG |
| 726 | TRUE | AGAAGCTTGCCTCAACATATG | CGCAGCTTGCCTCAACATATG |
| 891 | TRUE | ACGAATGCTATCAACCTGTGATG | ACCGAATGCTATCAACCTGTGATG |
| 972 | TRUE | ACGAGAGCACGCTTAATG | ACGGCGCACGCTTAATG |
| 975 | TRUE | AGAGCACGCTTAATG | CGCGCGCGCTTAATG |

Fig.3I.

Shine-Dalgarno Locations — 318

| Location | Removable | Old Sequence | New Sequence |
|---|---|---|---|
| 27 | TRUE | GATGCC | GACGCC |
| 27 | TRUE | GATGCC | GACGCC |
| 27 | TRUE | GATGCC | GACGCC |
| 27 | TRUE | GATGCC | GACGCC |
| 27 | TRUE | GATGCC | GACGCC |
| 492 | TRUE | TATGCG | TACGCG |

GENE SYNTHESIS SOFTWARE

CROSS-REFERENCE TO RELATED APPLICATION

This application claims the benefit of U.S. Provisional Application No. 60/646,660, filed Jan. 24, 2005, which is incorporated herein by reference.

FIELD OF THE INVENTION

The present invention relates generally to software, and more particularly, to composing gene sequences, such as amino acid sequences and nucleic acid sequences, via pieces of software.

BACKGROUND

One of the less appreciated features of whole gene synthesis is the ability to accurately design synthetic gene sequences with desired features. As the bioinformatics knowledge base grows, there is an increasing demand for synthetic genes that incorporate multiple overlapping information content elements. Yet, the human mind is unable to hold sufficient immediate genetic information to aid in its decision making process, and therefore, there is a need for an ability to observe bioinformatics constraints in the synthesis of genes. Those companies that can provide the tools to design synthetic gene sequences will be equally important in the whole gene synthesis marketplace. The demand for synthetic genes is likely to be closely correlated with the availability of increasingly sophisticated software tools that can distill massive amounts of biological information and multiple layers of genetic coding information into a single nucleotide sequence or group of sequences. Biotechnology is a maturing industry, and the standardization of design and engineering methods such as whole gene synthesis will likely supplant many of the more traditional hands on multi-step molecular biology procedures and kits.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In accordance with this invention, a system, method, and computer-readable medium for synthesizing gene sequences is provided. The system form of the invention includes a system that comprises a gene specifier for specifying an amino acid sequence and a number of parameters including an expression system, a threshold to exclude rare codons, salt concentration, molar concentration, and target melting temperature. The system further comprises a back translator for translating the amino acid sequence into a nucleic acid sequence whose codons exclude rare codons and include codons with participating probabilities to allow them to appear in the nucleic acid sequence. The system also comprises an oligonucleotide producer that processes the nucleic acid sequence to produce sets of oligonucleotides whose melting temperature is within proximity to the target melting temperature for synthesizing a gene sequence representing the nucleic acid sequence.

In accordance with further aspects of this invention, a method form of the invention includes a computer-implemented method for synthesizing gene sequences. The method comprises back translating an amino acid sequence to a nucleic acid sequence and introducing stop codons into the nucleic acid sequence via silent mutations.

In accordance with further aspects of this invention, a computer-readable medium form of the invention includes a computer-readable medium having instructions stored thereon to implement a method for synthesizing gene sequences. The computer-readable medium comprises specifying an amino acid sequence and a number of parameters including an expression system, a threshold to exclude rare codons, salt concentration, molar concentration, and target melting temperature. The computer-readable medium further comprises translating the amino acid sequence into a nucleic acid sequence whose codons exclude rare codons and include codons with participating probabilities to allow them to appear in the nucleic acid sequence. The computer-readable medium also comprises processing the nucleic acid sequence to produce sets of oligonucleotides whose melting temperature is within proximity to the target melting temperature for synthesizing a gene sequence representing the nucleic acid sequence.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 2A is a pictorial diagram illustrating an exemplary user interface for specifying a project in accordance with one embodiment of the present invention;

FIGS. 2B-2D are pictorial diagrams illustrating a wizard for a user to specify a gene sequence to be synthesized;

FIG. 2G is a pictorial diagram illustrating an exemplary user interface for displaying a gene sequence;

FIG. 2H is a pictorial diagram illustrating an exemplary user interface showing modifications to a gene sequence;

FIG. 3A is a pictorial diagram illustrating an exemplary user interface for back translating a gene sequence;

FIGS. 3C-3D are pictorial diagrams illustrating exemplary user interfaces for locating and removing sequence repeats;

FIGS. 3E-3G are pictorial diagrams illustrating exemplary user interfaces for finding and introducing stop codons into a gene sequence;

FIGS. 3H-3J are pictorial diagrams illustrating exemplary user interfaces for locating and removing Shine-Dalgarno locations in a gene sequence;

FIGS. 3K-3N are pictorial diagrams illustrating exemplary user interfaces for locating restriction sites, introducing or removing restriction sites, and adding restriction sites, Protease cleavage sites, and epitope tags;

FIG. 4A is a pictorial diagram illustrating an exemplary user interface for creating oligonucleotides for synthesizing a gene sequence;

FIG. 4B is a pictorial diagram illustrating an exemplary user interface for improving the melting temperature of one or more oligonucleotides;

FIG. 4C is a pictorial diagram illustrating an exemplary user interface for designing primers;

DETAILED DESCRIPTION

Various embodiments of the present invention include pieces of software and databases that facilitate the design and synthesis of genes. These pieces of software and databases are used together with molecular biology techniques to assemble open reading frames from synthetic oligonucleotides. A user can optimize the open reading frame for desirable codon usage, minimize mRNA secondary structures, eliminate or introduce restriction sites, eliminate or introduce regulatory regions, and so on. Genes can be designed for optimal protein expression for the organism (expression system) of choice. In other words, various embodiments of the present invention receive from a user or deduct biological constraints in synthesizing gene sequences without the need for the user to remember the constraints to follow in designing and synthesizing gene sequences. The synthesis techniques of various embodiments of the present invention allow identification, quantification, transcription, translation, and manipulation of portions of the gene sequence represented as 0's and 1's in a computing system. Various embodiments of the present invention enable researchers to distill a growing body of genetic information into a highly optimized gene sequences that are designed to contain desired features, and/or lacking undesired features. For example, various embodiments of the present invention may compile constraint information provided by a user to create synthetic genes to express proteins lacking disordered or variable regions and containing surface mutations that promote solubility and/or crystallization. As another example, in regions of the gene sequence that do not form stable structures can be removed and replaced by a short biological linker to improve crystallization of proteins.

Figure 1A:
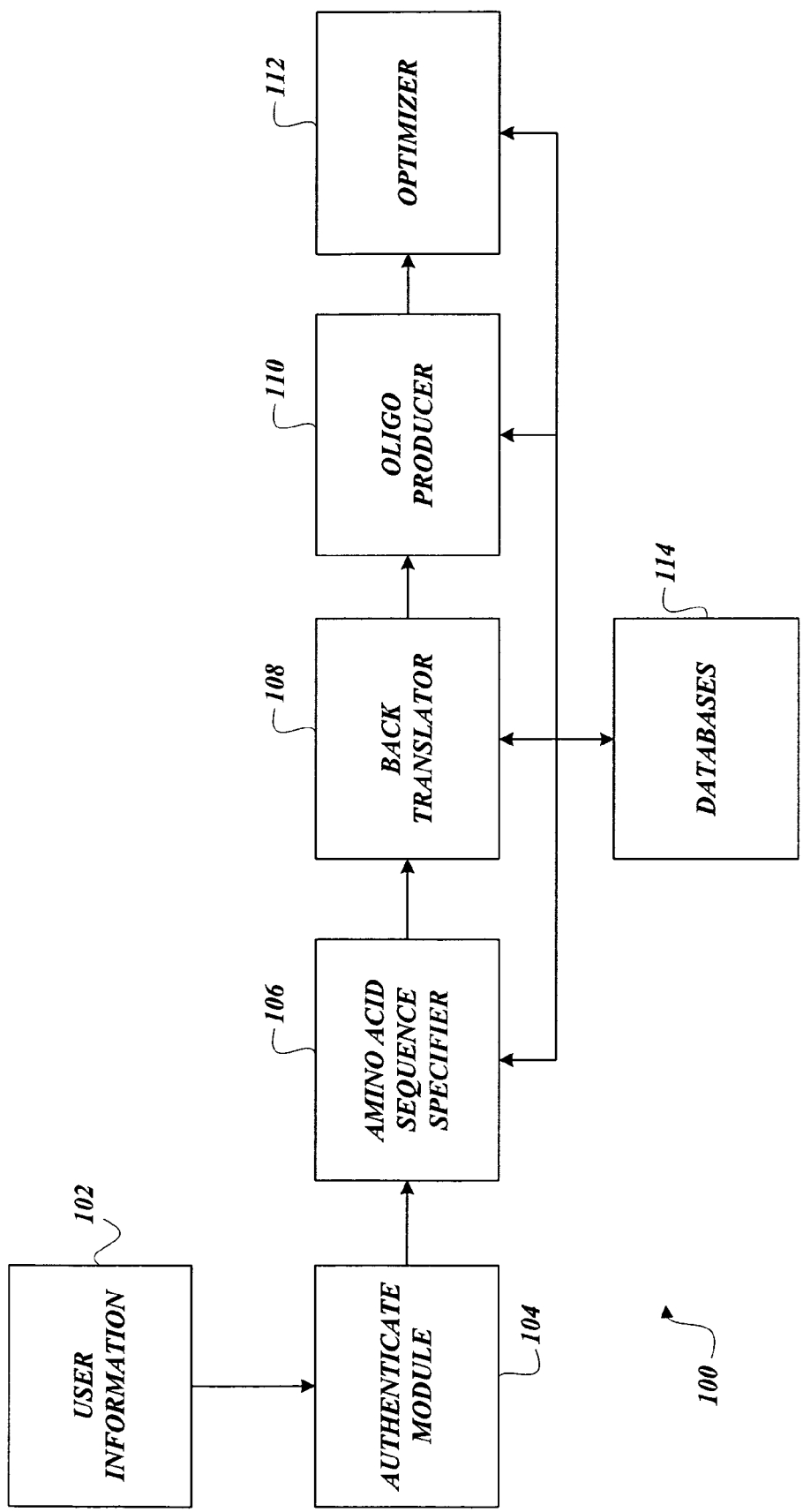
FIG. 1A is a block diagram illustrating exemplary pieces of software for synthesizing gene sequences.

FIG. 1A illustrates a whole gene synthesis system 100. The system 100 can be used to convert a protein sequence to an expression-optimized gene sequence and a gene sequence into a set of oligonucleotides that can be used for the assembly of the desired synthetic gene. Pieces of user information 102, such as a user's name and password, are provided to an authenticate module 104 of the system 100. The authenticate module 104 validates a user's logon information. In other words, a user's name and password are compared against an authorized list and if the system 100 detects a match, access is granted to the user. When access has been granted, the user may use an amino acid sequence specifier 106 to indicate an amino acid sequence that would be processed by the rest of the system 100 (the amino acid sequence specifier 106 can also receive nucleic acid sequence in some embodiments of the present invention). A back translator 108 takes the amino acid sequence and back translates using one or more optimization techniques, such as codon optimization or delta g optimization. The back translator 108 can reverse-translate an amino acid sequence into a nucleic acid sequence by random selection of synonymous codons according to the frequency (participating probability) with which they are found in the intended host organism. Various embodiments of the present invention create expression optimized genes with improved codon bias for production of recombinant proteins in heterologous systems and other systems. The results of the back translator 108 include a nucleic acid sequence that can be synthesized using oligonucleotides. An oligonucleotide producer 110 produces the specifications for these oligonucleotides. Further optimizations can be obtained by using an optimizer 112. Many suitable optimizations can be accomplished, such as melting temperature optimization and so on. The system 100 also includes databases 114 that trace the pedigree of a gene sequence including its modifications. The system 100 can be used in combination with gene shuffling and in vitro evolution technologies to re-engineer the genetic translation machinery to produce desired polymeric materials, as an example.

Figure 1B:
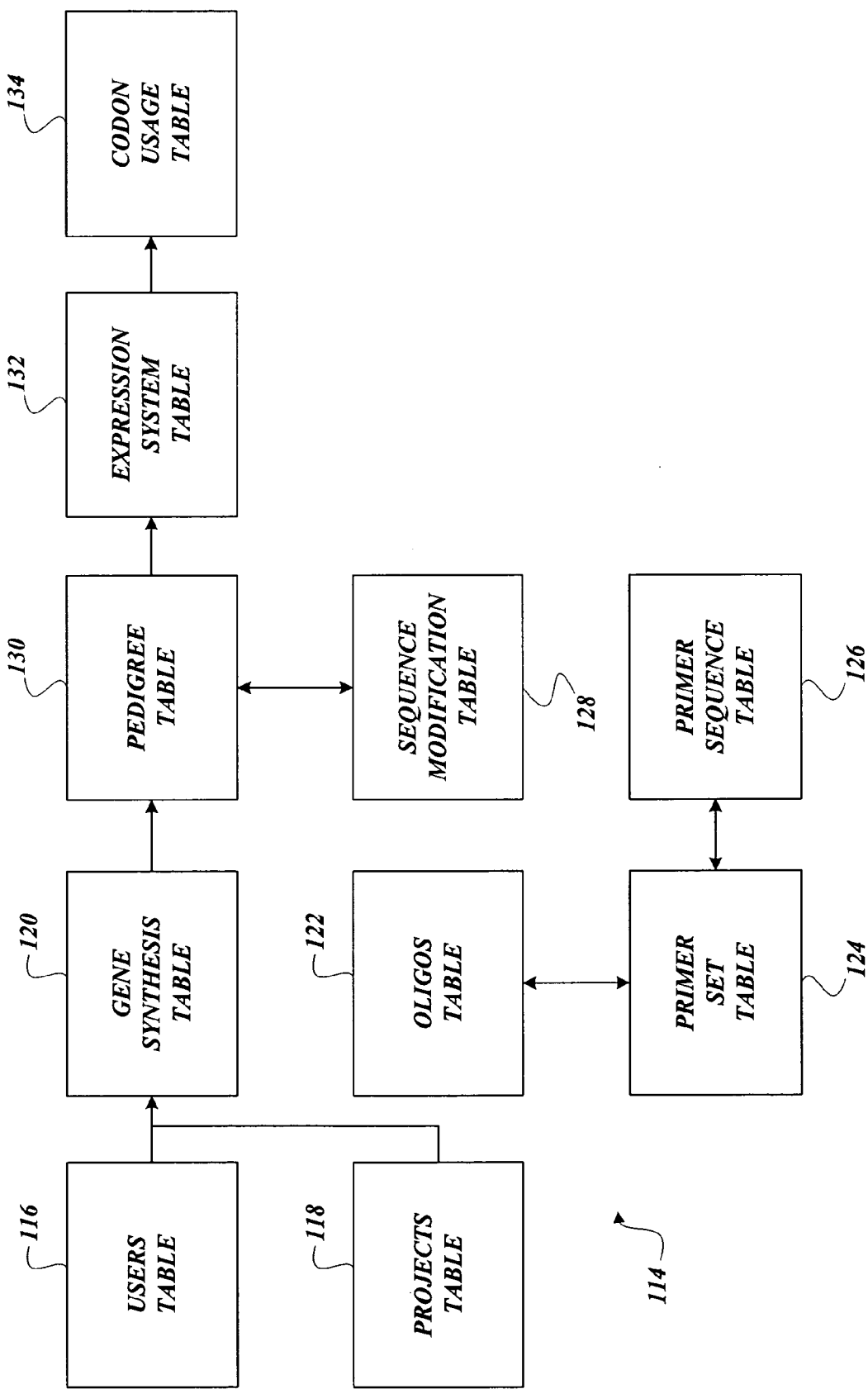
FIG. 1B is a data structure diagram illustrating tables in a database forming a facility to trace users, projects, gene sequences, and their modifications.

FIG. 1B illustrates a portion of a collection of database tables 116-134. Each database table 116-134 is basically a file composed of records, each containing fields together with a set of operations for searching, sorting, recombining, and performing other database functions. Each record of database tables 116-134 has a data structure, which is characterized by rows and columns with data occupying or potentially occupying each cell formed by a row-column intersection. Information regarding amino acid sequences, nucleic acid sequences, oligonucleotides, constraints on these sequences, parameters of these sequences, and modifications made to these sequences, therefore have a data structure for describing such information. The databases 114 include a users table 116; a projects table 118; a gene synthesis table 120; an oligos table 122; a primer set table 124; a primer sequence table 126; a sequence modification table 128; a pedigree table 130; an expression system table 132; and a codon user table 134. Each table 116-134 has a number of fields. Information regarding gene sequences, users, and projects connected with these gene sequences is stored in these fields, which form the columns of each table with information occupying the rows. These tables 116-134 facilitate searches by using data in specified columns in one table to find additional data in another table. Information is matched from a field in one table with information in a corresponding field of another table to produce results for queries that combine requested data from both tables. For example, table 120 contains an identification field for a particular gene sequence and table 130 also contains a number of fields including an identification field. The databases 114 can match the identification fields in the two tables 120, 130 to find information (e.g., all children genetic sequences of a particular parent amino acid sequence). In other words, the databases 114 can match values in two tables to relate information in one to information in the other so as to expose interrelationships among seemingly disparate pieces of information.

The users table 116 contains information pertaining to users of the system 100. Pieces of information stored by the users table 116 include logon information, such as users' names and passwords. The projects table 118 stores information connected with projects, such as a project name and a project description. The gene synthesis table 120 stores both amino acid sequences as well as nucleic acid sequences connected with a particular project. These three tables 116-120 allow a history to be created tracing users connected with a project as well as genetic sequences involved in that particular project. The pedigree table 130 stores parent-child relationships so as to allow the tracing of which nucleic acid sequence came from which amino acid sequence and subsequent modified nucleic acid sequences from an original nucleic acid sequence. The sequence modification table 128 stores various changes made to a nucleic acid sequence, such as the introduction of stop codons and so on. The expression system table 132 contains biological systems that provide certain constraints over how a particular gene can be mutated or synthesized. The codon user table 134 stores a collection of codons with associated participating probabilities when used to code a particular genetic sequence for a specific biological system. The oligos table 122 contains sets of oligonucleotides for synthesizing a nucleic acid sequence. The primer set table 124 specifies pools of oligonucleotides and the primer sequence table 126 contains the actual genetic sequences in each pool.

Figures 2A, 2B:
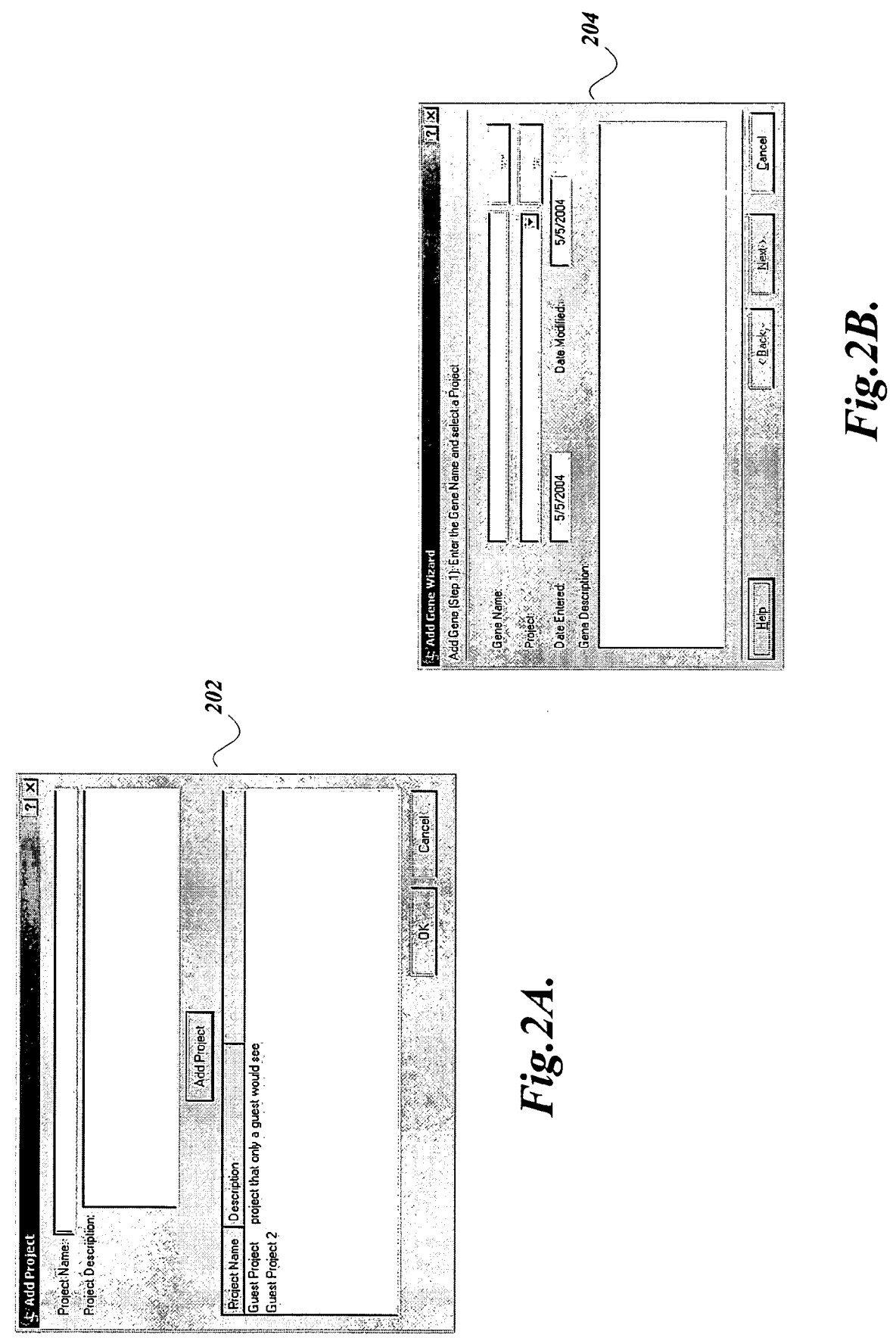

FIG. 2A illustrates a user interface that is invoked by a user to add a new project to the system 100. A text box titled Project Name allows the user to enter the name of the project. Another text box titled Project Description allows the user to textually describe the project to be commenced. When the user is satisfied with the project name and the project description, he can push a button titled Add Project to create a new project in the system 100. A list appears in the lower half of the user interface 202 showing existing projects as well as newly added projects. If the user is satisfied with the added project, he clicks on an OK button to exit from the user interface 202. Otherwise, if he wishes to exit without making any changes, the user selects a Cancel button and the user interface 202 will disappear from view. Preferably, the project name as entered into the text box titled Project Name is unique from other project names in the system 100. A user that is not an administrator is likely to be able to see only certain project names and descriptions appropriate to the level of access available to that user. The administrator will be able to see all projects in the system 100. The text connected with the text box titled Project Description is optional and the user need not enter any.

FIG. 2B illustrates a user interface 204 for adding a genetic sequence to a particular project specified by the user interface 202 (discussed previously). A text box titled Gene Name allows the user to textually enter the name of the gene to be composed. To the right of the text box is a button, which when pressed by the user, allows the user to locate the name of a particular gene sequence. Underneath the text box titled Gene Name is another text box titled Project, in which the user can specify a project from a list (which is provided when he presses a button marked by a downward pointing arrow). To the right of the text box title Project is a button, which when pressed by the user, allows the user to invoke the user interface 202 to create new projects. The user interface 204 also includes boxes that specified the date on which the gene sequence was entered into the system 100 as well as the date on which the gene sequence was modified. In the lower half of the user interface 204 is a text box titled Gene Description that contains an area in which the user may textually describe the gene sequence to be created. Four buttons appear at the bottom of the user interface 204. A Help button, when selected, brings a help utility to aid the user to better understand the purpose and usage information connected with the user interface 204. A Back button and a Next button allow the user to navigate between various pages of a wizard with which the user interface 204 is a part. A cancel button allows the user to exit from the composition of the gene sequence all together. The user interface 204 can be used to add either an amino acid (protein) sequence or nucleic acid (gene) sequence. If the user adds a nucleic acid sequence, a corresponding amino acid sequence will be created using the first open reading frame. Preferably, the gene name that is entered by the text box titled Gene Name should be unique. Input into the text box titled Gene Description is optional. When a gene name and a project have been selected, the next button at the bottom of the user interface 204 will become visible for the user to select to move to the next page of the wizard.

Figure 2D:
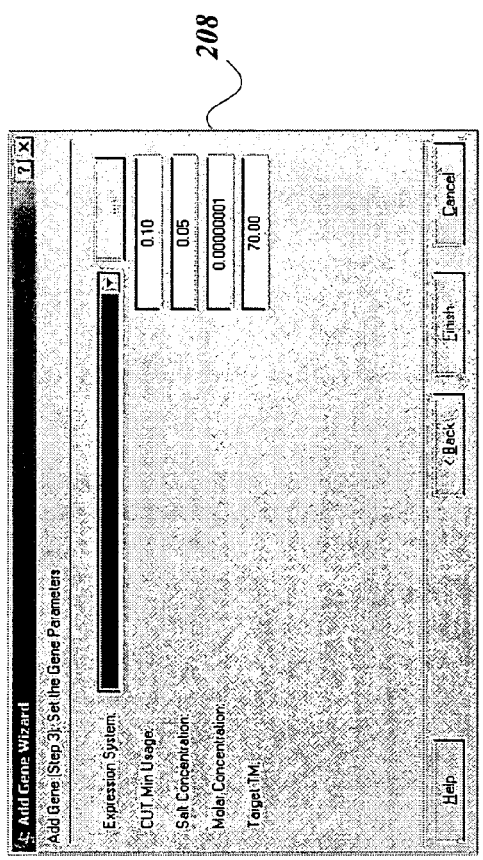
Figure 2C:
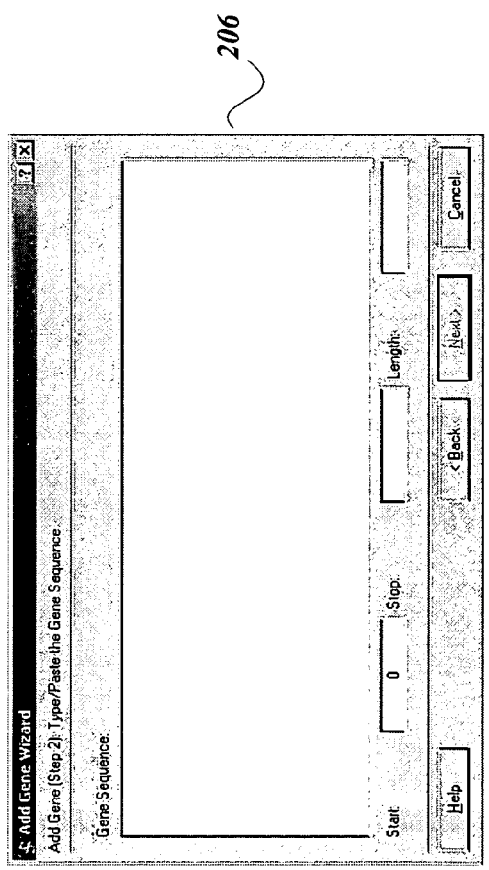

FIG. 2C illustrates a user interface 206 that contains a large text box titled Gene Sequence in which the user may paste or type an amino acid sequence for synthesis by the system 100. Three text boxes appear below the text box titled Gene Sequence for specifying the start position of the gene sequence, the stop position of the gene sequence, and the length of the gene sequence. Like the user interface 204, four buttons (Help, Back, Next, and Cancel) appear at the bottom of the user interface 206. The text box titled Gene Sequence allows either an amino acid sequence or a nucleic acid sequence to be entered into it. The start, stop and length text boxes will automatically be filled as the sequence is entered. When the amino acid sequence or the nucleic acid sequence has been entered, the Next button at the bottom of user interface 206 becomes visible for the user to select and move to the next page of the wizard.

FIG. 2D illustrates a user interface 208, which is another page of the wizard containing user interfaces 204, 206 (previously discussed). A drop down text box titled Expression System allows the user to specify the expression system for which gene synthesis is to take place. To the right of the text box titled Expression System is a button, which when selected by the user, brings the user to a screen that the user can browse to find a suitable expression system. Underneath the text box expression system is another text box titled Cut Minimum Usage, which allows the user to specify a threshold below which codons would be rejected as being rare if their participating probability does not equal or exceed a value placed in the text box titled Cut Minimum Usage. The user may specify a salt concentration in another text box titled Salt Concentration. A text box titled Molar Concentration can be used by the user to specify the molar concentration. Another text box titled Target TM allows the user to specify the desired melting temperature for the synthesized gene sequence. Like user interfaces 204, 206, four buttons appear at the bottom of user interface 208 and these include the Help button, the Back button, and the Cancel button. The fourth button titled Finish allows the user to exit from the wizard. The user interface 208 is the last page of the wizard and it allows the gene parameters to be changed by the user. The drop down text box titled Expression System is connected with the Expression System table 132 of the databases 114. The specified Expression System allows for codon optimization in back translation of an amino acid sequence or a nucleic acid sequence and it is also used to determine suitable triplets for silent mutation when the amino acid sequence or the nucleic acid sequence is modified. The value entered at the text box titled Cut Minimum Usage is preferably a decimal value between 0 and 1. This is a threshold for codon triplets that would not be considered for codon optimization and modifying a particular amino acid sequence or nucleic acid sequence. The value of the Cut Minimum Usage determines how well an amino acid sequence or a nucleic acid sequence will express in a particular organism or expression system. Setting the usage too low may allow rare codons to be used in the amino acid sequence or nucleic acid sequence. Setting the usage threshold too high may exclude too many codons and prevent back translation. The salt concentration value specified at the text box titled Salt Concentration is the value of the salt molarity (Kcal/Mol) that is used for calculating the melting temperature of oligonucleotides. The molar concentration value specifies at the text box titled Molar Concentration is the value of the molar concentration of the solution in which the amino acid sequence or the nucleic acid sequence is contained. This is also used for calculating melting temperature of oligonucleotides, and the target melting temperature is the minimum melting temperature at which the user would like the oligonucleotides to anneal. This value is also used in methods for improving melting temperature, reducing variation of the melting temperature, or raising melting temperature.

Figure 2F:
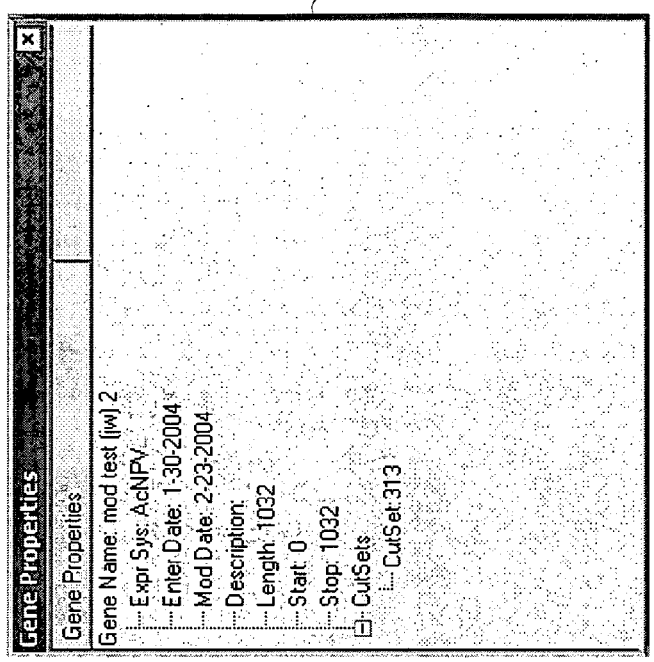
FIG. 2F is a pictorial diagram illustrating an exemplary user interface for presenting properties of a gene sequence.
Figure 2E:
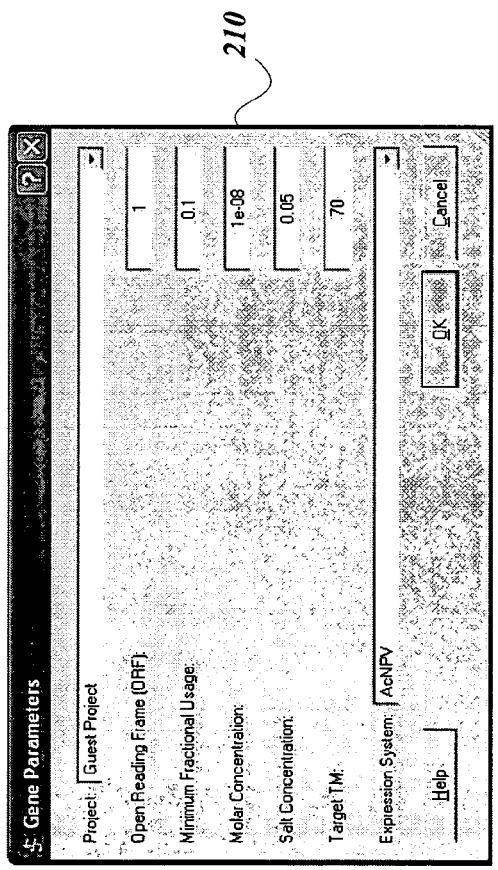
FIG. 2E is a pictorial diagram illustrating an exemplary user interface for specifying parameters of a gene sequence.

FIG. 2E illustrates a user interface 210, which contains similar user interface elements described in connection with the user interface 208 (FIG. 2D). The user interface 210 allows the user to specify different projects, different cut minimum usage (minimum fractional usage), molar concentration, salt concentration, target melting temperature, and expression system. The user interface 210 also allows the user to specify the open reading frame, which is the frame the nucleic acid sequence is to be translated by the system 100. The first open reading frame is the start of the sequence, but other frames can be specified here (1, 2, or 3). A Help button at the bottom of the user interface 210 invokes a help utility to aid the user in using the user interface 210. If the user is satisfied with the parameters connected with the gene sequence, an OK button can be selected to exit from the user interface 210. Otherwise, a Cancel button is available for the user to select to exit from the user interface 210 without making changes.

FIG. 2F illustrates a gene properties user interface 212, which is part of a gene composer window. The user interface 212 shows the name of the gene sequence being worked on, the expression system (or organism) that is used for the codon usage table, the date the gene sequence was added to the system 100, the date of last modification made to the gene sequence, the description of the gene sequence if any, the length, start, and stop location of the gene, and the cut set (sets of oligonucleotides) associated with a gene sequence.

Figure 2G:
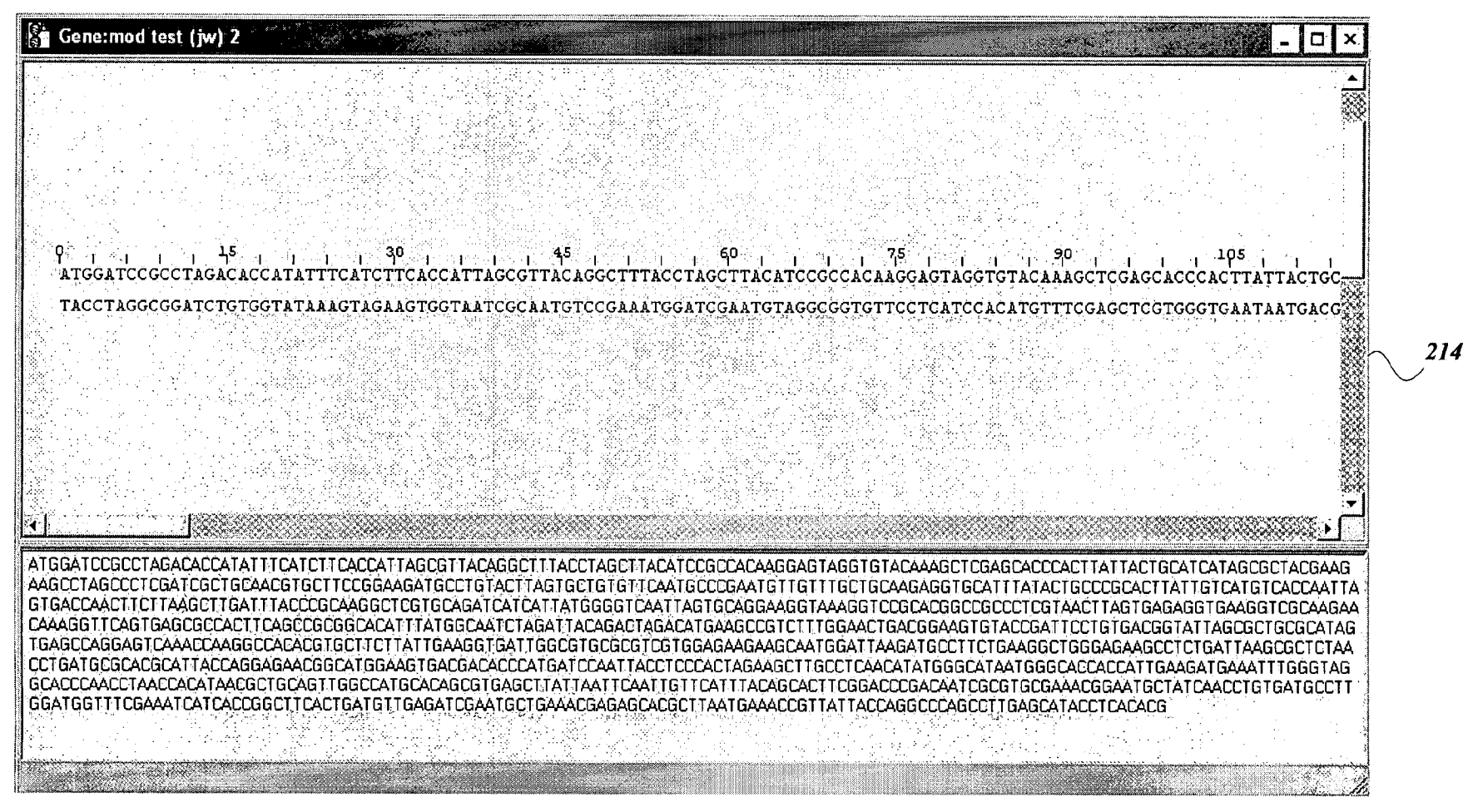

FIG. 2G illustrates a user interface 214, which is a gene window displaying the gene sequence (either amino acid sequence or nucleic acid sequence) with tickers marking the location of each amino acid or nucleic acid in the upper half of the user interface 214. In the lower half of the user interface 214 is a gene sequence that the user may copy portions to the clipboard. The user interface 214 includes scroll bars that allow the user to see portions of the gene sequence that are hidden from view.

Figures 2H, 3A:
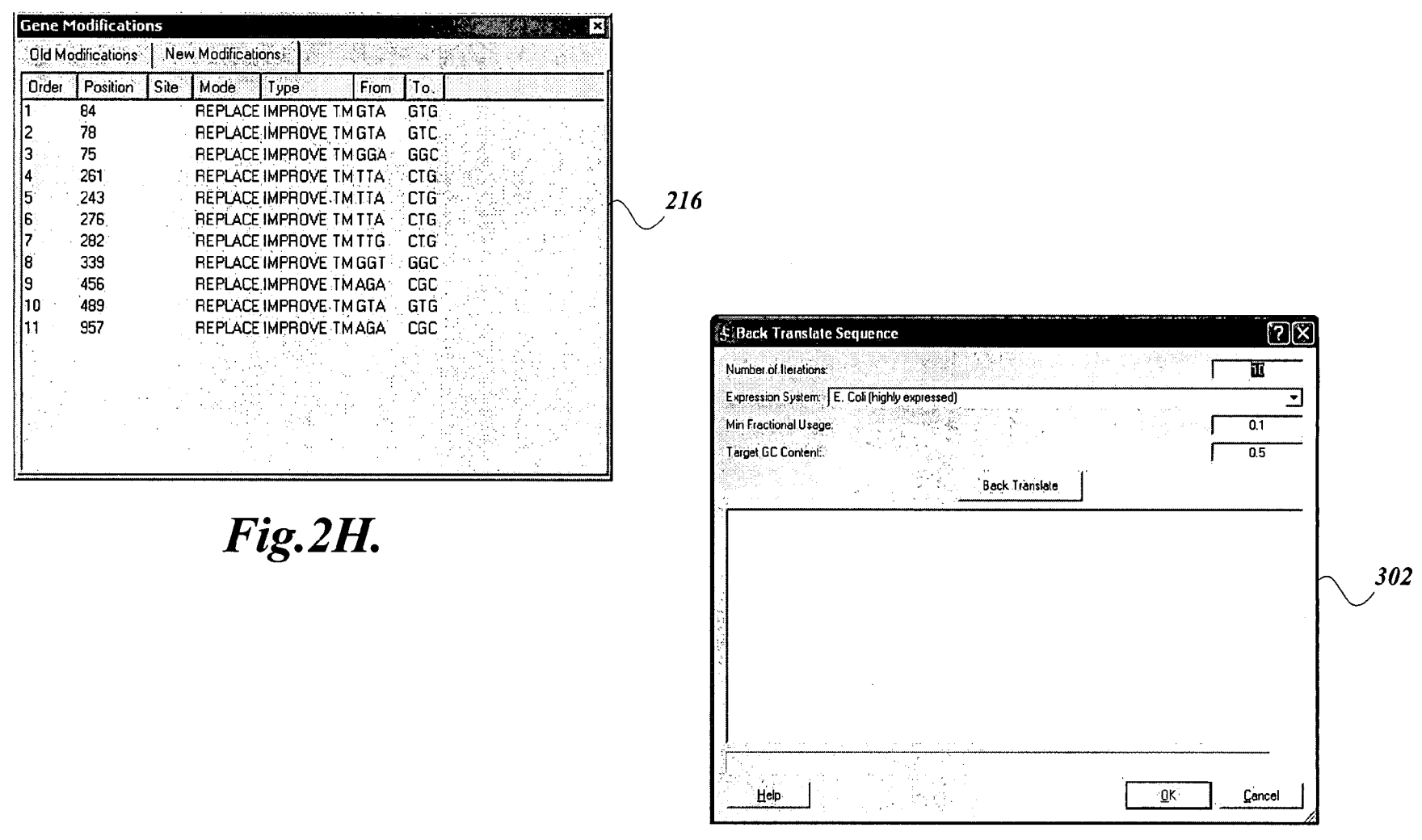

FIG. 2H illustrates a user interface 216 displaying modifications made to a gene sequence. The user interface 216 is part of the gene composer main window. Two tabs are available for selection by the user. The Old Modifications tab shows the modifications made to the gene that are already stored in the databases 114. The Old Modifications tab represents the history of modifications that have been made to the gene sequence in the past. The New Modifications tab shows the modifications made to the gene sequence after the gene sequence has been opened by the user but prior to saving it to the databases 114. There are seven columns underneath each tab. An order column shows progressively the modifications made to the gene sequence over time. The position column shows the location at which the gene sequence was modified. The site column shows the name of the restriction site on the gene sequence. The mode column displays the manner in which the modification was made. The type column shows the specific modification, such as improving melting temperature. The from and to columns show the specific genes from one gene subsequence to another gene subsequence.

FIG. 3A illustrates a user interface 302 for back translating gene sequences. The user interface 302 back translates an amino acid sequence for the current gene sequence using codon optimization. The previously specified expression system and the minimum fractional usage are the parameters used to generate the codon optimized nucleic acid sequence at the end of the process. The user interface 302 includes a text box titled Number of Iterations. This text box allows the user to determine how many times the back translation process will run. A pull down text box titled Expression System allows the user to specify the expression system within which the back translation will be executed. This text box preferably will be automatically filled according to previously specified gene parameters. The minimum fractional usage will also be automatically entered in accordance with previously specified gene parameters for controlling codons that are to participate in the back translation. A text box titled Target GC Content allows the user to specify a value for the back translating process to produce a nucleic acid sequence with GC content that is closer to the targeted value specified in the text box titled Target GC Content. A button titled Back Translate, when selected by the user, will commence the method to back translate the amino acid sequence to a final codon optimized nucleic acid sequence. This nucleic acid sequence is displayed in a text box below the button titled Back Translate. If the user is satisfied with the result of the back translation, an OK button is available for him to select to exit from the user interface 302. Otherwise, he selects a Cancel button to exit from the user interface 302 without any back translation to the gene sequence.

Figure 3B:
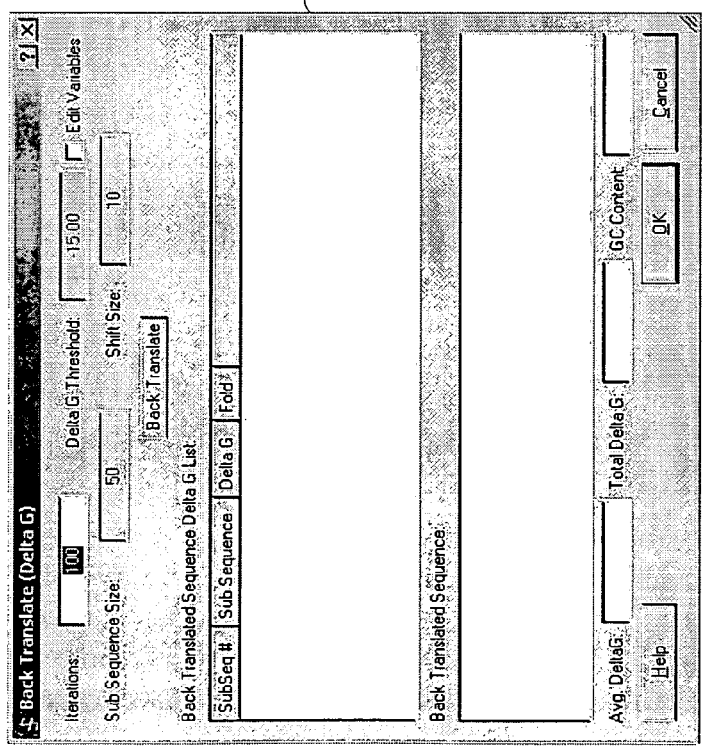
FIG. 3B is a pictorial diagram illustrating an exemplary user interface for back translating a gene sequence.

FIG. 3B illustrates a user interface 304 for back translating a gene sequence optimized for delta g (in other words, RNA folding optimized by determining the free energy of a subset of oligonucleotides). The user interface 304 includes a text box titled Iterations, which when entered specify the number of iterations the back translation process will run. A check box titled Edit Variables can be selected by the user to change the delta g threshold, which determines the value at which oligonucleotides' free energy will be acceptable. The more negative the value entered at this text box, the more genetic sequences will be accepted. The closer to zero, the less genetic sequences will be accepted in comparison to the delta g threshold. Two additional text boxes modifiable by the user include a Subsequence Size, which specifies a window size of each oligonucleotide (i.e., how large each oligonucleotide can be). The Shift Size text box is used to determine how far into the sequence the next oligonucleotide will be selected. A Back Translate button located underneath these text boxes can be selected by the user to begin the back translation process. The final nucleic acid sequence is produced after the back translation process is finished (if one exists) and will be displayed in two views in the lower half of the user interface 304. The upper view displays a list of oligonucleotides in four columns. The first column displays the number of the subsequence, the second column shows the genetic subsequence, the third column shows the free energy connected with the subsequence, and the fourth column shows the fold structure of the genetic subsequence. The lower view displays the nucleic acid sequence. At the bottom of the lower view are three text boxes showing the average delta g, the total delta g, and the GC content of the back translated nucleic acid sequence. If the user is satisfied with the back translation, an OK button is available for the user to select to exit from the user interface 304. Otherwise, a Cancel button is available for selection to exit from the user interface 304 without changes.

Figure 3C:
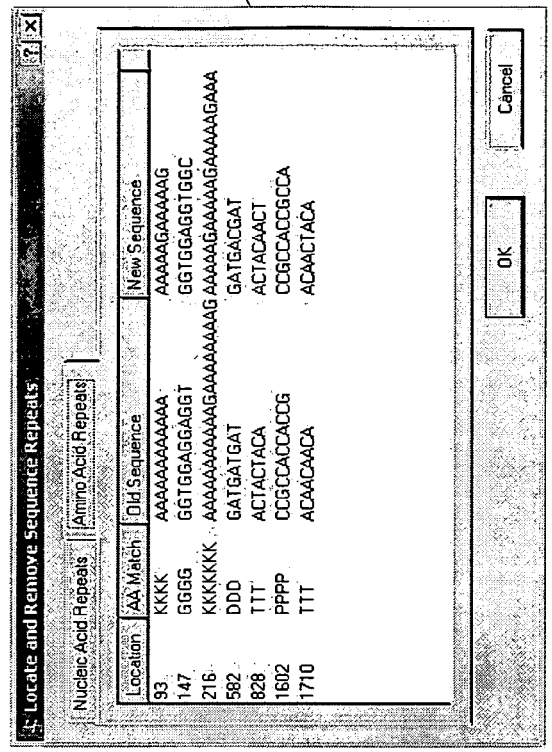

FIG. 3C illustrates a user interface 306 for finding and removing sequence repeats. Two tabs are provided to display the repeats in the genetic sequence. The user interface 306 presents amino acid repeats in the genetic sequence. Four columns are provided. A Location column specifies the location in the gene sequence where the repeat may be found. A column titled AA Match displays the pattern of the amino acid subsequence that was found to be repeating. A column titled Old Sequence displays the nucleic acid sequence interpreted from the amino acid. Another column titled New Sequence displays the result of silent mutations to remove the sequence repeats. The user may select one or more items from the list to indicate those repeats to be removed by silent mutations. An OK button at the bottom of the user interface 306 can be selected by the user to confirm that these selected repeats will be removed from the gene sequence. Otherwise, a Cancel button is also available for selection to exit from the user interface 306 without any changes.

Figures 3D, 3E:
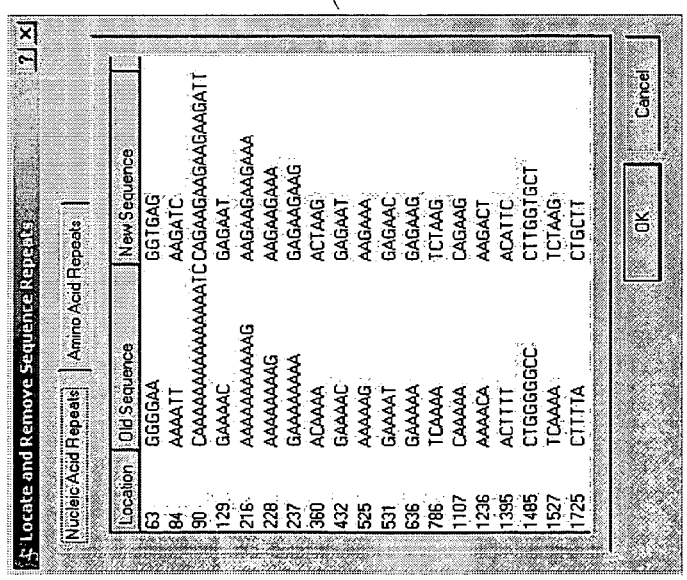

FIG. 3D illustrates a user interface 308 presenting the Nucleic Acid Repeats tab showing repeats in the gene sequence. Three columns are shown on the tab. One column titled Location indicates the position in the gene sequence at which the repeat can be found. Another column titled Old Sequence includes the nucleic acid pattern that was found to be repeating. A third column titled New Sequence indicates proposed silent mutations to remove the repeat pattern of the nucleic acid sequence. The user may select one or more items from the list to indicate to remove the repeats by silent mutations. If the user is satisfied with the selected mutations to remove the repeats, an OK button at the bottom of the user interface 308 can be selected. Otherwise, to exit from the user interface 308 without changes, a Cancel button is available for selection.

FIG. 3F illustrates a user interface 312 for finding and introducing stop codons. The translation machinery is not perfect, and depending on the circumstance it can shift out of the primary reading frame and into either the second (+1) or third (−1) possible reading frame. Once a shift in reading frame occurs, then the translation machinery will end up spending precious time and energy translating defective polypeptides that contain out of frame encoded amino acid sequences at their C-termini. It has been proposed that the presence of hidden stop codons may be an adaptation in species with slippage prone ribosomes. Therefore, if the alternative reading frames are open for long distances, and the translation machinery happens to slip into an alternate reading frame, then it will spend even more time on average translating defective proteins. Based on this concept, various embodiments of the present invention can silently introduce as many hidden stop codons as possible into the alternate reading frames. This serves the purpose of rapidly terminating translation if frame-shifts do occur, so that less of the cell metabolism is wasted on translation of defective proteins.

In the user interface 312, three tabs are presented: Second Frame Stops tab, Third Frame Stops tab, and First Frame Stops (bottom strand). Five columns are shown in the tab titled Second Frame Stops showing whether stop codons are present or not in the gene sequence. The first column titled Location indicates the position at which a stop codon ought to be found or can be found. A second column titled AA Pair indicates an amino acid sequence pair at the location. A third column titled Exists indicates whether (true or false) a stop codon can be found at that particular location in the gene sequence. The fourth column titled Old Sequence shows the nucleic acid sequence at that location in the gene sequence. The last column titled New Sequence displays the nucleic acid sequence as a result of silent mutations to introduce a stop codon at that particular location. At the bottom of the user interface 312 are two buttons, Cancel and OK. The user may select those locations at which the user wishes to introduce a stop codon if one is not already present at that location. By pushing the OK button, the user interface 312 will proceed to introduce stop codons at the selected locations and exit. The user may also select the Cancel button to exit from the user interface 312 without making changes.

FIG. 3G illustrates a user interface 314 showing the tab titled Third Frame Stops. The user interface 314 is another view of the user interface 312 where the tab Third Frame Stops is now displayed. Many of the elements of the user interface 314 are similar to the user interface 312 and they will not be repeated here for brevity purposes. Some similar elements include columns titled Location, AA Pair, Exists, Old Sequence, and New Sequence. The difference is that the found repeats occur in the third frame of the gene sequence whereas the user interface 312 displays stop codons found in the second frame of the gene sequence. Not shown is information connected with the last tab titled First Frame Stops (bottom strand). This tab contains similar information to the user interfaces 312, 314 and they will not be repeated here for brevity purposes. The difference is that the last tab displays information connected with stop codons found in the first frame of the bottom strand of the gene sequence.

Figures 3J, 3K:
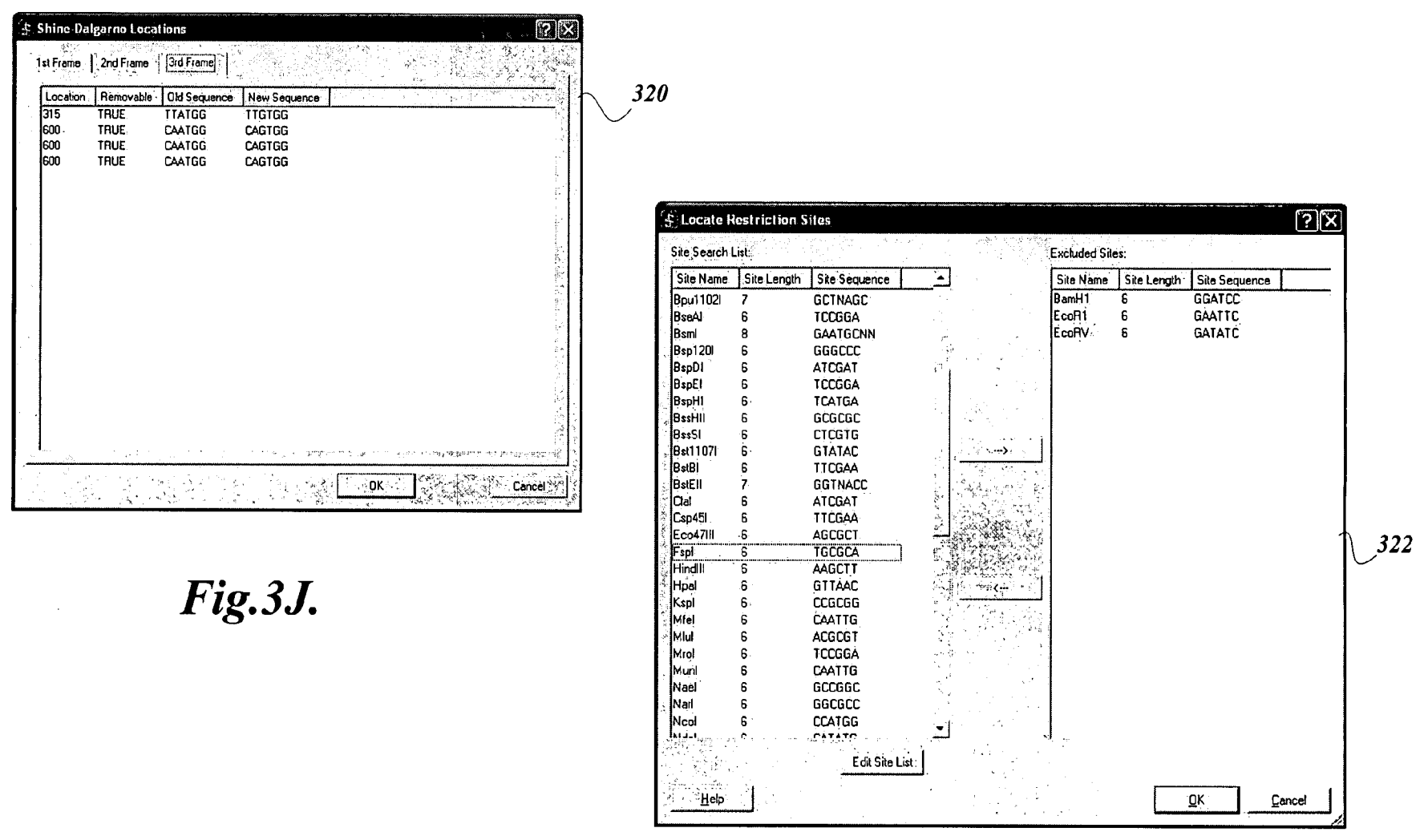

FIGS. 3H-3J illustrate user interfaces 316, 320 for disclosing Shine-Delgarno locations. The user interface 316 displays the first tab titled First Frame. This tab displays four columns. The first column titled Location indicates the position at which a cryptic Shine-Delgarno sequence may be found. The second column titled Removable indicates whether the Shine-Delgarno location can be removed or not. Those that are removable are marked as true and the user may select them for removal. Otherwise, the Shine-Delgarno location is not removable and that column will mark the item as false, indicating that the Shine-Delgarno location cannot be removed. The third column titled Old Sequence displays the nucleic acid subsequence containing the cryptic Shine-Delgarno sequence. The fourth column titled New Sequence displays proposed silent mutations to remove the cryptic Shine-Delgarno sequence. At the bottom of the user interface 316 are two buttons. An OK button can be selected by the user to confirm the removal of various Shine-Delgarno locations. To exit without making changes, the user may select a Cancel button. The user interface 318 is similar to the user interface 316 except that the Shine-Delgarno locations are found in the second frame of the gene sequence. The user interface 320 is similar to the user interfaces 316, 318. The difference is that the user interface 320 displays information in connection with the third frame of the gene sequence where the Shine-Delgarno locations may be found. For the second and the third frames, the system 100 is looking for Methionine in the gene sequence and uses silent mutations to remove the Methionine.

FIG. 3K illustrates a user interface 322 for locating restriction sites. The user interface 322 shows two lists. One list is titled Site Search List and includes three columns. The first column is titled Site Name and displays the names of various restriction sites. The second column is titled Site Length and discloses the length of the restriction site. The third column titled Site Sequence displays the nucleic acid subsequence of the particular restriction site. The second list is titled Excluded Sites and the sites listed under this list will be removed using silent mutations when the system 100 determines if the sites in that list exist in the gene sequence. Two buttons between the list titled Site Search List and the List titled Excluded Sites are located between the two lists. The first button has a symbol showing an arrow pointing to the right that can be selected by the user to move one or more sites from the list titled Site Search List to the list titled Excluded Sites. Those sites that are moved from the list titled Site Search List to the list titled Excluded Sites will not be considered by the system 100 in determining whether restriction sites exist in this gene sequence nor in determining whether sites could be introduced by silent mutations. The other button has a symbol showing an arrow pointing to the left that can be selected by the user to move sites from the list titled Excluded Sites to the list titled Site Search List. These sites once moved from the Excluded Sites list, will participate in the process of determining the existence of restriction sites and determining whether restriction sites may be introduced by silent mutations. If the user is satisfied with the selection, an OK button may be selected to exit from the user interface 322. A Cancel button is also available for the user to select to exit without changes. Another button titled Edit Site List is available for selecting and upon selection will bring the user to a user interface 324. See FIG. 3L.

Figure 3M:
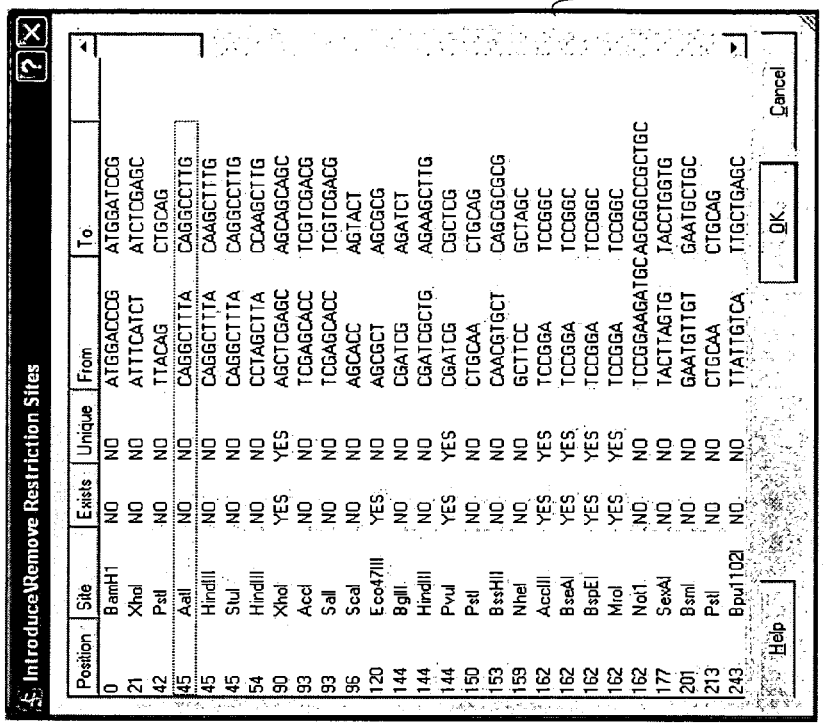
Figure 3L:
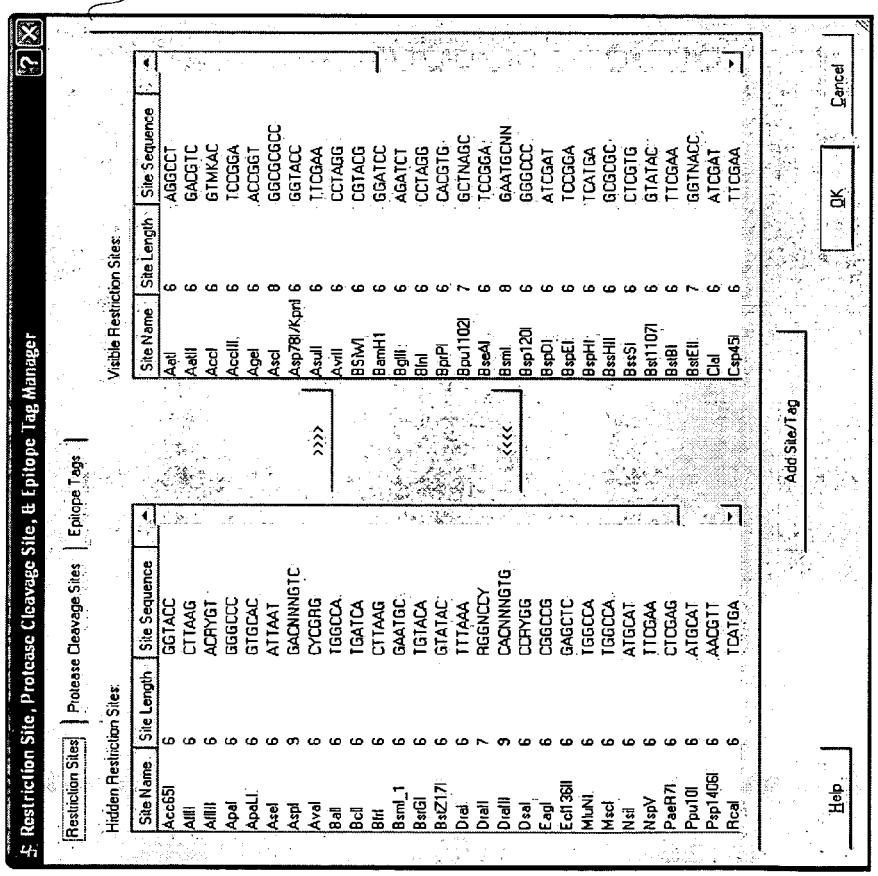

FIG. 3L illustrates the user interface 324 for managing a collection of restriction sites, Protease cleavage sites, and epitope tags in the system 100. There are three tags available to the user interface 324, Restriction Sites tag, Protease Cleavage Sites tag, and Epitope tabs. On each tab, there are two lists, hidden and visible. The hidden list contains the sites or tags that are stored in the databases 114 but will not be shown or used in composing gene sequences. The visible list is the list of sites or tabs that will be shown and used in gene synthesis. To move from one list to the other there are two buttons available for selection by the user. One button has a symbol of an arrow pointing to the right to move sites or tags from the hidden list to the visible list. The other button has a symbol in the form of an arrow pointing to the left to move sites or tags from the visible list to the hidden list. Each list has three columns. The first column titled Site Name displays the name of the site or tag. The second column titled Site Length displays the length of the site. The third column titled Site Sequence shows the nucleic acid sequence of the sites or tags. When the user is satisfied with sites or tags in the hidden list and the sites or tabs in the visible list, the user may select an OK button to exit from the user interface 324. If the user does not desire any changes, a Cancel button can be selected to exit from the user interface 324. A tab titled Add Site/Tab can be selected by the user to invoke a user interface 328. See FIG. 3N.

FIG. 3M illustrates a user interface 326, which is used to introduce or remove restriction sites by the user. A list of six columns contains several restriction sites selectable by the user to indicate whether to introduce or remove the particular restriction site. The first column titled Position indicates the location at which the restriction site can be found. The second column titled Site indicates the name of the restriction site. The third column titled Exists indicates whether the restriction site exists at that particular location. The fourth column titled Unique indicates whether a particular restriction site is the only one that exists in the entire nucleic acid sequence. The fifth and sixth columns are titled From and To. The From column indicates the nucleic acid sequence at the particular location, and the To column is a proposed silent mutation to introduce or remove a restriction site. Two buttons at the bottom of the user interface 326 can be selected by the user to exit without making changes (the Cancel button) or to confirm changes made (the OK button).

Figures 3N, 4A:
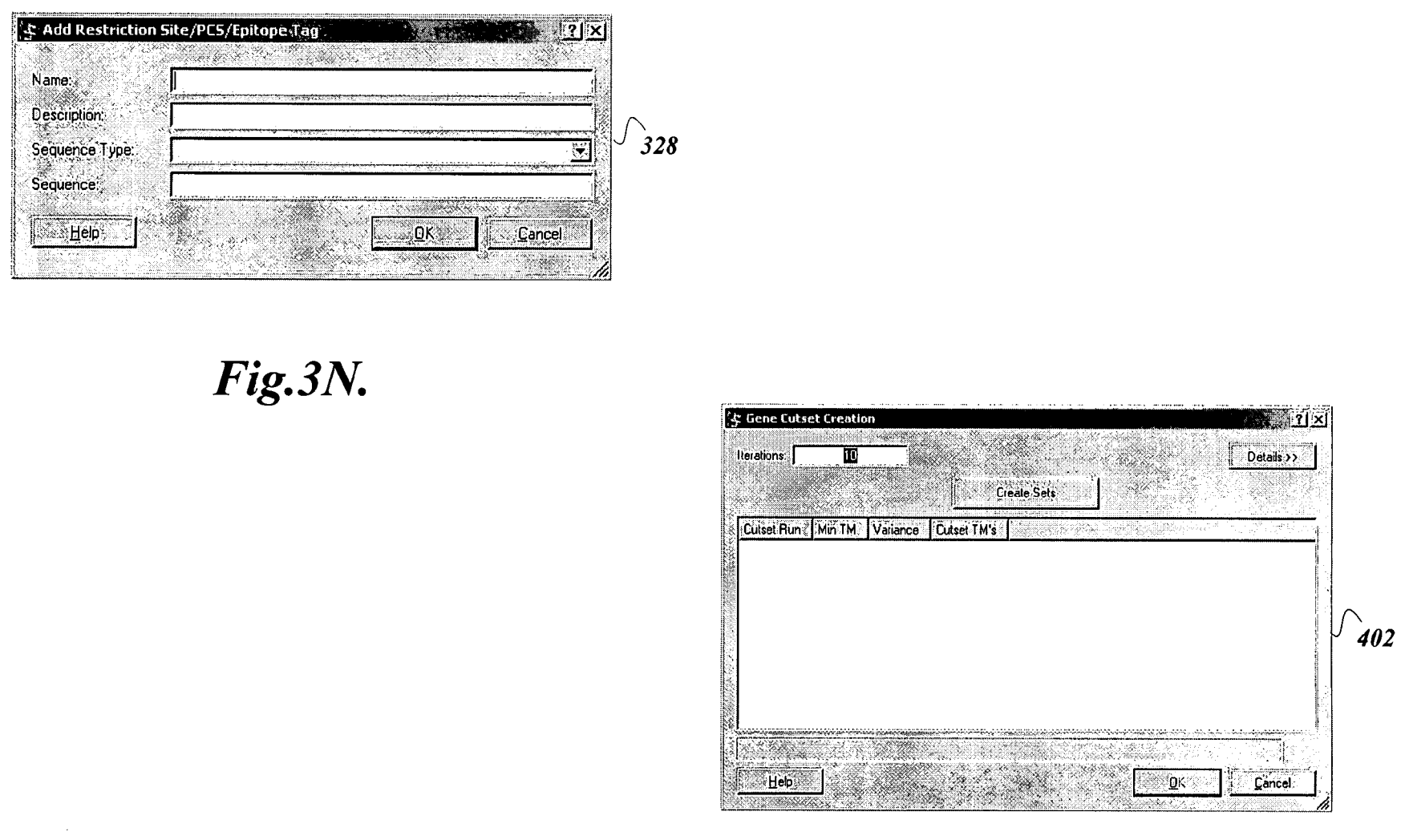

FIG. 3N illustrates a user interface 328 for adding a restriction site, or a Protease cleavage site, or an epitope tag. A text box titled Name allows the user to specify the name for the restriction site, the Protease cleavage sites, or the epitope tag. Another text box titled Description allows the user to enter a narrative describing the added restriction site, Protease cleavage sites, or epitope tag. A pull down text box titled Sequence Type, when selected by the user, specifies whether the added element is a restriction site, a Protease cleavage site, or an epitope tag. The last text box titled Sequence is used by the user to specify nucleic acid pattern, amino acid pattern, or wobble letters. To accept the changes made, the user can select an OK button. To exit without making changes, the user selects a Cancel button FIG. 4A illustrates a user interface 402 for creating run sets, or cut sets, or a set of oligonucleotides used in whole gene synthesis for the current gene sequence. The process of creating oligonucleotides begins by randomly dividing a duplex gene sequence into a number of possible overlapping sets of oligonucleotides. These oligonucleotides are then checked to see if they happen to meet defined constraints for oligonucleotide length limits (usually between 55 and 75 bases) and overlap length limits (usually between 20 to 30 bases). The first number (such as 1000 or other suitable numbers) of oligonucleotide sets that pass are then ranked and ordered based on their minimum overlapping melting temperatures and statistical variance in the overlapping melting temperatures.

Various embodiments of the present invention use a nearest-neighbor technique to calculate the melting temperature at a specified salt concentration (usually the same salt concentration used during gene assembly). From this analysis, the top 5% of the oligonucleotide sets with the lowest variance in overlap melting temperatures are preferably submitted to additional analyses to identify which of the oligo sets have the fewest number of "outlier" oligos; which have either (i) a low overlap melting temperature compared to the average melting temperature for all overlaps, (ii) a sequence that is capable of forming a stable hairpin, or (iii) a sequence that has high potential to mispair with one of other oligonucleotides in the set. The best oligonucleotide set is then selected for further refinement wherein the outlier oligos are improved. This can be achieved either by shifting the endpoints of the oligonucleotide by one or two bases (and simultaneously also the endpoints of the its neighboring adjacent oligonucleotide), or alternatively by the introduction of a point base change in the top and bottom strand oligonucleotides such that they complement each other. Various embodiments of the present invention invoke a "conflict resolution" algorithm to select a base sequence change that may improve the accuracy of gene assembly versus or one that may improve protein expression.

Returning to the user interface 402, a text box titled Iterations allows the user to specify the number of iterations to run the cut set creation process to create oligonucleotides. The more iterations that are used, the less likely the cut set will require further adjustments to get the desired melting temperature for the oligonucleotides above the minimum melting temperature threshold. A button titled Create Sets can be selected by the user to begin the process of analyzing the gene sequence to create the set of oligonucleotides for synthesis. A list of four columns appear to present the analyzed cut sets. The first column titled Cut Set Run shows the iteration number generated by the process. The second column titled Minimum Melting Temperature indicates the minimum melting temperature of the cut set. The third column titled Variance displays the variance of the melting temperature across the gene sequence. The last column is titled Cut Set Melting Temperature and indicates the melting temperatures of the oligonucleotides for a particular cut set. A Details button is available for users who wish to set parameters used in creating oligonucleotides, such as the maximum oligonucleotide size, the minimum oligonucleotide size, the minimum first size, the maximum mid size, the minimum mid size, the maximum last size, the minimum last size, the overlap threshold, the number of keep sets, whether the process should automatically create mid sizes, and finally whether the process should automatically shift cut set to improve melting temperature, among other things. Two buttons can be selected by the user, an OK button and a Cancel button. The OK button when pressed will confirm the oligonucleotides created by the process and exit the user from the user interface 402. The Cancel button when pressed allows the user to exit from the user interface 402 without further changes.

Figures 4B, 4C:
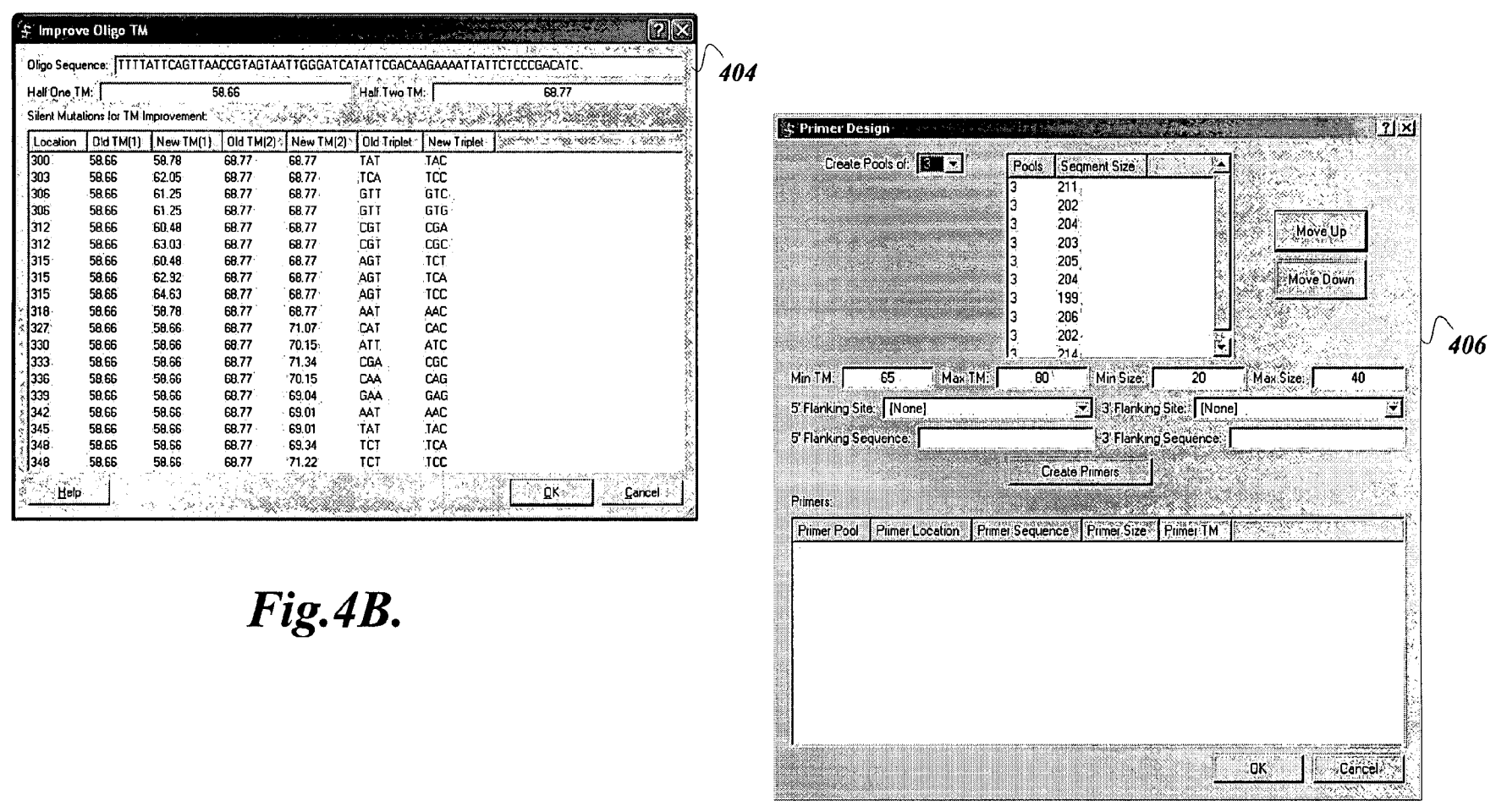

FIG. 4B illustrates a user interface 404 for improving the melting temperature of oligonucleotides. A text box titled Oligo Sequence allows the user to specify in terms of nucleic acid sequence which melting temperature should be analyzed for improvement. Two text boxes titled Half One Melting Temperature and the other Half Two Melting Temperature indicates the melting temperatures for one half of the specified oligonucleotide sequence and the remaining half of the same sequence. A list also is presented by the user interface 404 for showing silent mutations proposed to the oligonucleotides that would improve the melting temperature of each half. Each item in the list shows the location of the silent mutation, the original melting temperature of each half of the oligonucleotide sequence, the new melting temperature for each half of the oligonucleotide sequence, the old triplet, and a new triplet for improving the melting temperature. The user may select one or more items from the list to indicate that at the particular location, the melting temperature should be improved by the proposed silent mutations (shown by the new triplet). If the user is satisfied with the selection of one or more items for improving the melting temperature of the oligonucleotide, an OK button may be selected to exit from the user interface 404. If no changes are desired, the user may select a Cancel button to exit from the user interface 404.

FIG. 4C illustrates a user interface 406 for designing primers. The user interface element 406 allows the user to create a set of primers for the oligonucleotides based on a particular pooling strategy. The user interface element 406 is available only if a run set or cut set has been created for the gene sequence. A pooling strategy is specified by indicating how many oligonucleotides will be pooled together to form a gene fragment which will later be pooled together to form the gene sequence. The user can select the number of top strand oligonucleotides to be included in each pool by clicking on a pull down combo box titled Create Pools Off and specify the number of pools to be created. A list to the right of the combo box titled Create Pools Of will be updated with the number of oligonucleotides in each pool and the size of each gene fragment formed by each pool. For example, the list includes a column titled Pools to indicate the number of oligonucleotides in each pool. A second column titled Segment Size indicates the gene fragment sized to be formed by each pool. If there is a pool or pools that have more oligonucleotides than other pools, their location in the gene sequence can be adjusted by selecting the appropriate pool on the list and then clicking one of two buttons titled Move Up and Move Down to effectuate the relocation of the pool in the gene sequence. The user interface 406 also provides additional parameters in the design of primers for whole gene synthesis. The minimum and maximum melting temperature can be specified for the primers. The minimum and maximum size can be specified for the primers to be created. Additionally, two combo boxes for the user to specify the 5' flanking site and the 3' flanking site. Two text boxes titled 5' flanking sequence and 3' flanking sequence allows the user to enter his own flanking sites for the 5' and 3' ends of the primers being designed. When the user is satisfied with the parameters, the user may select the Create Primers button to create them. A list of five columns, the first column titled Primer Pool, the second column titled Primer Location, the third column titled Primer Sequence, the fourth column titled Primer Size, and the fifth column titled Primer Melting Temperature, provide pieces of information connected with the created primers. If the user is satisfied with the created primers, an OK button may be selected to exit from the user interface 406. Otherwise, a Cancel button can be selected to exit without changes.

Figure 4D:
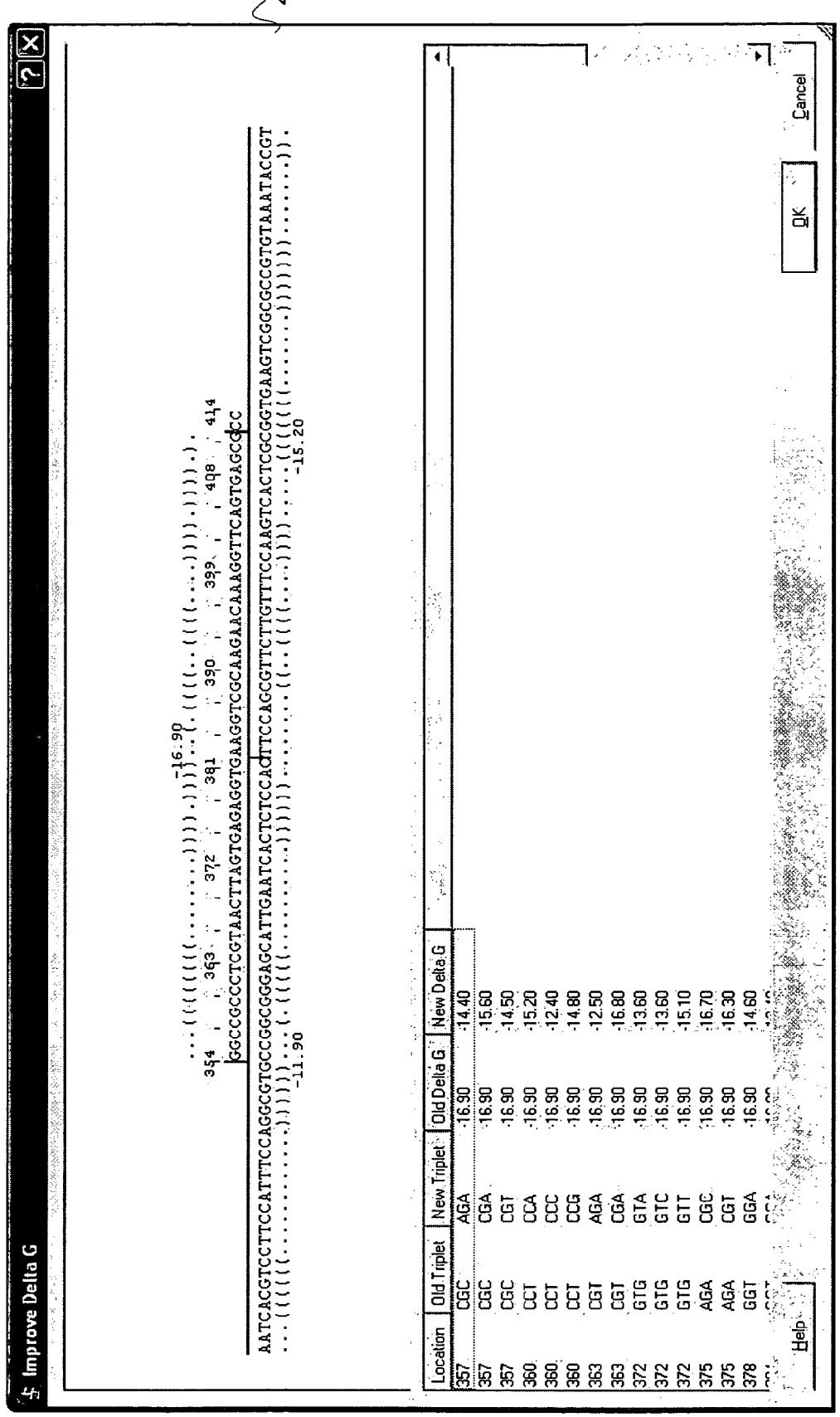
FIG. 4D is a pictorial diagram illustrating an exemplary user interface for improving the free energy of a gene sequence (delta g)

FIG. 4D illustrates a user interface 408 for improving the delta g or free energy of oligonucleotides. The user interface 408 displays the oligonucleotide that is selected, the oligonucleotides affected by changes to the selected oligonucleotide, and corresponding free energy values and fold structure connected with these oligonucleotides. A list view at the lower half of the user interface 408 shows the set of possible silent mutations that would improve the free energy value. Each item on the list shows the location of the silent mutation, the original codon triplet, the new codon triplet, the original free energy value, and the free energy of the oligonucleotide for that particular silent mutation. The user may select a particular item to improve the free energy value of the oligonucleotide. The upper half of the user interface 408 will be updated to show how the selection would affect each oligonucleotide. When the user is satisfied with the improvement, an OK button may be selected to exit from the user interface 408. If no changes are desired, a cancel button may be selected by the user.

Figure 4E:
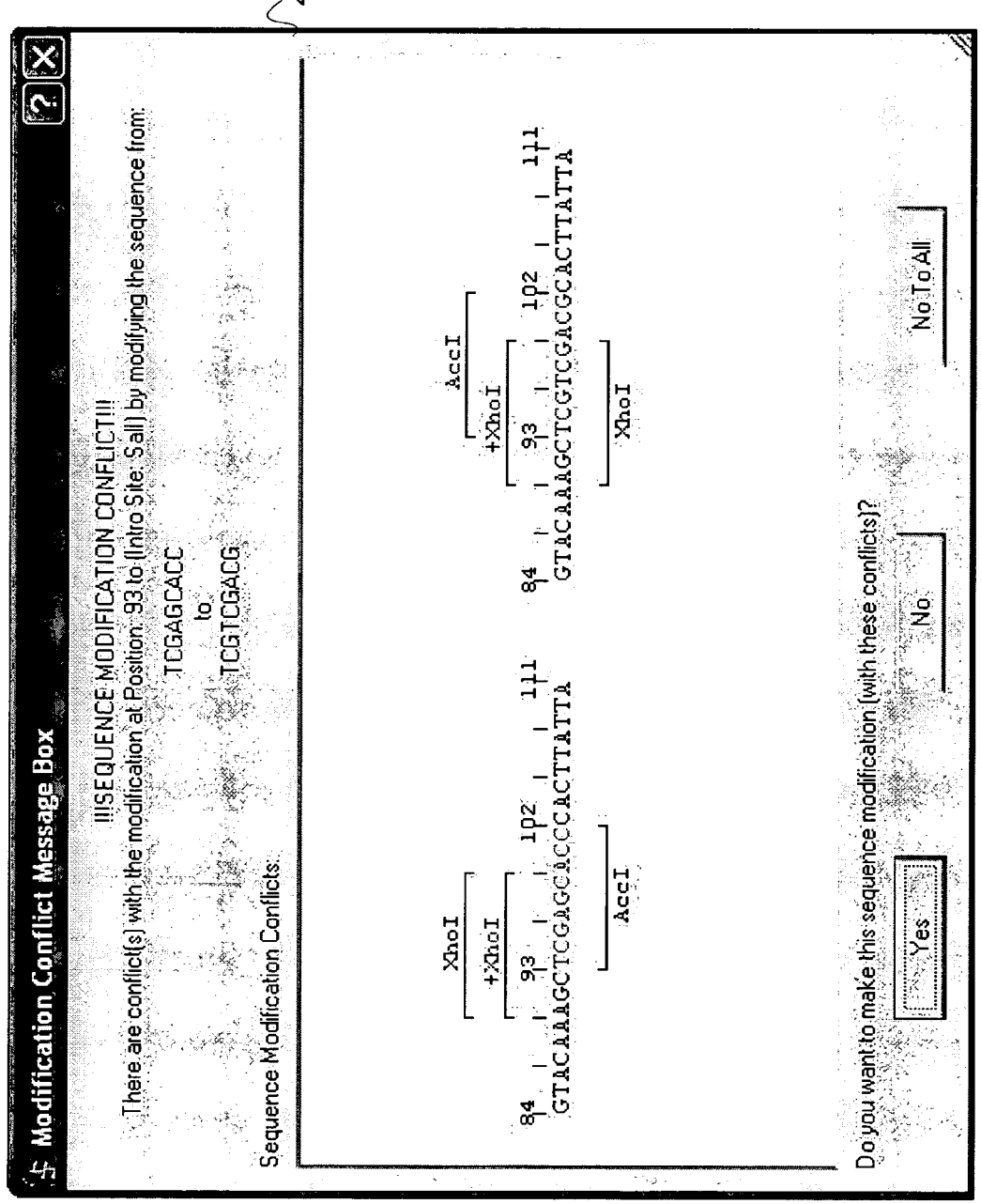
FIG. 4E is a pictorial diagram illustrating an exemplary user interface for genetic modification conflict resolution.

A user interface 410 is illustrated at FIG. 4E. The user interface 410 appears whenever there is a mutation modification conflict requiring resolution. More specifically, when a silent mutation or gene modification is being made to the gene sequence and it conflicts with previous modifications, the user interface 410 is presented to allow the user to attempt a resolution. The user interface 410 presents the location of the modification, the type of modification, the original sequence, the modified sequence, and a visual representation of the affected portion of the gene sequence that shows which modifications and/or restriction sites that are affected. For example, in the exemplary illustration at FIG. 4E, a modification at position 93 in the gene sequence to introduce the SALI restriction site (in other words, changing the sequence from TCGACGACC to TCGTCGACG) will cause the Xho I site that was introduced to be removed and the Acc I site that did not exist before in the sequence will now be introduced. If the user desires the modification, the user can select the Yes button to proceed. To cancel the particular modification, the user may select a button titled No. If the user selects a button titled No to all, the system 100 will cancel the remaining modifications that were to be made to the sequence.

Other user interfaces not shown include a number of visualization tools. For example, a rare codon histogram viewer allows the researcher to quickly visualize the density of rare codons in a given gene sequence. Predicted stable mRNA structures are also presented along the nucleic acid sequence as a color coded histogram of calculated local delta g of folding. This allows researchers to see the relative contribution of stable mRNA structures as a function of calculated delta g of folding at regular intervals along the mRNA. Similar visualization of melting temperature and GC content of overlapping assembly oligonucleotides are also available. These visualization tools are especially useful when used in combination with conflict resolution tools which allow researchers to make an informed choice, for example between having a desired restriction site present in the final gene sequence, or instead eliminating a stable predicted mRNA hairpin that results from the presence of the engineered restriction site.

Figure 5A:
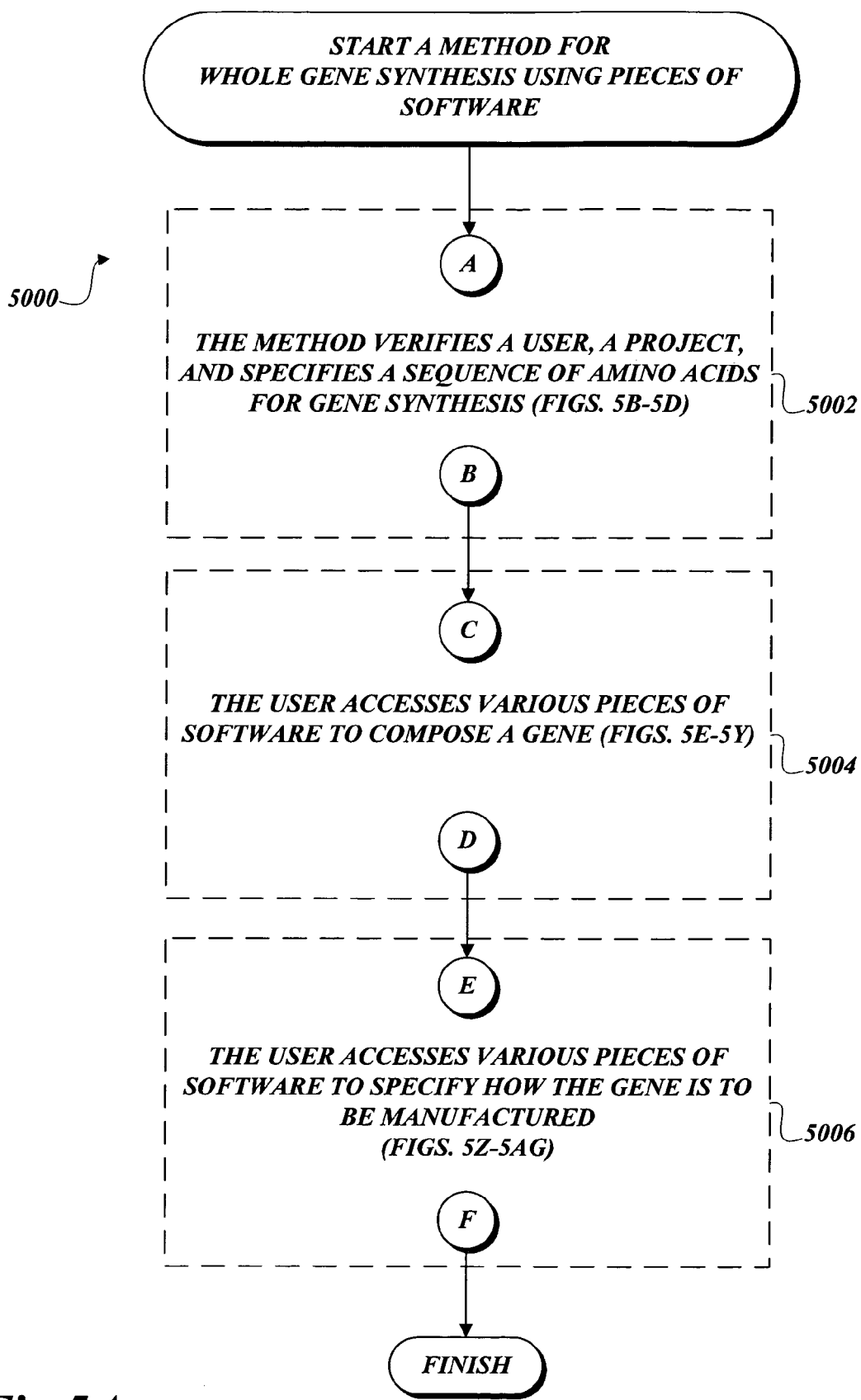
FIGS. 5A-5AG are process diagrams for illustrating methods for whole gene synthesis using pieces of software.
Figure 5B:
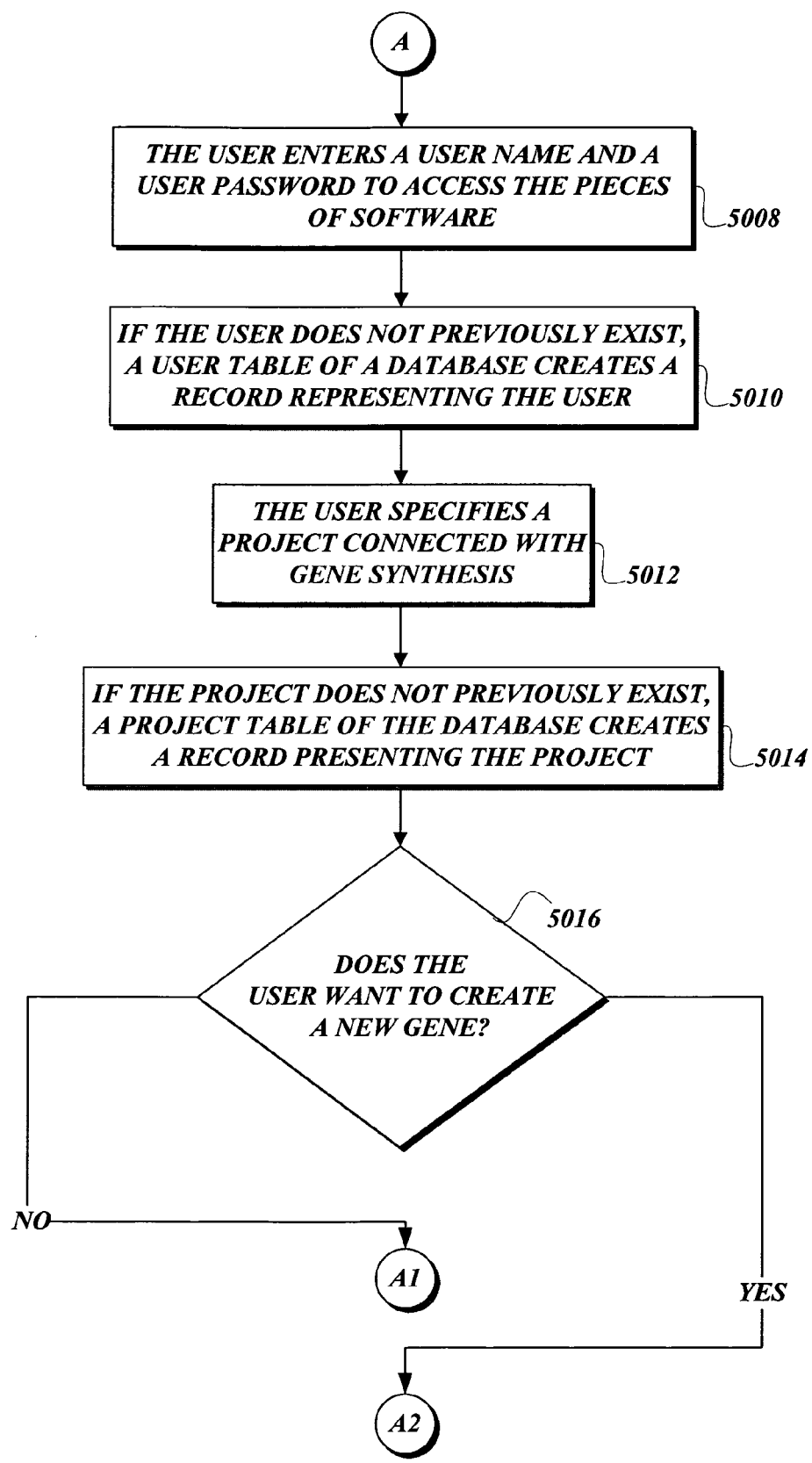

FIGS. 5A-5AG illustrate a method 5000 for whole gene synthesis using pieces of software. The method can simultaneously exploit the degeneracy of the genetic code while it is mindful of biophysical properties of nucleic acids to design optimal DNA coding sequences that can be synthesized by PCA or solid-phase assembly methods from synthetic oligonucleotides. From a start block, the method 5000 proceeds to a set of method steps 5002, defined between a continuation terminal ("Terminal A") and an exit terminal ("Terminal B"). The set of method steps 5002 describe the verification of a user, a project, and a specified sequence of amino acids or nucleic acids for gene synthesis. From Terminal A (FIG. 5B), the method 5000 proceeds to block 5008 where the user enters a user name and a user password to access the pieces of software connected with the system 100. If the user does not previously exist, the users table 116 of the databases 114 creates a record representing the user if the administrator of the system 100 authorizes such a transaction. See block 5010. At block 5012, the user specifies a project connected with gene synthesis. If the project did not previously exist, the projects table 118 of the databases 114 creates a record representing the project. See block 5014. Next, at decision block 5016, a test is performed to determine whether the user wants to create a new gene. If the answer is No to the test at decision block 5016, the methods continue to another continuation terminal ("Terminal A1"). Otherwise, the answer to the test at decision block 5016 is Yes, and the methods proceed to another continuation terminal ("Terminal A2").

Figure 5C:
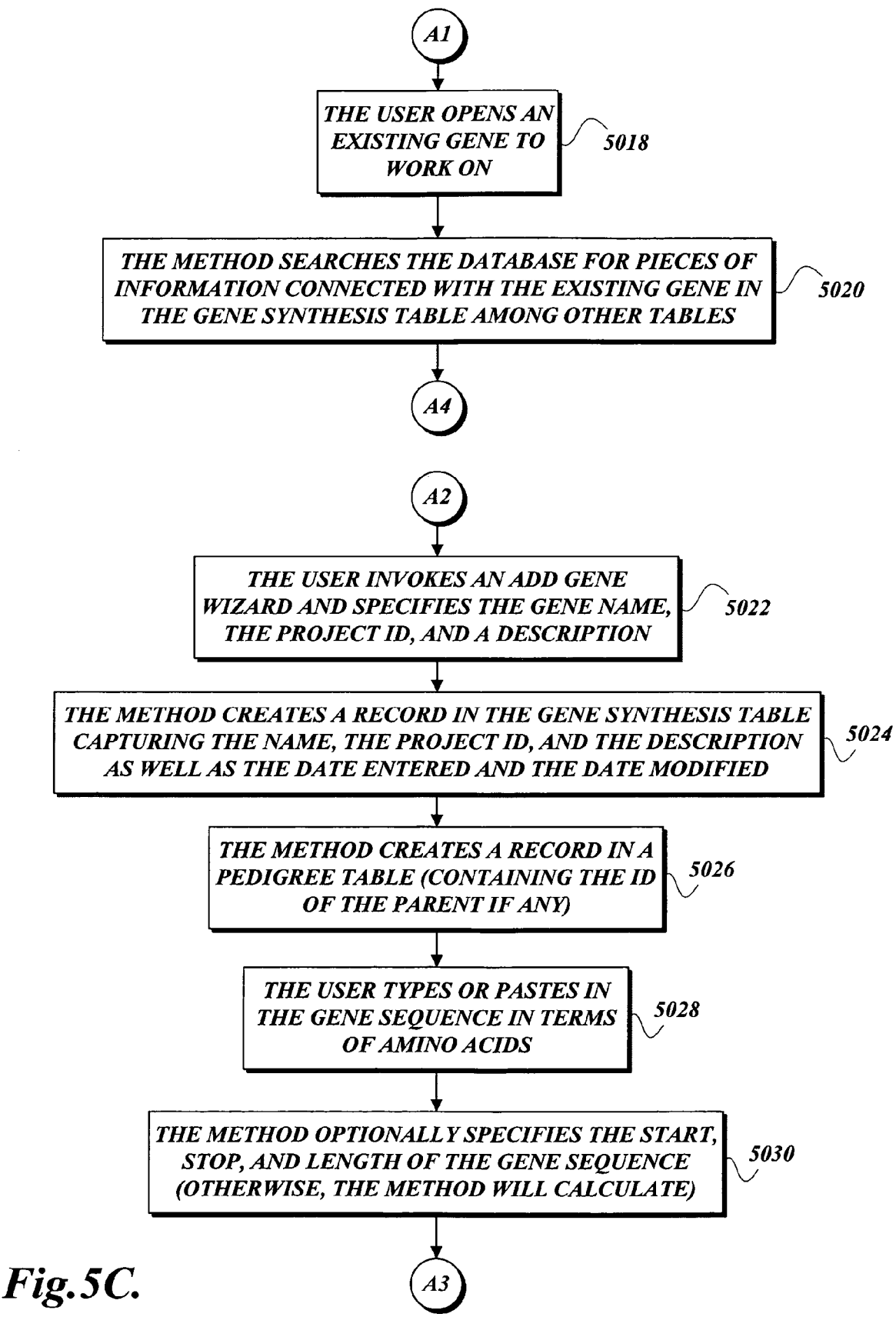

From Terminal A1 (FIG. 5C), the user opens an existing gene to work on. See block 5018. At block 5020, the method searches the database for pieces of information connected with the existing gene in the gene synthesis table 120, among other tables. The method then continues to another continuation terminal ("Terminal A4").

From Terminal A2 (FIG. 5C), the user invokes an Add Gene wizard and specifies the gene name, the project ID, and a description. See block 5022. See also user interfaces 204-208. The method creates a record in the gene synthesis table capturing the name, the project ID, and the description as well as the date entered and the date modified. See block 5024. At block 5026, the method creates a record in the pedigree table 130 (containing the ID of the parent, if any). At block 5028, the user types or pastes in the gene sequence the terms of amino acids or nucleic acids. At block 5030, the software automatically specifies the start, stop, and length of the gene sequence (otherwise, the method will calculate). The method then continues to another continuation terminal ("Terminal A3").

Figure 5D:
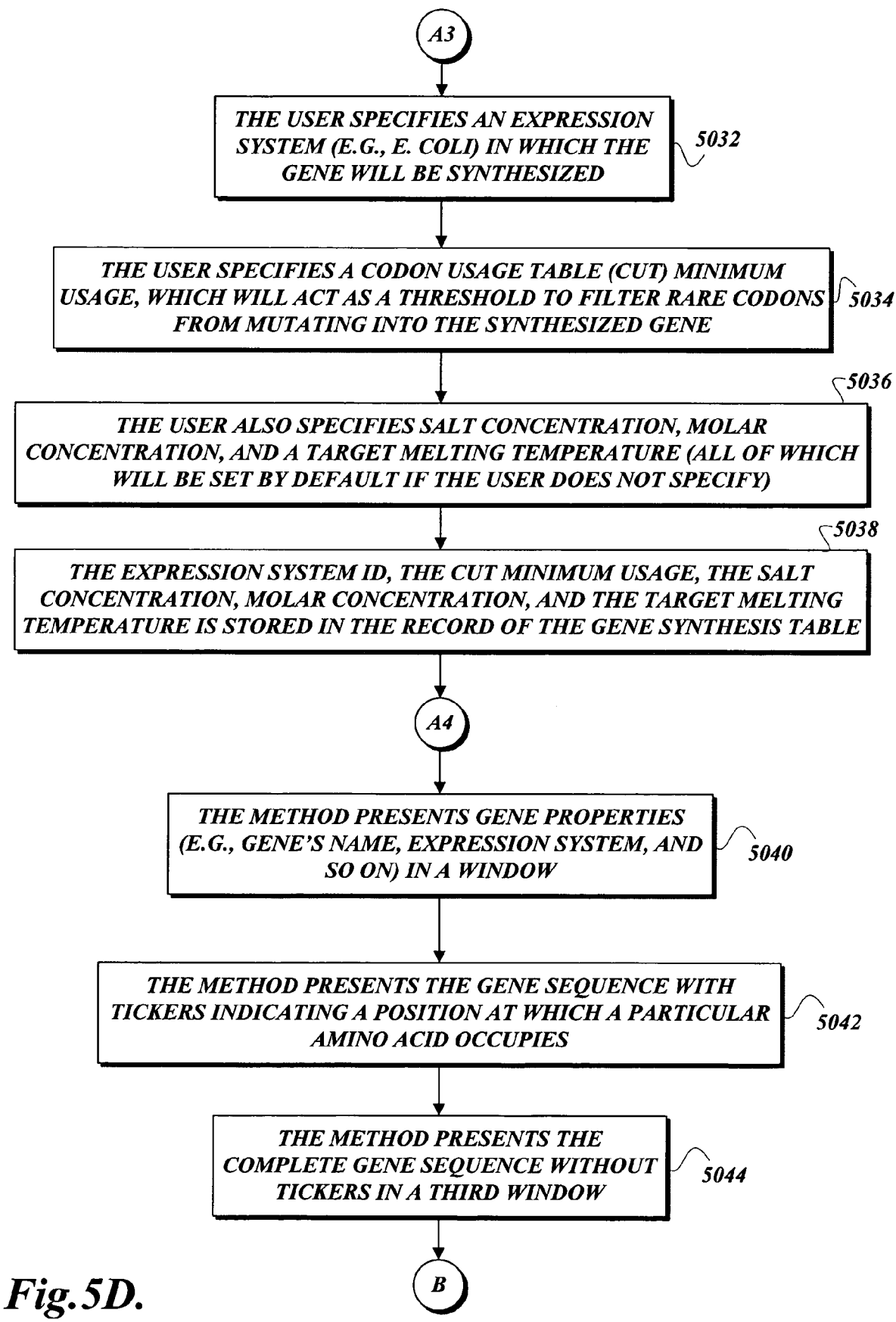

From Terminal A3 (FIG. 5D), the user specifies an expression system of an organism (e.g., *E. coli*) in which the gene would be synthesized. At block 5034, the user specifies a codon usage table (CUT) minimum usage, which will act as a threshold to filter rare codons from mutating into the synthesized gene sequence. Next, at block 5036, the user also specifies salt concentration, molar concentration, and a target melting temperature (all of which will be set by default if the user does not specify). The expression system identification, the cut minimum usage, the salt concentration, the molar concentration, and the target melting temperature are stored in the record of the gene synthesis table 120. See block 5038. The method then continues to Terminal A4 and proceeds to block 5040 where the method presents the gene's properties (e.g., the gene's name, expression system, and so on) in a window. See user interface 210. The method then presents the gene sequence with tickers indicating a position occupied by a particular amino acid. At block 5044, the method presents the complete gene sequence without tickers in a third window. See user interface 214 of FIG. 2G. The method then continues to exit Terminal B.

Figure 5E:
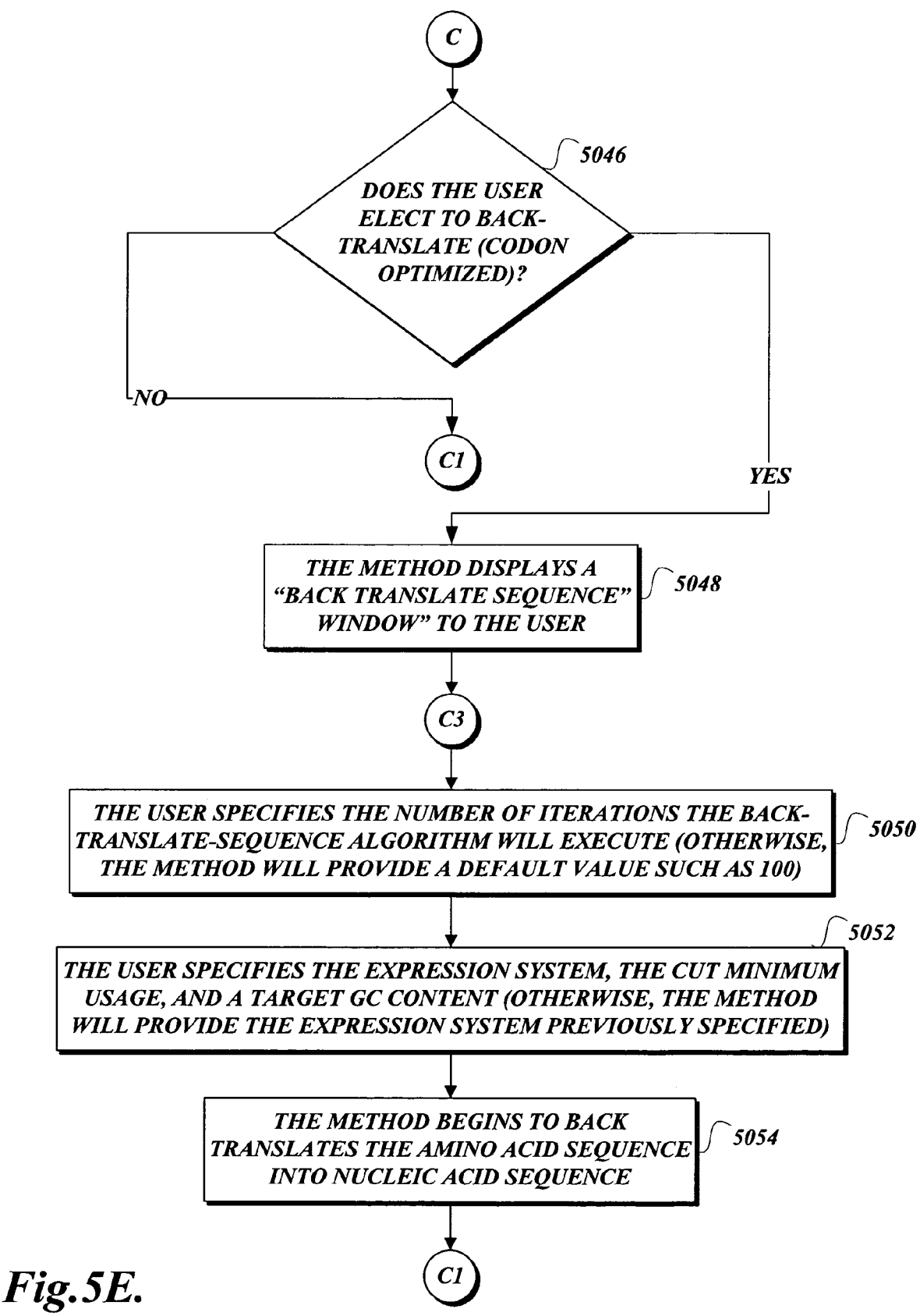

From exit Terminal B (FIG. 5A), the method 5000 proceeds to another continuation terminal ("Terminal C") and an exit terminal ("Terminal D"). The set of method steps 5004 between Terminals C-D allow the user to access various pieces of software to compose a gene. From Terminal C (FIG. 5E), the method proceeds to decision block 5046 where a test is performed to determine whether the user elects to back translate (codon optimized). If the answer to the test at decision block 5046 is No, the method 5000 proceeds to another continuation terminal ("Terminal C1"). If the answer to the test at decision block 5046 is Yes, the method continues to block 5048 where the method displays a back translate sequence window to the user. See the user interface 302. The method then continues to another continuation terminal ("Terminal C3"). The method then proceeds to block 5050 where the user specifies the number of iterations the back translate sequence algorithm will execute (otherwise, the method will provide a default value such as 100). At block 5052, the user specifies the expression system, the cut minimum usage, and a target GC content (otherwise, the method will provide the expression system previously specified). The method begins to back translate the amino acid sequence into nucleic acid sequence. See block 5054. The method then continues to Terminal C1.

Figure 5F:
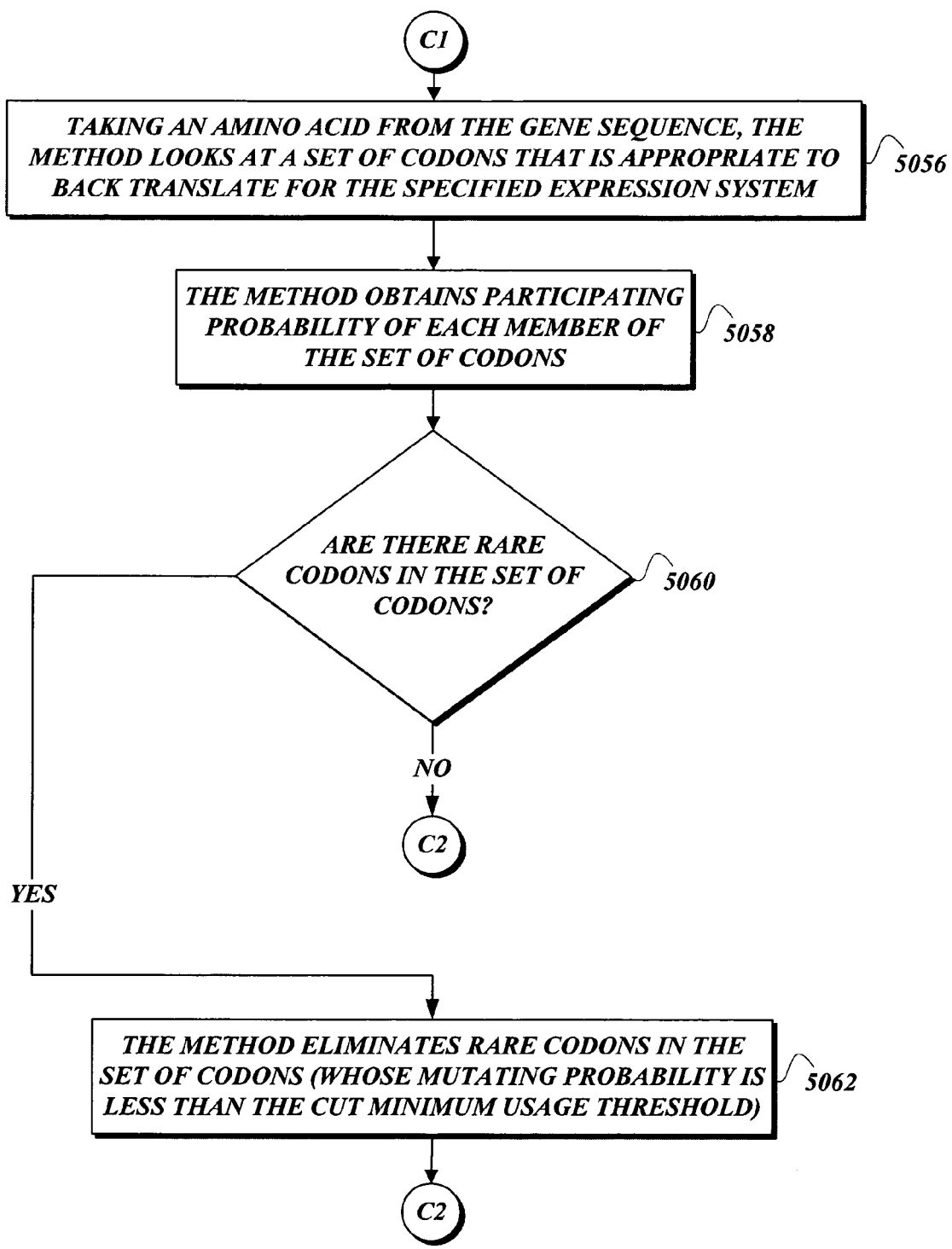

From Terminal C1 (FIG. 5F), taking an amino acid from the gene sequence, the method looks at a set of codons that is appropriate to back translate for the specified expression system. See block 5056. At block 5058, the method obtains a participating probability for each member of the set of codons. Next, at decision block 5060, a test is performed to determine whether there are rare codons in the set of codons. If the answer to the test at decision block 5060 is No, the method proceeds to another continuation terminal ("Terminal C2"). If the answer to the test at decision block 5060 is Yes, the method eliminates rare codons in the set of codons (whose mutating probability is less than the cut minimum usage threshold). See block 5062. The method then continues to Terminal C2.

Figure 5G:
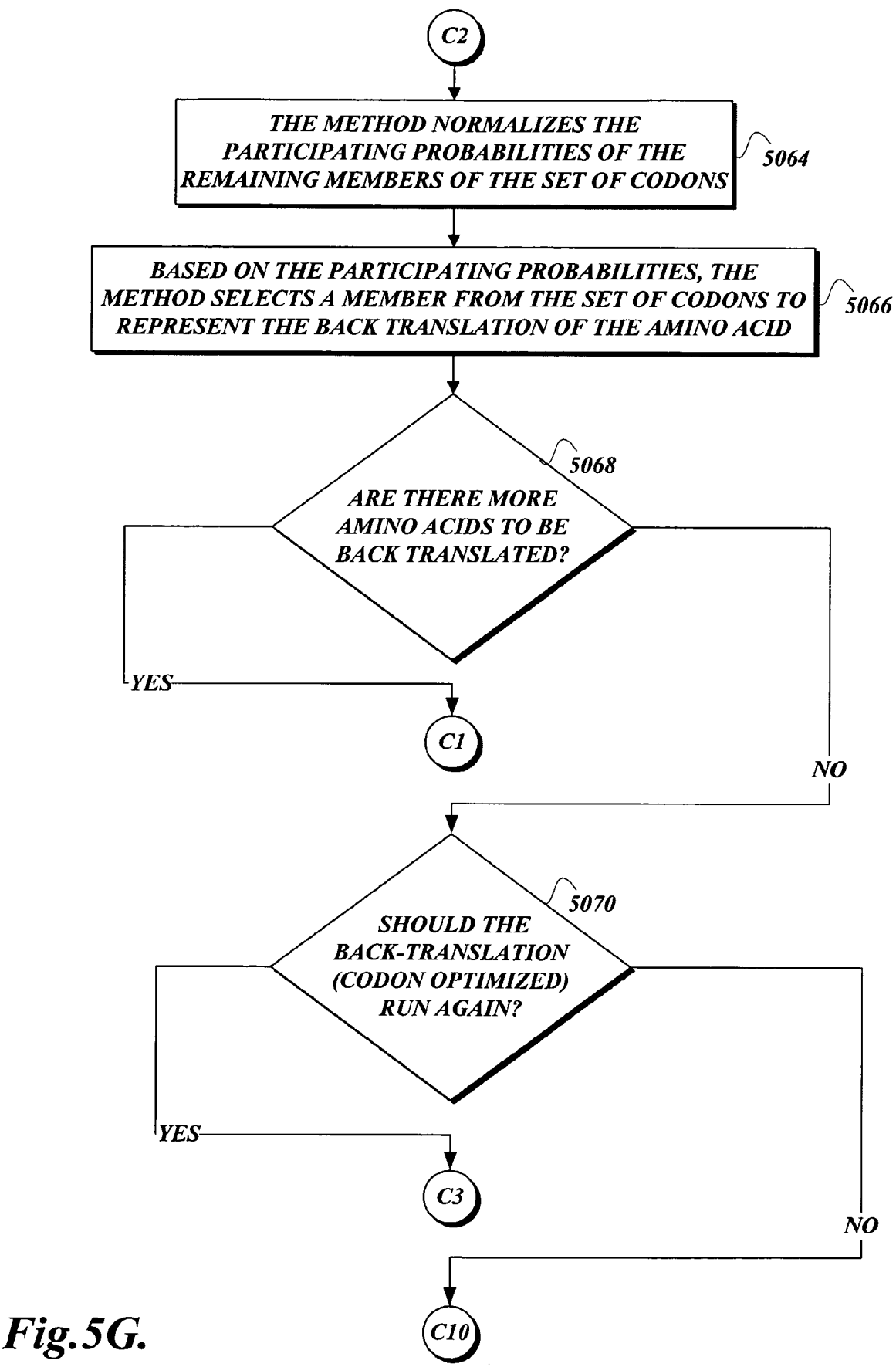

From Terminal C2 (FIG. 5G), the method proceeds to block 5064 where the method normalizes the participating probabilities of the remaining members of the set of codons. At block 5066, based on the participating probabilities, the method selects a member from the set of codons to represent the back translation of the amino acid. A test is performed at decision block 5068 where the method determines whether there are more amino acids to be back translated. If the answer to the test at decision block 5068 is Yes, the method continues to Terminal C1 to jump back to block 5056 where the above-discussed method steps are repeated. Otherwise, the answer to the test at decision block 5068 is No, and another decision block 5070 is entered by the method where another test is performed to determine whether the back translation should be run again. If the answer to the test at decision block 5070 is Yes, the method continues to Terminal C3 to jump back to block 5050 where the above-identified processing steps are repeated. Otherwise, the answer to the test at decision block 5070 is No, and the method continues to another continuation terminal ("Terminal C10").

Figure 5H:
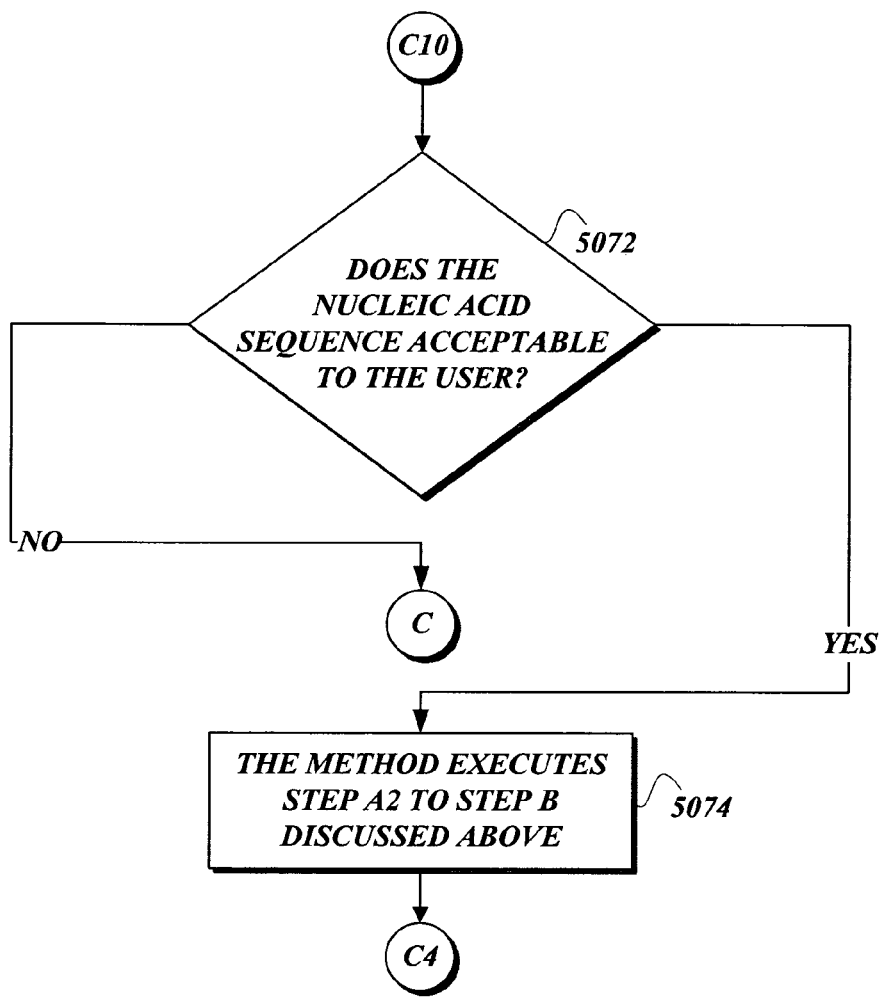

From Terminal C10 (FIG. 5H), the method continues to another decision block 5072 where another test is performed to determine whether the nucleic acid sequence is acceptable to the user. If the answer to the test at decision block 5072 is No, the method continues to Terminal C to jump back to decision block 5046 where the above-discussed processing steps are repeated. Otherwise, the answer to the test at decision block 5072 is Yes, and the method continues to block 5074 where the method executes step A2-step B discussed above. The method then continues to another continuation terminal ("Terminal C4").

Figure 5I:
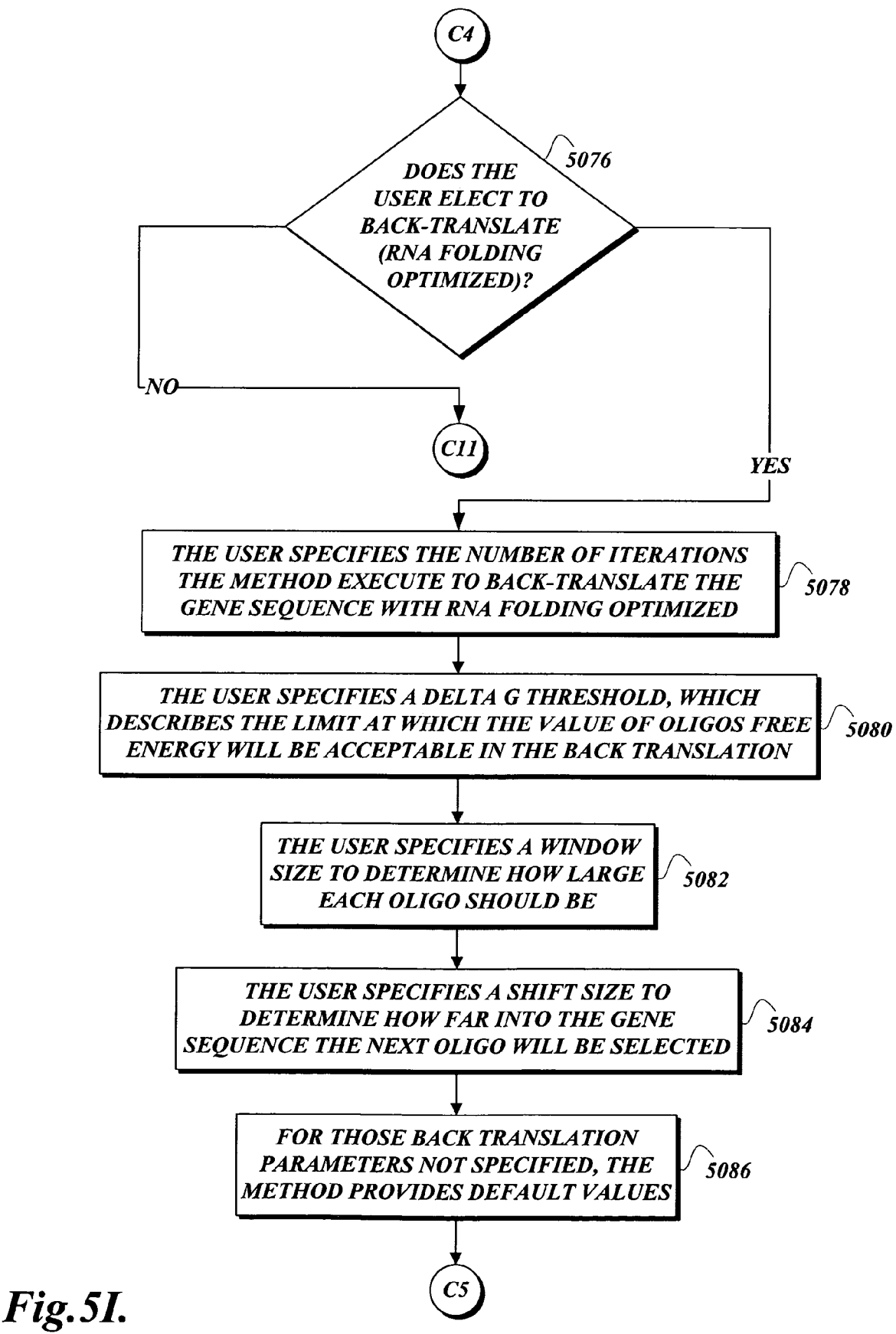

From Terminal C4 (FIG. 5I), the method proceeds to decision block 5076 where a test is performed to determine whether the user selects to back translate using RNA folding optimized process. If the answer to the test at decision block 5076 is No, the method proceeds to another continuation terminal ("Terminal C11"). Otherwise, the answer to the test at decision block 5076 is Yes, and the method proceeds to block 5078 where the user specifies the number of iterations the method executes to back translate the gene sequence with RNA folding optimized. At block 5080, the user specifies a delta g threshold, which describes the limit at which the value of oligos free energy would be acceptable in the back translation. At block 5082, the user specifies a window size to determine how large each oligonucleotides should be. The user also specifies a shift size to determine how far into the gene sequence the next oligonucleotide will be selected. See block 5084. The method then proceeds to block 5086 where for those back translation parameters not specified, the method provides default values. The method then continues to another continuation terminal ("Terminal C5").

Figure 5J:
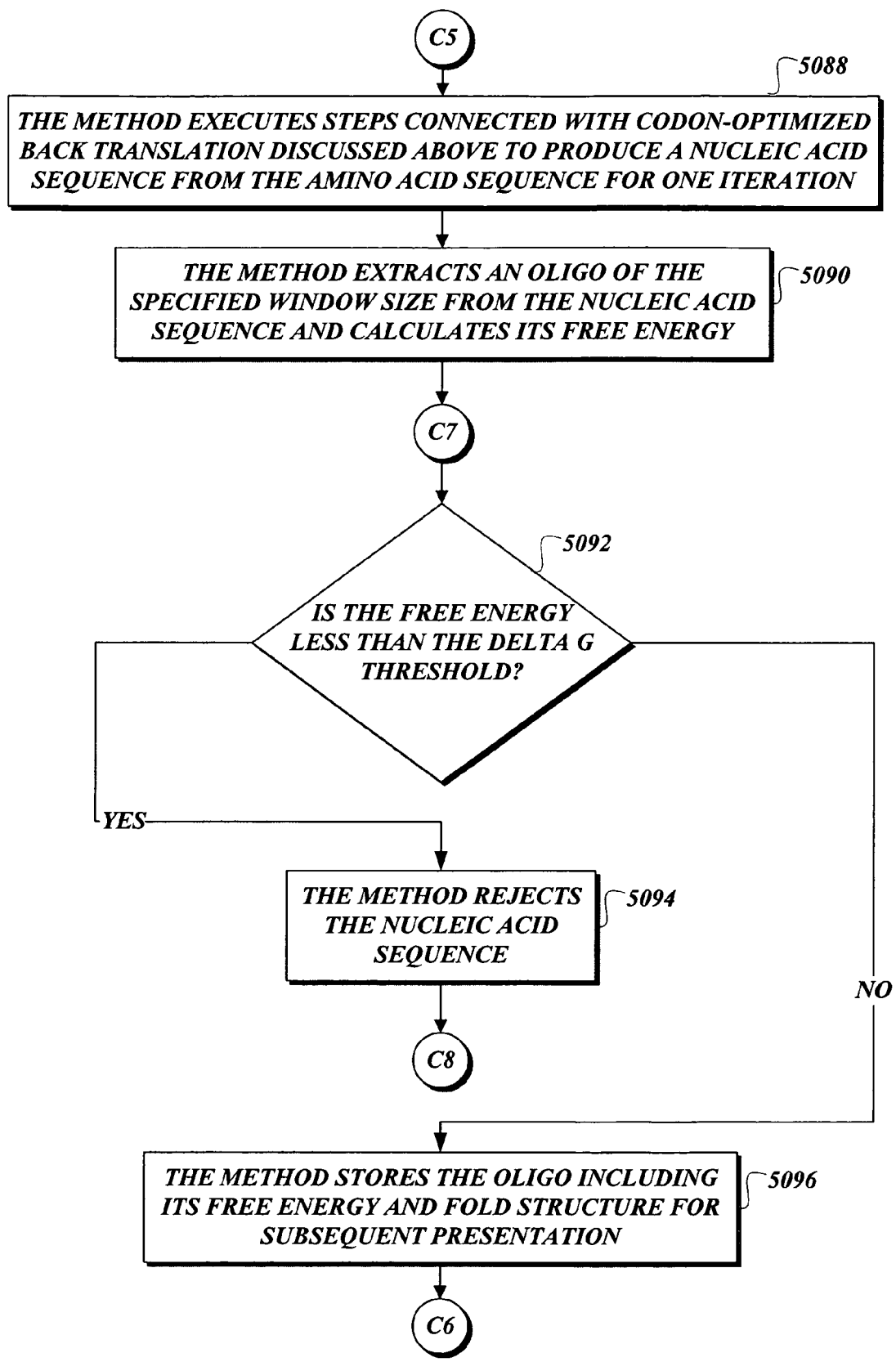

From Terminal C5 (FIG. 5J), the method executes steps connected with codon optimized back translation discussed above to produce a nucleic acid sequence from the amino acid sequence for one iteration. See block 5088. At block 5090, the method extracts an oligonucleotide of the specified window size from the nucleic acid sequence and calculates its free energy. The method then continues to another continuation terminal ("Terminal C7"). From Terminal C7, the method proceeds to another decision block 5092 where a test is performed to determine whether the free energy is less than the delta g threshold. If the answer is Yes to the test at decision block 5092, the method continues to block 5094 where the method projects the nucleic acid sequence. The method then continues at another continuation terminal ("Terminal C8"). Otherwise, the answer to the test at decision block 5092 is No, and the method proceeds to block 5096 where it stores the oligonucleotide including its free energy and fold structure for subsequent presentation. The method then continues at another continuation terminal ("Terminal C6").

Figure 5K:
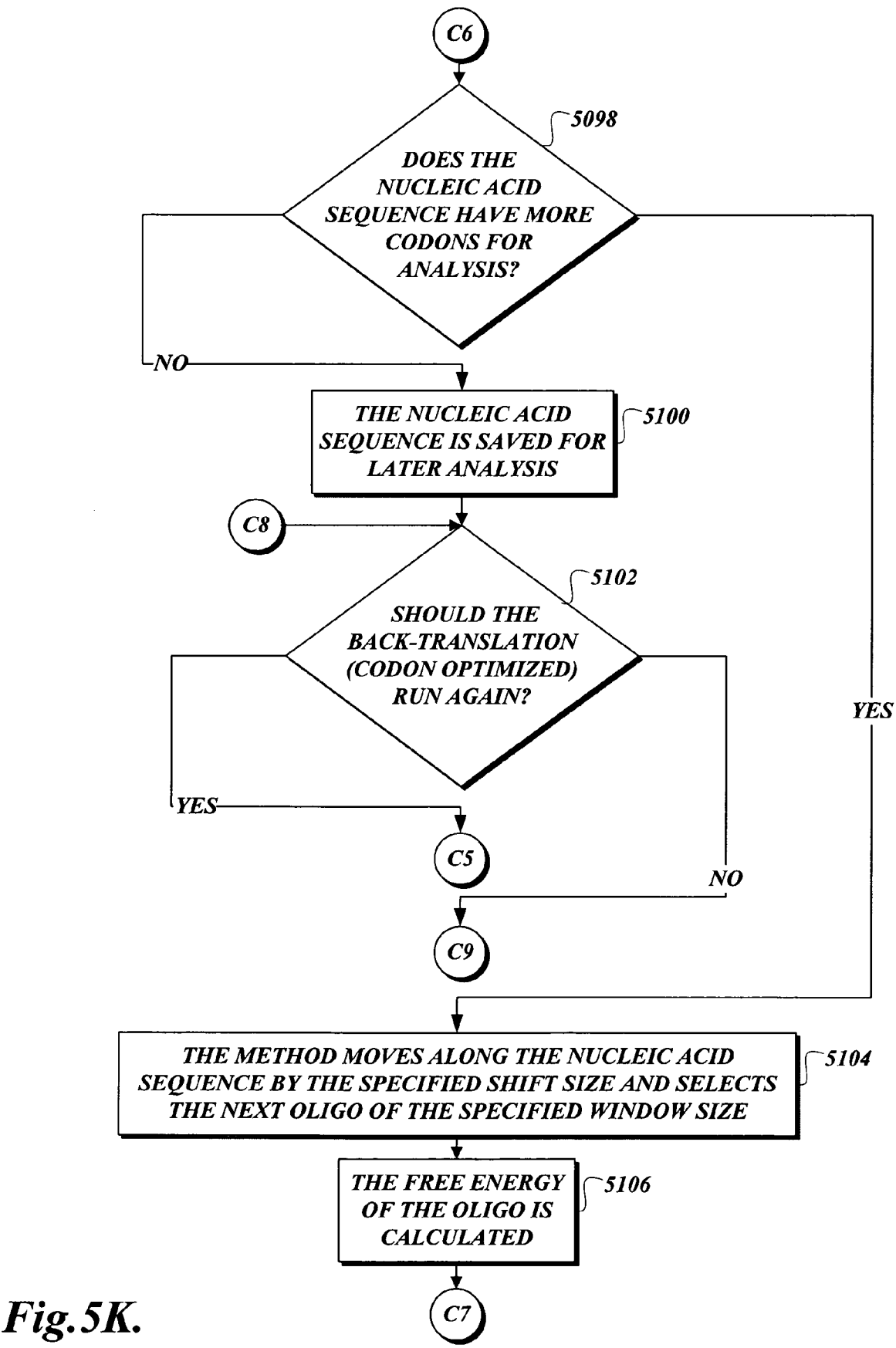

From Terminal C6 (FIG. 5K), the method proceeds to decision block 5098 where a test is performed to determine whether the nucleic acid sequences have more codons for analysis. If the answer to the test at decision block 5098 is Yes, the method proceeds to block 5014 where the method moves along the nucleic acid sequence by the specified shift size and selects the next oligonucleotide of the specified window size. The method then proceeds to block 5106 where the energy of the oligonucleotide is calculated. The method then continues to Terminal C7. If the answer to the test at decision block 5098 is No, the method continues to block 5100 where the nucleic acid sequence is saved for later analysis. Decision block 5012 is entered and a test is performed to determine whether the back-translation should be run again (codon-optimized). If the answer to decision block 5102 is No, the method continues to another continuation terminal ("Terminal C9"). Otherwise, the answer to the test at decision block 5012 is Yes, the method continues to another continuation terminal ("Terminal C5").

Figure 5L:
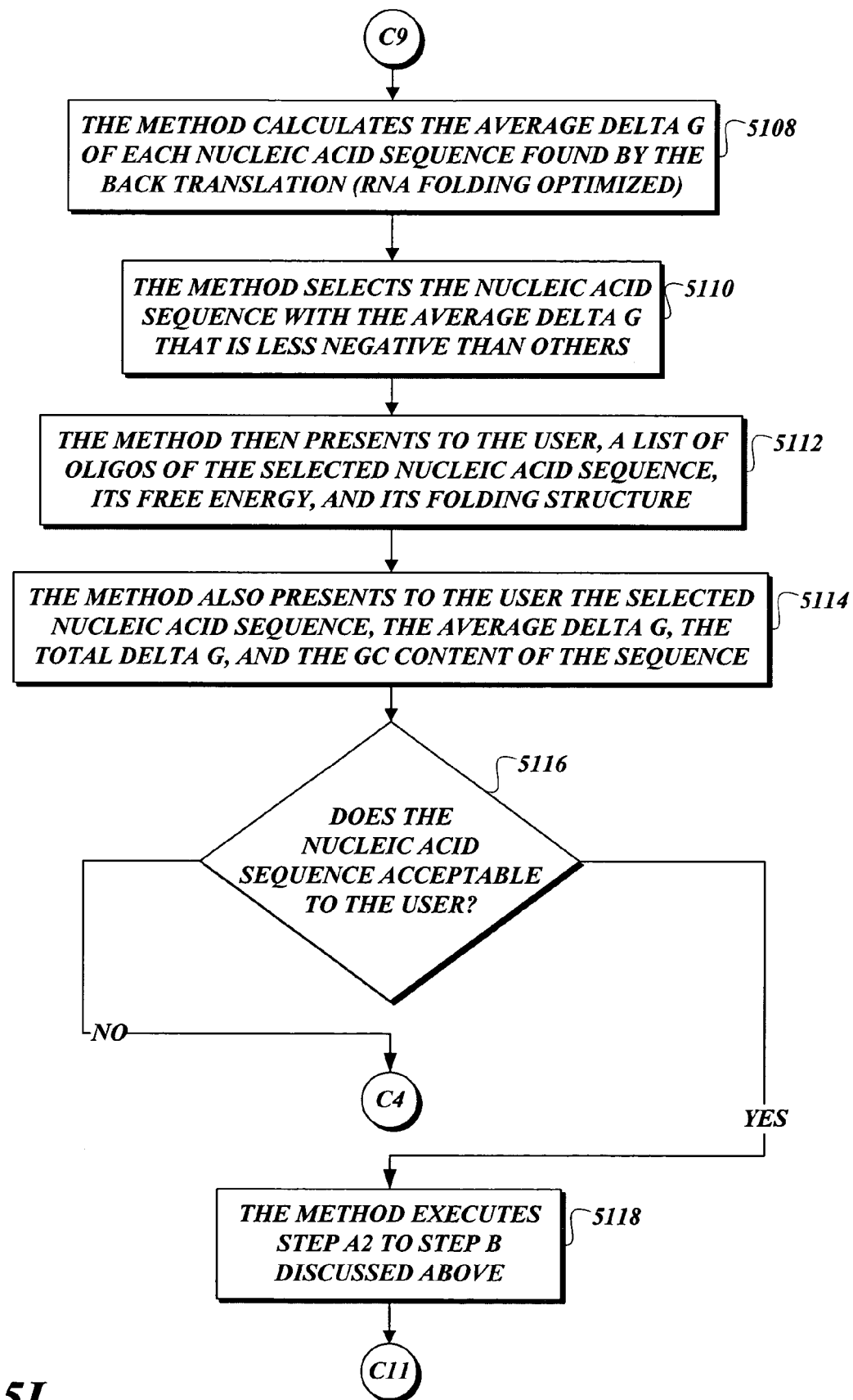

From Terminal C9 (FIG. 5L), the method calculates the average delta g of each nucleic acid sequence found by the back translation (RNA folding optimized). At block 5110, the method selects the nucleic acid sequence with the average delta g that is less negative than others. At block 5112, the method then presents to the user a list of oligonucleotides of the selected nucleic acid sequence, its free energy, and its folding structure. The method also presents to the user the selected nucleic acid sequence, the average delta g, the total delta g, and the GC content of the sequence. See block 5114. At decision block 5116, a test is performed to determine whether the nucleic acid sequence is acceptable to the user. If the answer to the test is No, the method proceeds to Terminal C4 to jump back to decision block 5076 where the above-identified processing steps are repeated. Otherwise, the answer to decision block 5116 is Yes, and the method proceeds to block 5118 where the method executes step A2-step B discussed above. The method then continues to another continuation terminal ("Terminal C11").

Figure 5M:
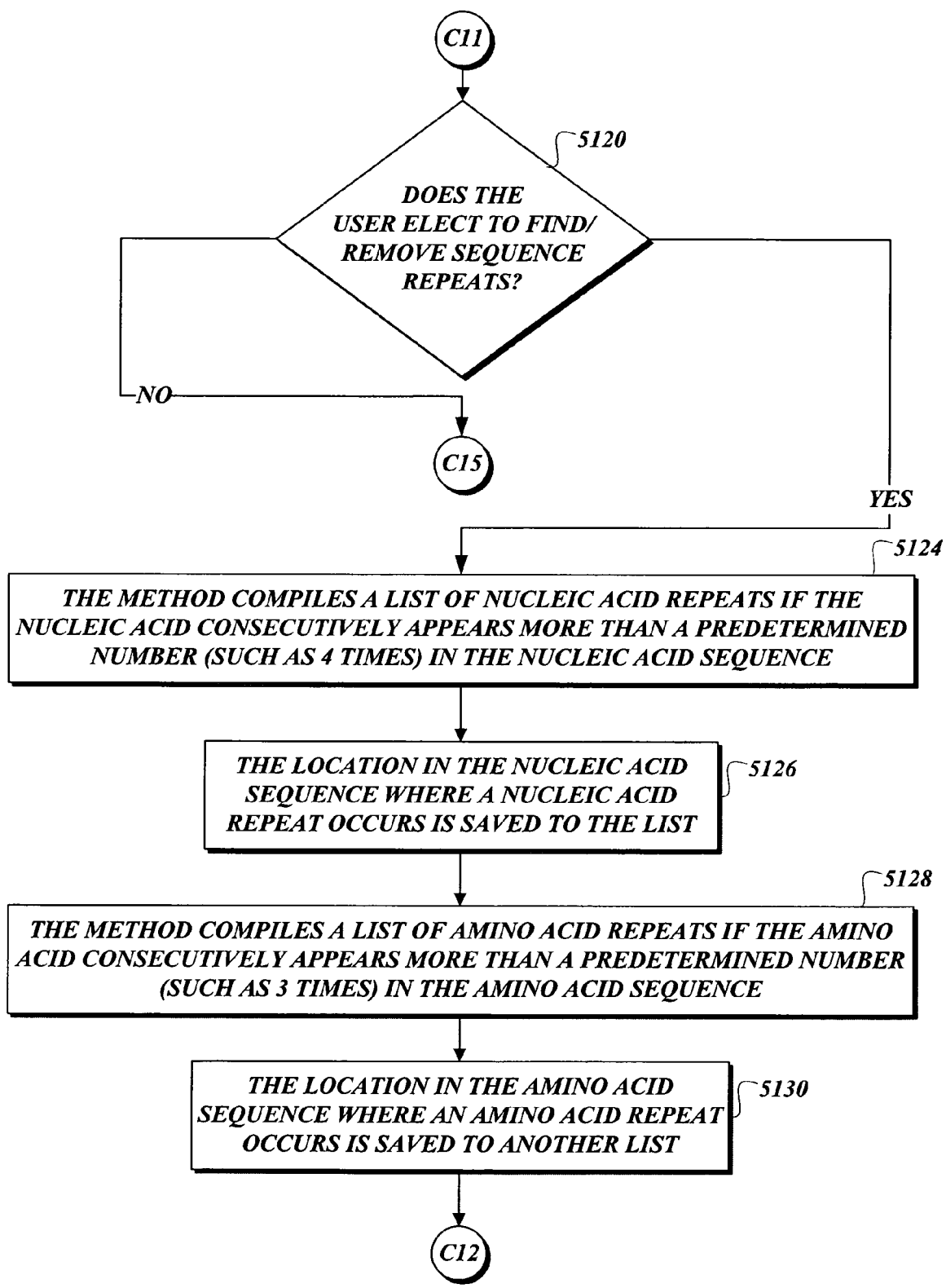

From Terminal C11 (FIG. 5M), the method proceeds to another decision block 5120 where a test is performed to determine whether the user elects to find/remove sequence repeats. If the answer to the test at decision block 5120 is No, the method proceeds to another continuation terminal ("Terminal C15"). Otherwise, the answer to the test at decision block 5120 is Yes, and the method continues to block 5124, where the method compiles a list of nucleic acid repeats if the nucleic acid consecutively appears more than a predetermined number of times (such as four times) in the nucleic acid sequence. At block 5126, the location in the nucleic acid sequence where the nucleic acid repeat occurs is saved to the list. At block 5128, the method compiles a list of amino acid repeats if the amino acid consecutively appears more than a predetermined number of times (such as three times) in the amino acid sequence. At block 5130, the location in the amino acid sequence where an amino acid repeat occurs is saved to another list. The method then continues to another continuation terminal ("Terminal C12").

Figure 5N:
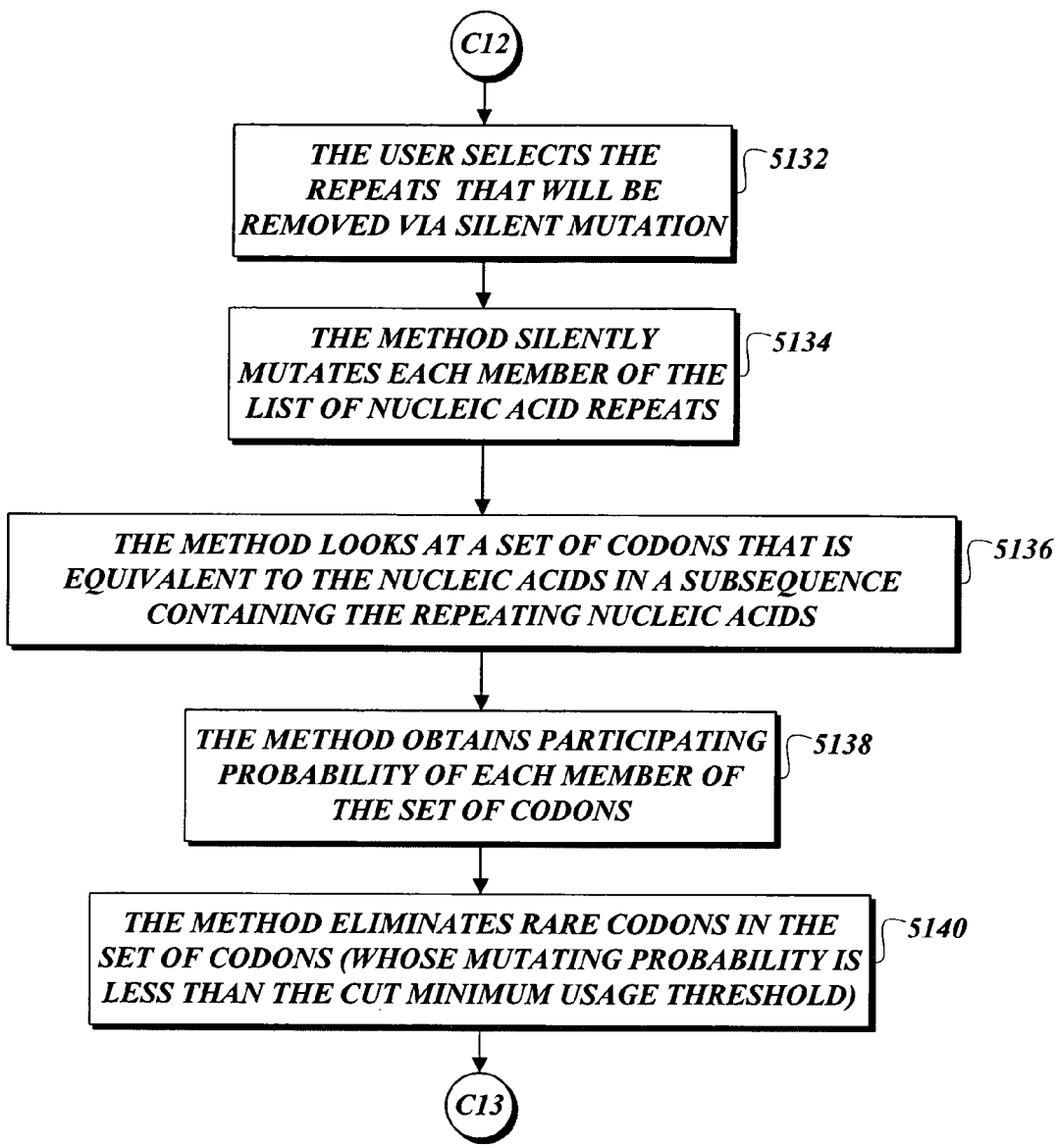
Figure 50:
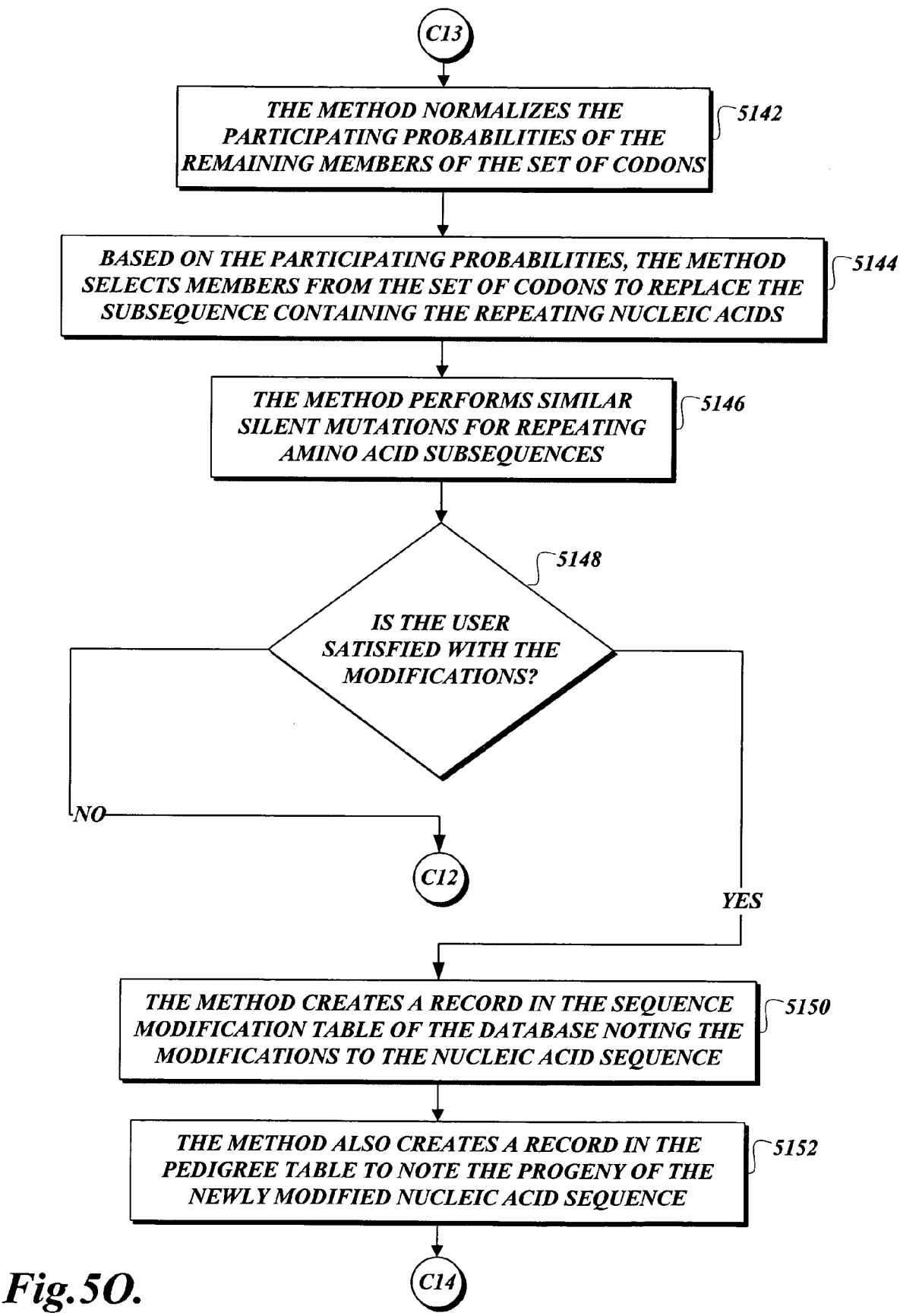

From Terminal C12 (FIG. 5N), the user selects the repeats that would be removed via silent mutations. See block 5132. At block 5134, the method silently mutates each member of the list of nucleic acid repeats. The method looks at a set of codons that is equivalent to the nucleic acids in a subsequence containing the repeating nucleic acids. See block 5136. At block 5138, the method obtains participating probabilities of each member of the set of codons. The method eliminates rare codons in the set of codons (whose mutating probability is less than the cut minimum usage threshold). See block 5140. The method then continues to another continuation terminal ("Terminal C13").

From Terminal C13 (FIG. 5O), the method normalizes the participating probabilities of the remaining members of the set of codons. See block 5142. Next, at block 5144, based on the participating probabilities, the method selects members from the set of codons to replace the subsequence containing the repeating nucleic acids. The method performs similar silent mutations for repeating amino acid subsequences. See block 5146. Next, at decision block 5148, a test is performed to determine whether the user is satisfied with the modification. If the answer to the test at decision block 5148 is No, the method continues to Terminal C12 and jumps back to block 5132 where the above-identified processing steps are repeated. Otherwise, the answer the test at decision block 5148 is Yes, and the method creates a record in the sequence modification table of the databases 114 noting the modifications to the nucleic acid sequence. See block 5150. The method also creates a record (when the user decides to save in the database) in the pedigree table 130 to capture the ancestry of the newly modified nucleic acid sequence and the progeny of the nucleic acid sequence prior to its modifications. See block 5152. The method then continues to another continuation terminal ("Terminal C14").

Figure 5P:
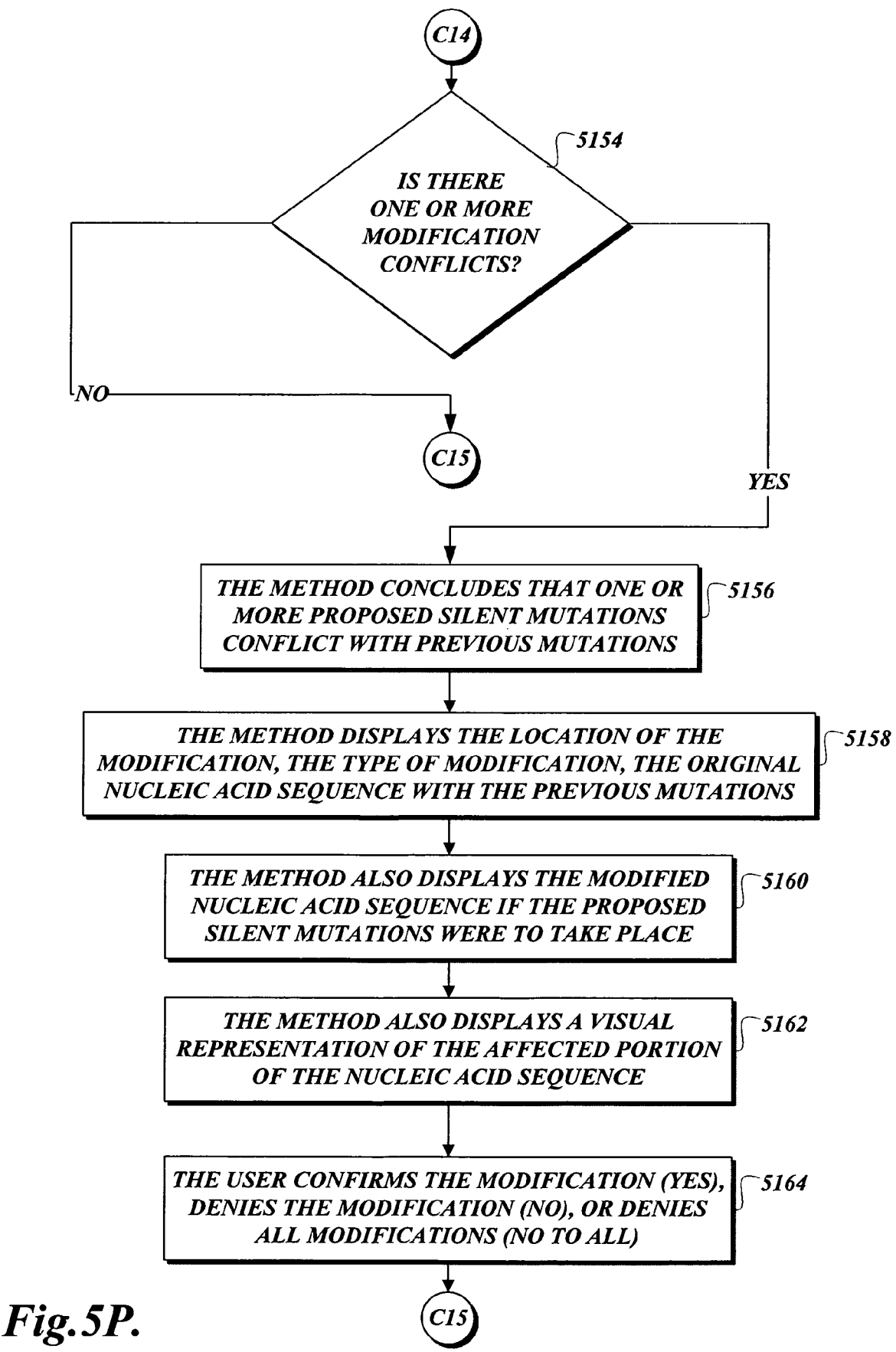

From Terminal C14 (FIG. 5P), the method proceeds to another decision block 5154 where a test is performed to determine whether there are one or more modification conflicts. If the answer to the test at decision block 5154 is No, the method continues to another continuation terminal ("Terminal C15"). Otherwise, the answer to the test at decision block 5154 is Yes, and the method continues to block 5156 where the method concludes that one or more proposed silent mutations conflict with previous mutations. The method displays the location of the modification, the type of modification, and the original nucleic acid sequence with the previous mutations. See block 5158. See also FIG. 4E. The method also displays the modified nucleic acid sequence if the proposed silent mutations were to take place. See block 5160. At block 5162, the method also displays a visual representation of the effective portion of the nucleic acid sequence. The user confirms the modification (Yes), denies the modification (No), or denies all modifications (No to all). See block 5164. The method then continues to Terminal C16.

Figure 5Q:
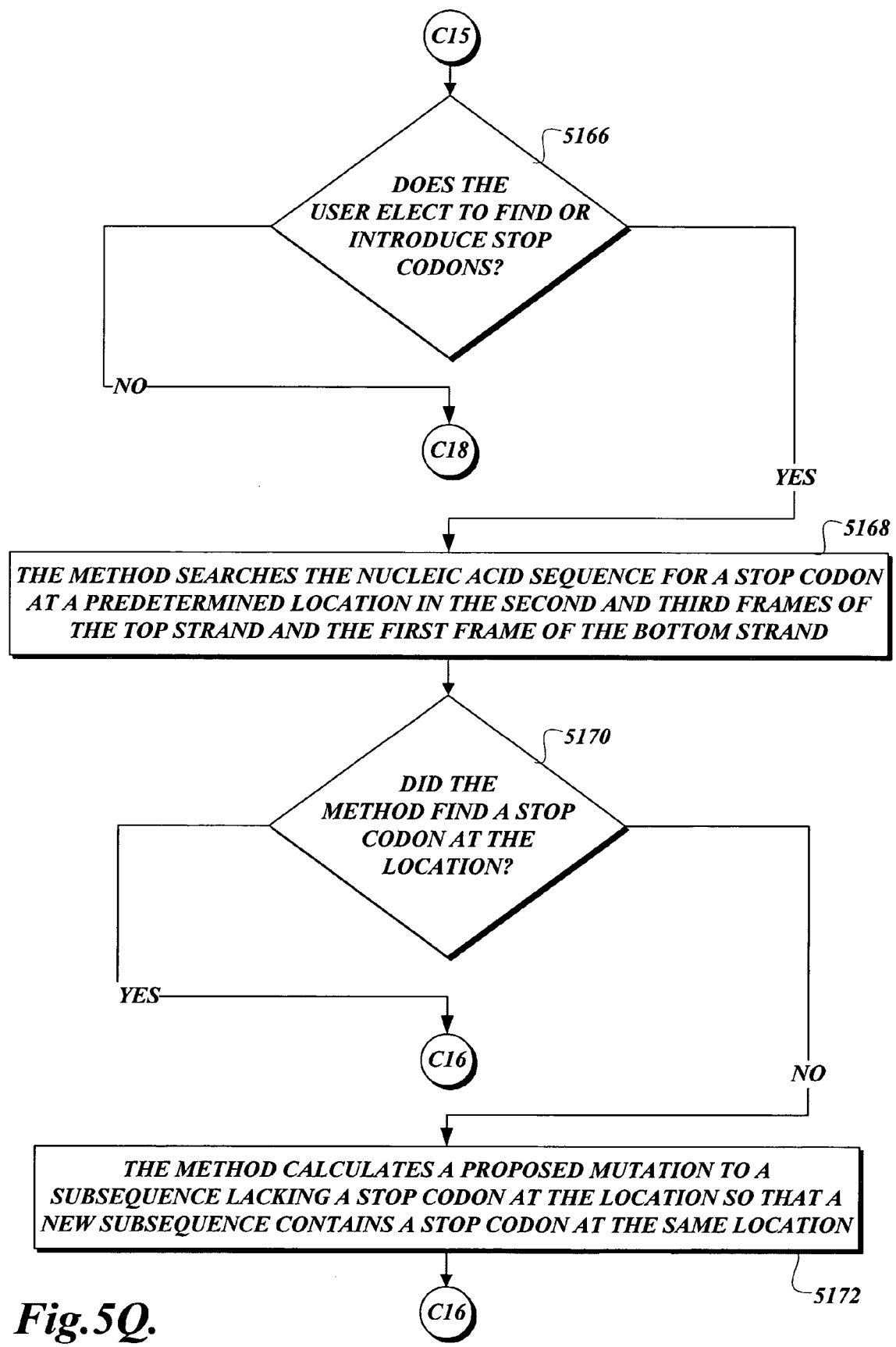

From Terminal C15 (FIG. 5Q), the method proceeds to decision block 5166 where a test is performed to determine whether the user elects to find or introduce stop codons. If the answer to the test at decision block 5166 is No, the method proceeds to another continuation terminal ("Terminal C18"). Otherwise, the method proceeds to block 5168 where the method searches the nucleic acid sequence for a stop codon at a predetermined location in the second and third frames of the top strand and the first frame of the bottom strand. Another test is performed at decision block 5170 to determine whether the method finds a stop codon at the location. If the answer to the test at decision block 5170 is Yes, the method proceeds to another continuation terminal ("Terminal C16"). Otherwise, the answer to the test at decision block 5170 is No, and the method proceeds to block 5172 where the method calculates a proposed silent mutation to a subsequence lacking a stop codon at the location so that a new subsequence contains a stop codon at the same location. See block 5172. The method then continues to Terminal C16.

Figure 5R:
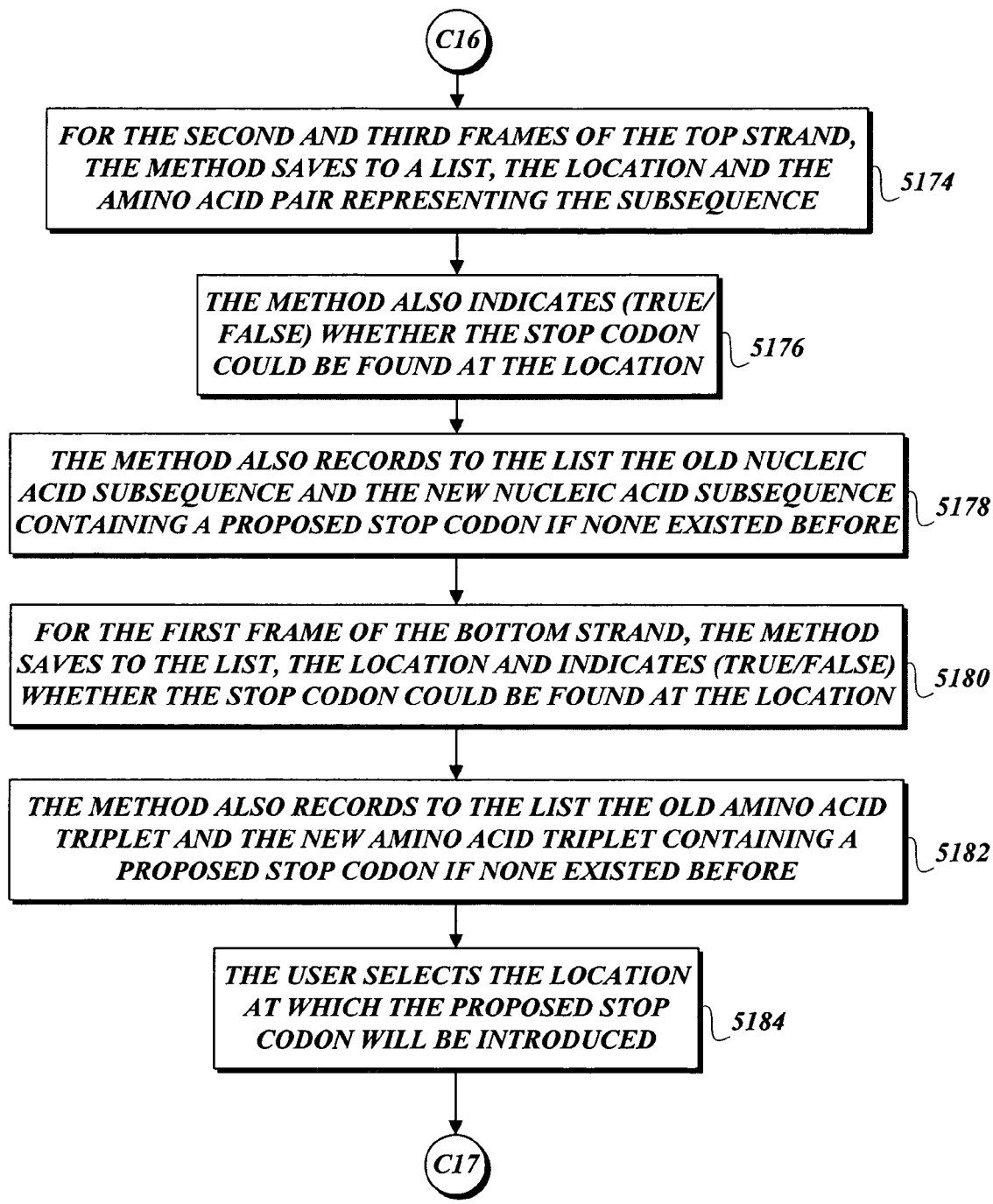

From Terminal C16 (FIG. 5R), for the second and third frames of the top strand, the method saves to a list the location and the amino acid pair representing the subsequence. See block 5174. At block 5176, the method also indicates (True or False) whether the stop codon could be found at the location. The method also records to the list the old nucleic acid subsequence and the new nucleic acid subsequence containing a proposed stop codon if none existed before. See block 5178. At block 5180, for the first frame of the bottom strand, the method saves to the list the location and indicates (True or False) whether the stop codon could be found at the location. At block 5182, the method also records to the list the old amino acid triplet and the new amino acid triplet containing a proposed stop codon if none existed before. The method then continues to block 5184 where the user selects the location at which the proposed stop codon will be introduced. The method then continues to another continuation terminal ("Terminal C17").

Figure 5S:
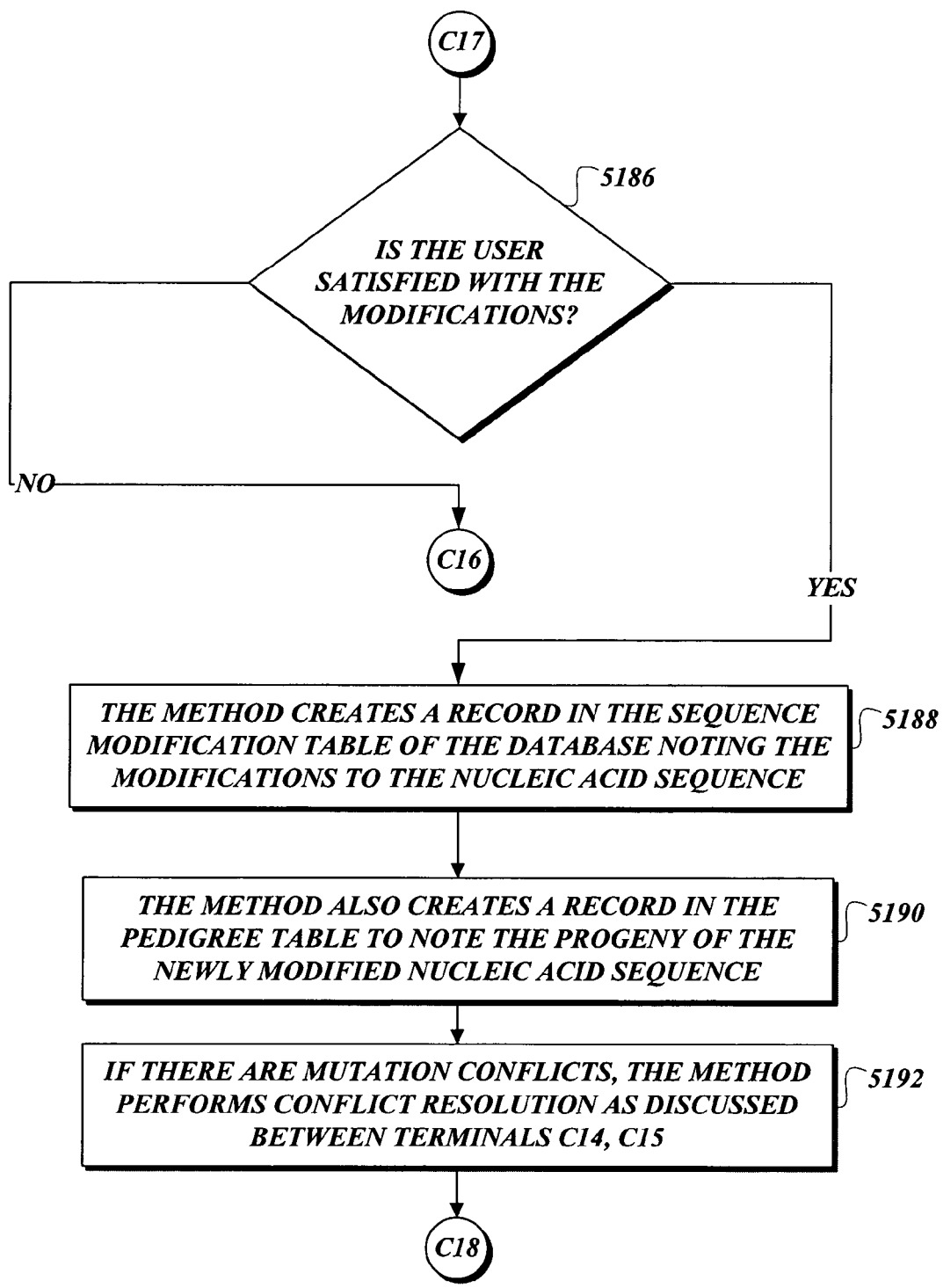

From Terminal C17 (FIG. 5S), a test is performed at decision block 5186 to determine whether the user is satisfied with the modifications. If the answer to the test at decision block 5186 is No, the method continues to Terminal C16 and loops back to block 5174 where the above-identified processing steps are repeated. If the answer to the test at decision block 5186 is Yes, the method continues to block 5188 where the method creates a record in the sequence modification table of the database noting modifications to the nucleic acid sequence. The method also creates a record in the pedigree table to note the progeny of the newly modified nucleic acid sequence. See block 5190. At block 5192, if there are mutations conflicts, the method performs conflict resolution as discussed between Terminals C14, C15. The method then continues to another continuation terminal ("Terminal C18").

Figure 5T:
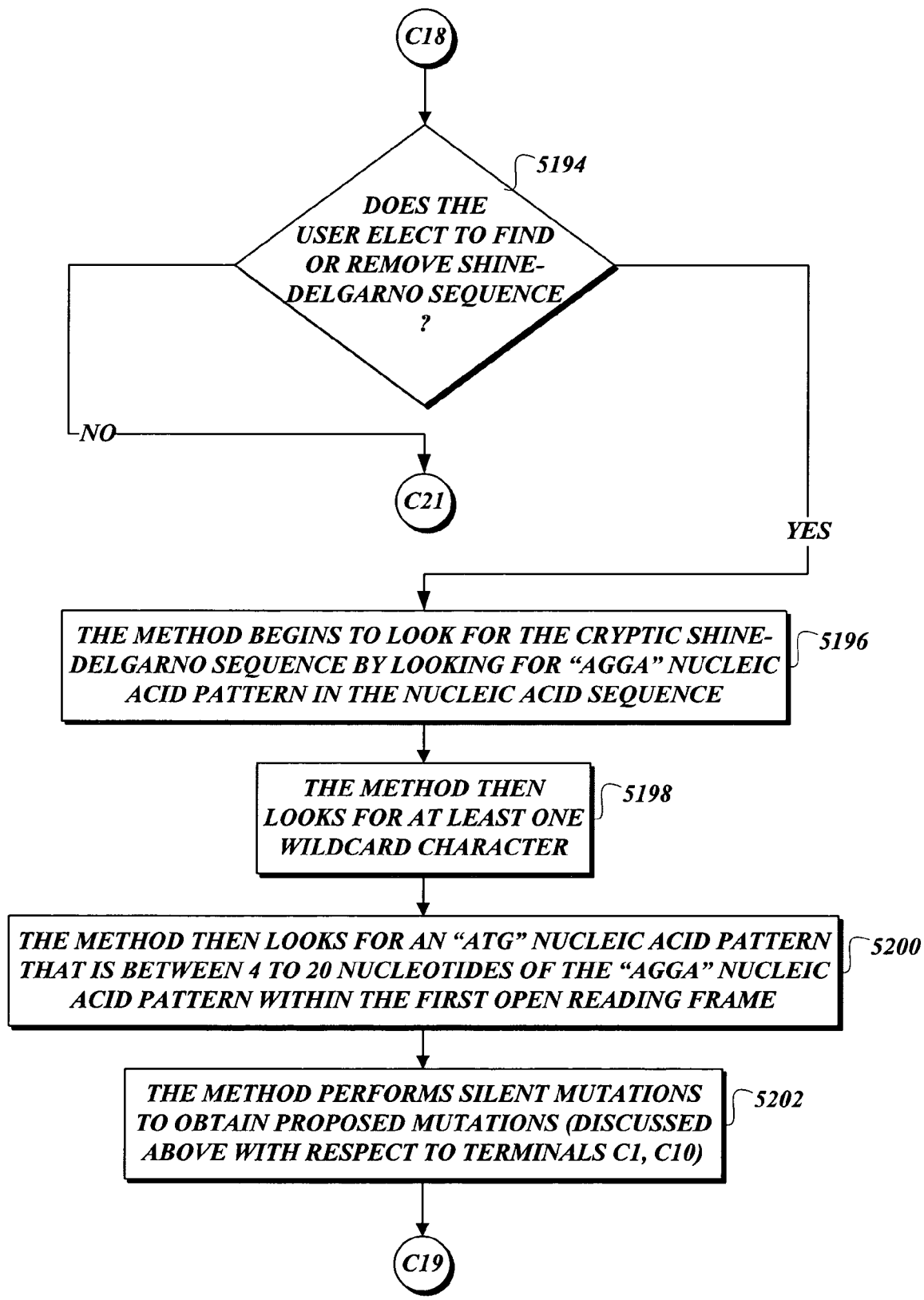

From Terminal C18 (FIG. 5T), the method proceeds to decision block 5194 where a test is performed to determine whether the user elects to find or remove Shine-Delgarno sequences. If the answer to the test at decision block 5194 is No, the method continues to another continuation terminal ("Terminal C21"). Otherwise, the answer to the test at decision block 5194 is Yes, and the method proceeds to block 5196 where the method proceeds the cryptic Shine-Delgarno sequence by looking for the "AGGA" nucleic acid pattern in the nucleic acid sequence. At block 5198, the method then looks for at least one wild card character. The method then looks for an "ATG" nucleic acid pattern that is between 4-20 nucleotides of the "AGGA" nucleic acid pattern within the first open reading frame. See block 5200. At block 5202, the method performs silent mutations to obtain proposed mutations (discussed above with respect to Terminals C1, C10). The method then continues to another continuation terminal ("Terminal C19").

Figure 5U:
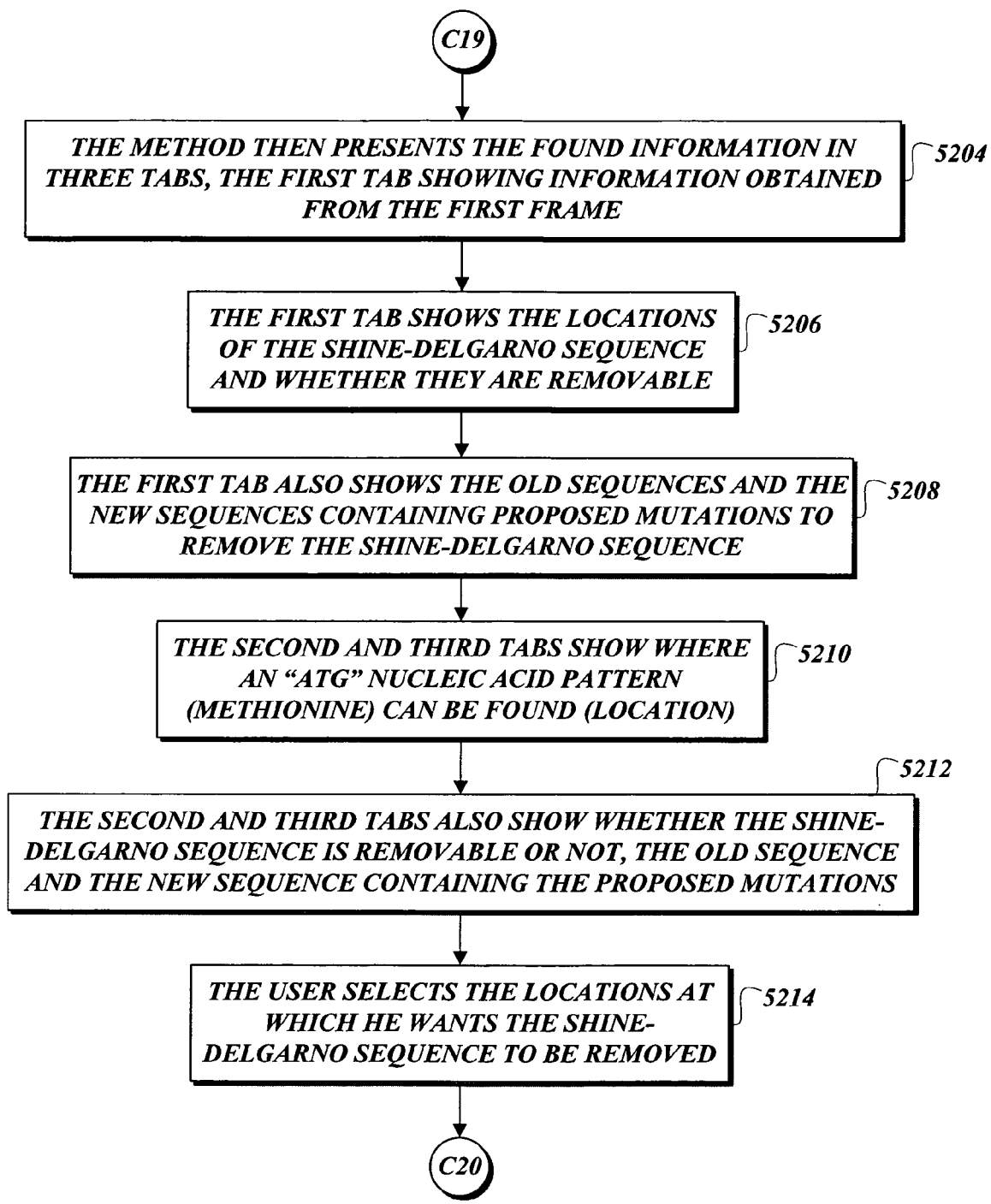

From Terminal C19 (FIG. 5U), the method then presents the found information in three tabs, the first tab showing information obtained from the first frame. See block 5204. At block 5206, the first tab shows the locations of the Shine-Delgarno sequence and whether they are removable. The first tab also shows the old sequences and the new sequences containing proposed mutations to remove the Shine-Delgarno sequence. See block 5208. At block 5210, the second and third tabs show where an "ATG" nucleic acid pattern (methionine) can be found (at a particular location). See block 5210. At block 5212, the second and third tabs also show whether the Shine-Delgarno sequence is removable or not, the old sequence and the new sequence containing the proposed mutations. The method then proceeds to block 5214 where the user selects the locations at which he wants the Shine-Delgarno sequence to be removed. The method then continues to another continuation terminal ("Terminal C20").

Figure 5V:
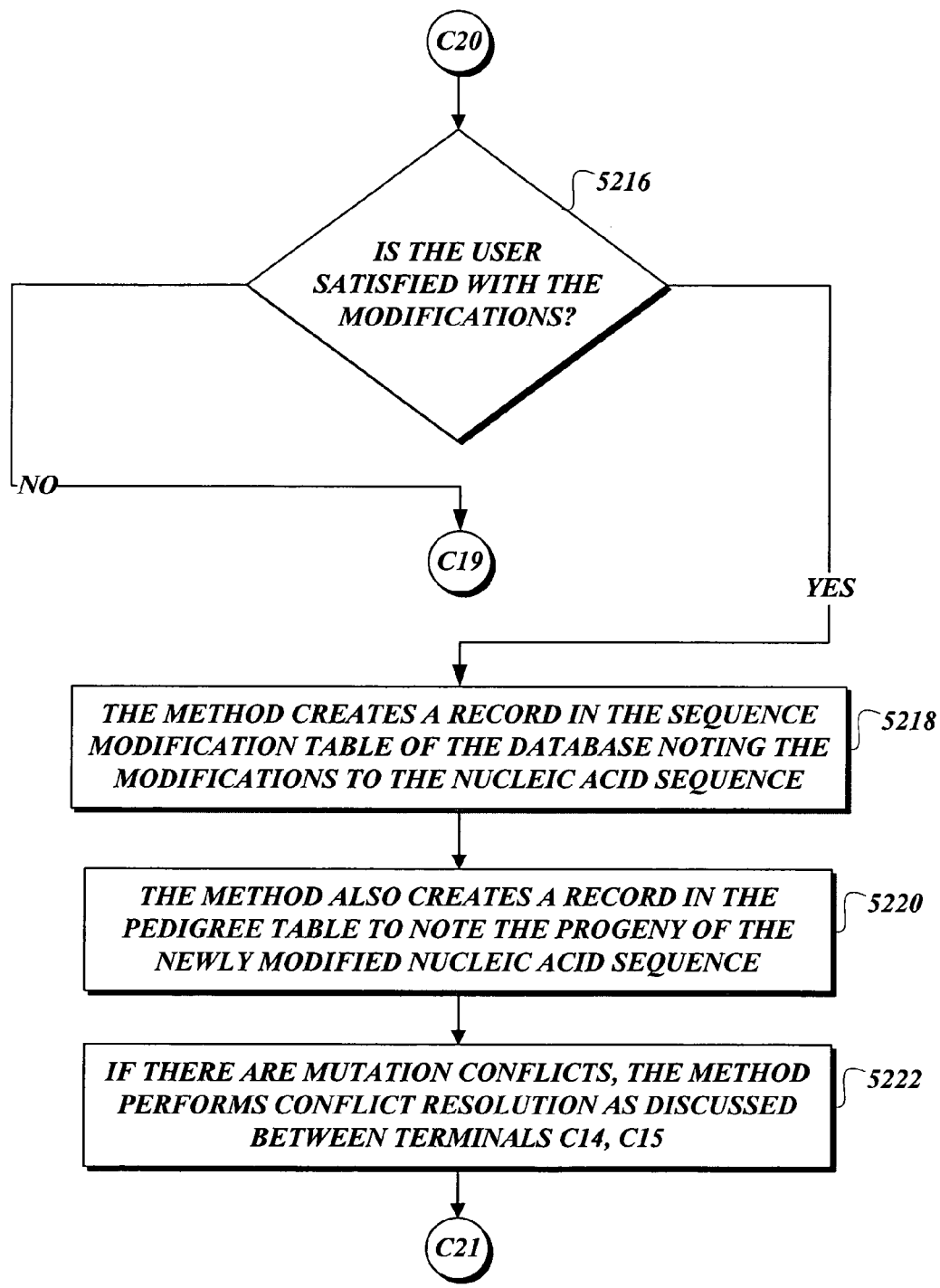

From Terminal C20 (FIG. 5V), a test is performed at decision block 5216 to determine whether the user is satisfied with the modifications. If the answer to the test at decision block 5216 is No, the method continues to Terminal C19. Otherwise, the answer to the test at decision block 5216 is Yes, and the method creates a record in the sequence modification table of the database noting the modifications to the nucleic acid sequence. See block 5218. The method also creates a record in the pedigree table to note the progeny of the newly modified nucleic acid sequence. See block 5220. If there are mutation conflicts, the method also performs conflict resolution as discussed between Terminals C14, C15. See block 5222. The method then continues to another continuation terminal ("Terminal C21").

Figure 5W:
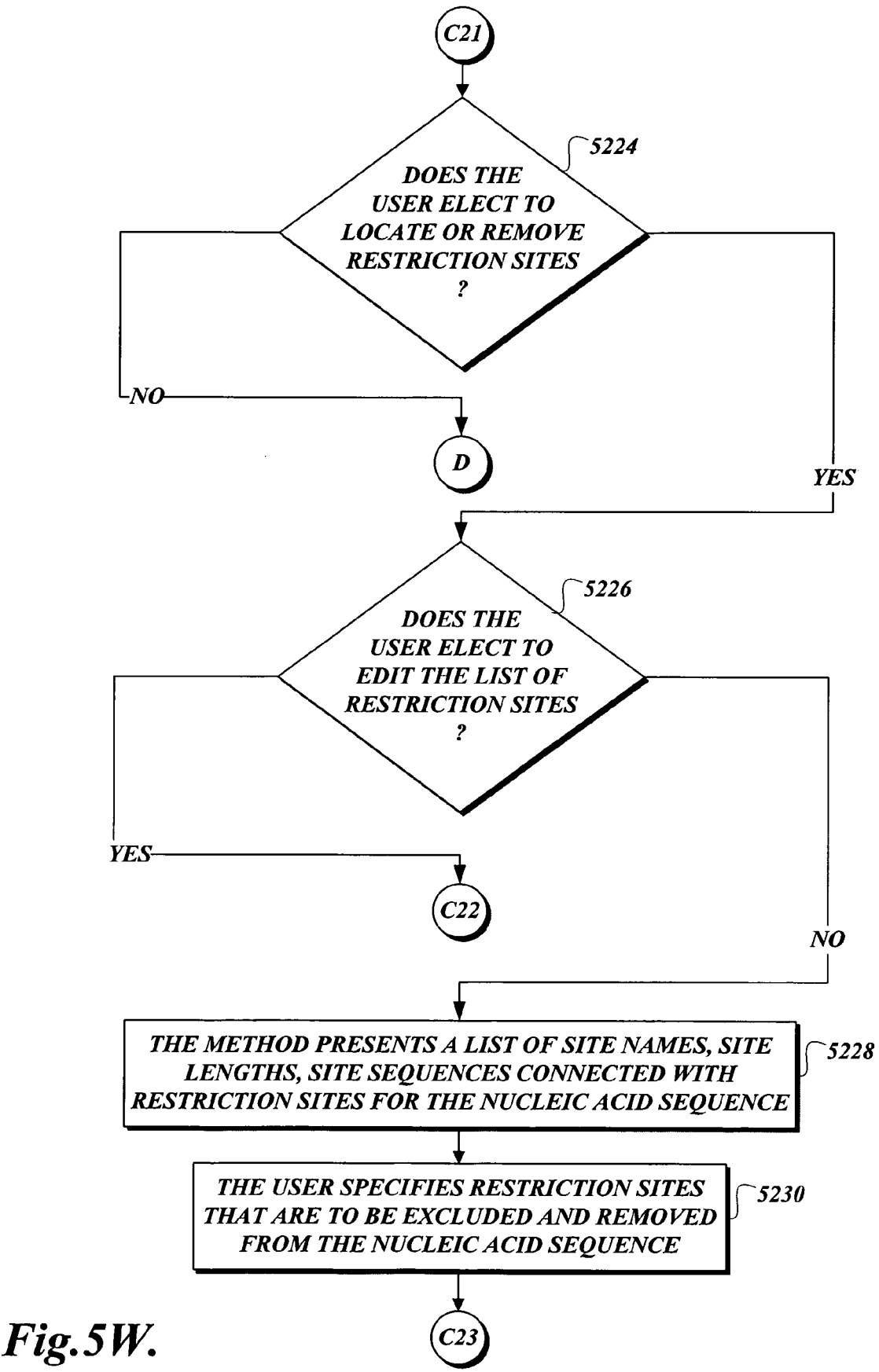

From Terminal C21 (FIG. 5W), a decision block 5224 is entered by the method where a test is performed to determine whether the user elects to locate or remove a restriction site. If the answer to the test at decision block 5224 is No, the method continues to exit Terminal D. Otherwise, the answer to the test at decision block 5224 is Yes, and the method continues to another decision block 5226 where another test is performed to determine whether the user elects to edit the list of restriction sites. If the answer to the test at decision block 5226 is Yes, the method continues to another continuation terminal ("Terminal C22"). Otherwise, the answer is No to the test at decision block 5226, and the method proceeds to block 5228 where the method presents a list of site names, site lengths, and site sequences connected with restriction sites for the nucleic acid sequence. At block 5230, the user specifies restriction sites that are to be excluded and removed from the nucleic acid sequence. The method then continues to another continuation terminal ("Terminal C23").

Figure 5X:
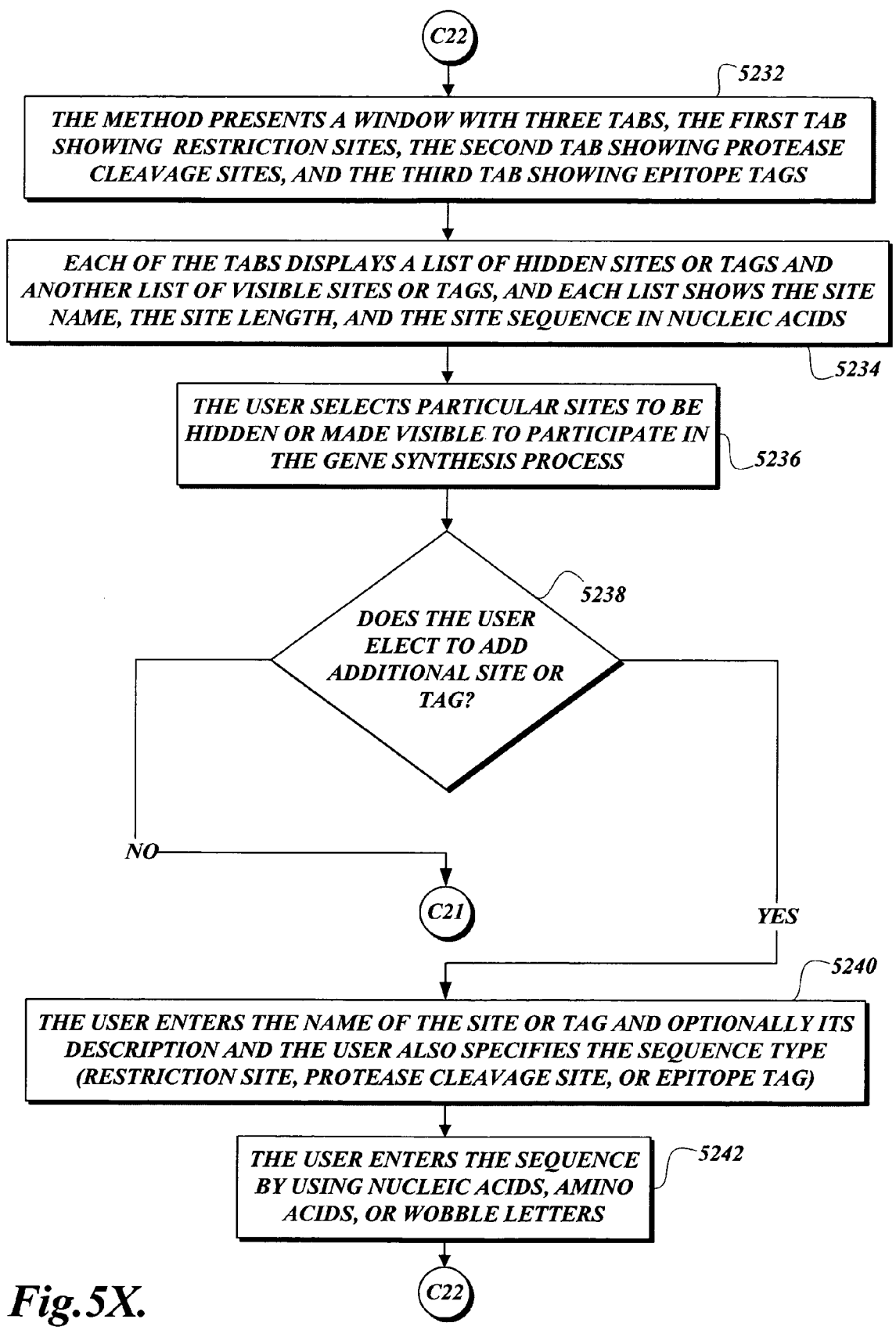

From Terminal C22 (FIG. 5X), the method presents a window with three tabs, the first tab showing restriction sites, the second tab showing protease cleavage sites, and the third tab showing epitope tags. See block 5232. Each of the tabs displays a list of hidden sites or tags and another list of visible sites or tags, and each list shows the site name, the site length, and the site sequence in nucleic acids. See block 5234. The user selects a particular site to be hidden or made visible to participate in the gene synthesis process. At decision block 5238, a test is performed to determine whether the user elects to add an additional site or tag. If the answer is No to the test at decision block 5238, the method continues to Terminal C21 and jumps back to decision block 5224 where the above-identified processing steps are repeated. Otherwise, the answer to the test at decision block 5238 is Yes, and the method proceeds to block 5240 where the user enters the name of the site or tag, and optionally its description, and the user also specifies the sequence type (restriction site, protease cleavage site, or epitope tag). At block 5242, the user enters the sequence by using nucleic acids, amino acids, or wobble letters. The method then continues to Terminal C21 and loops back to block 5232 where the above-identified processing steps are repeated.

Figure 5Y:
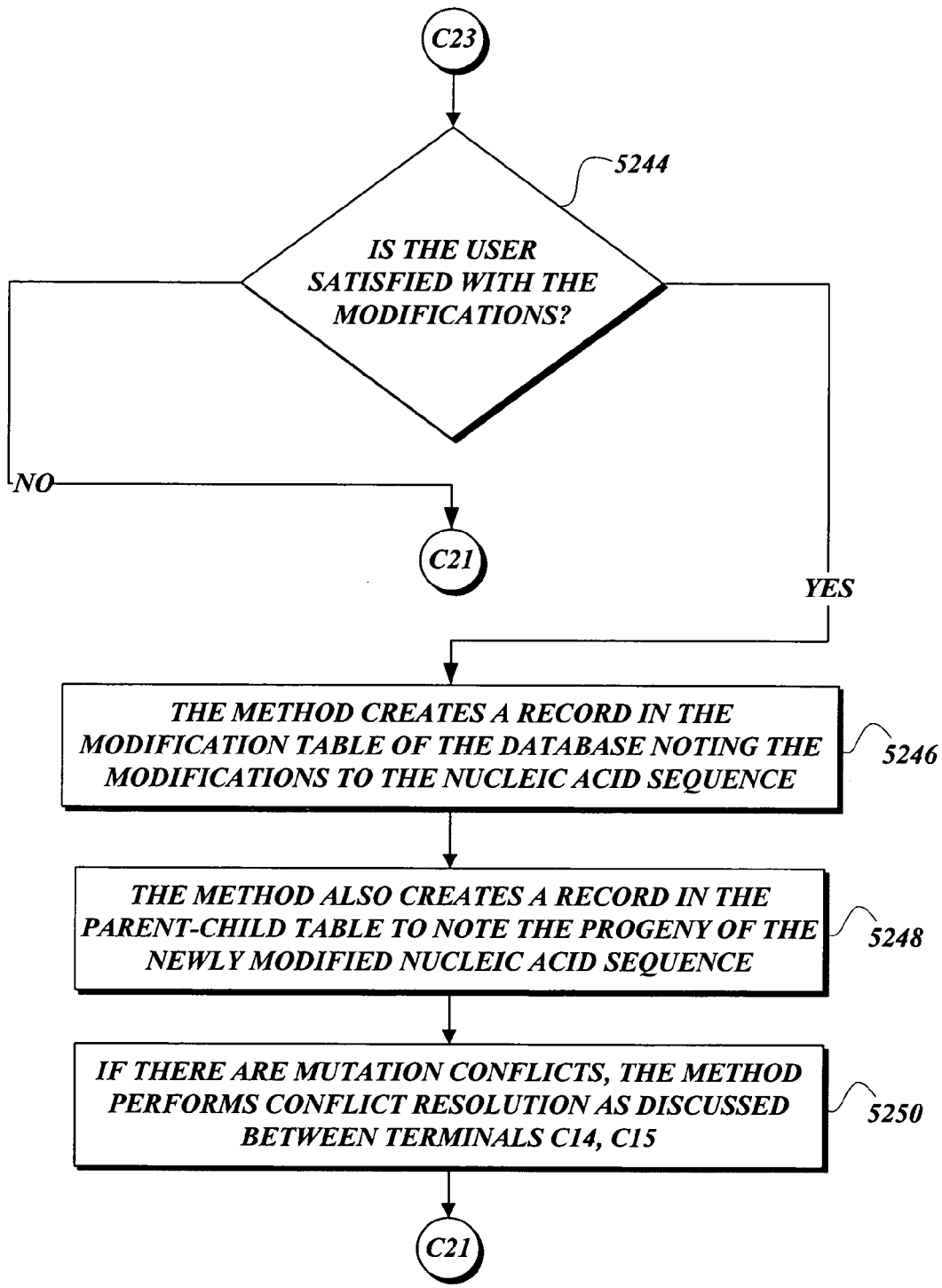
Figure 5Z:
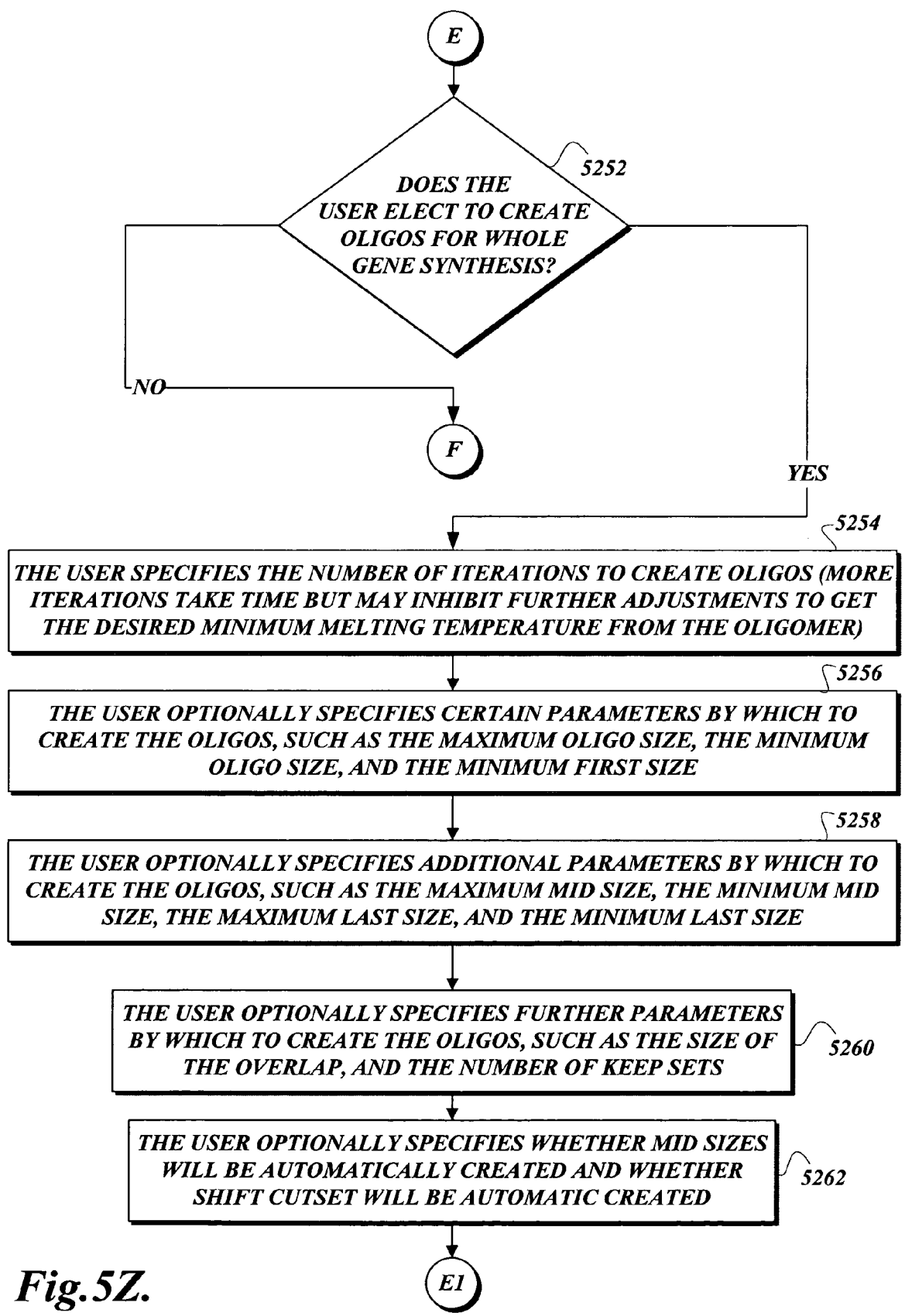
Figure 5A:
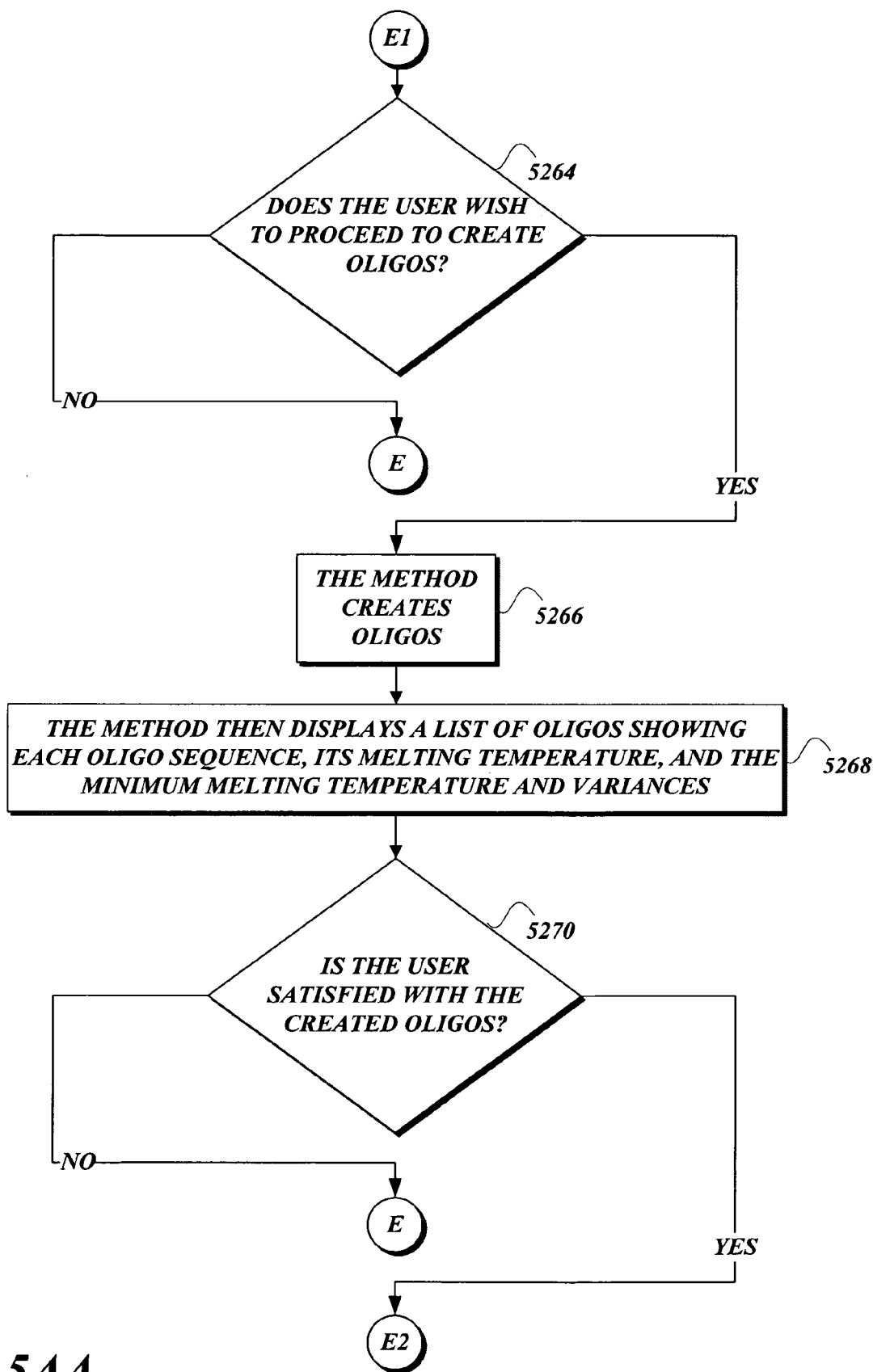
Figure 5A:
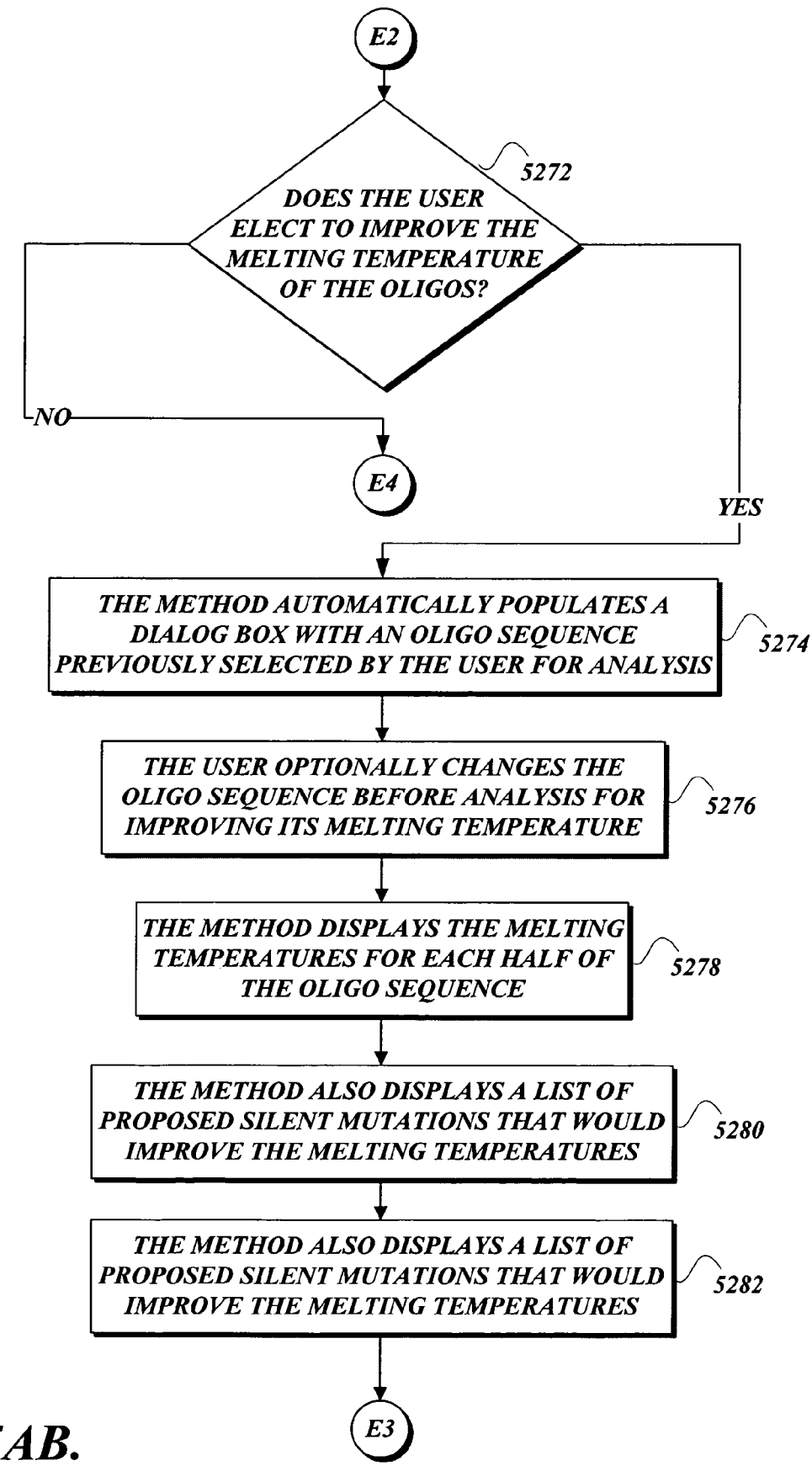
Figure 5A:
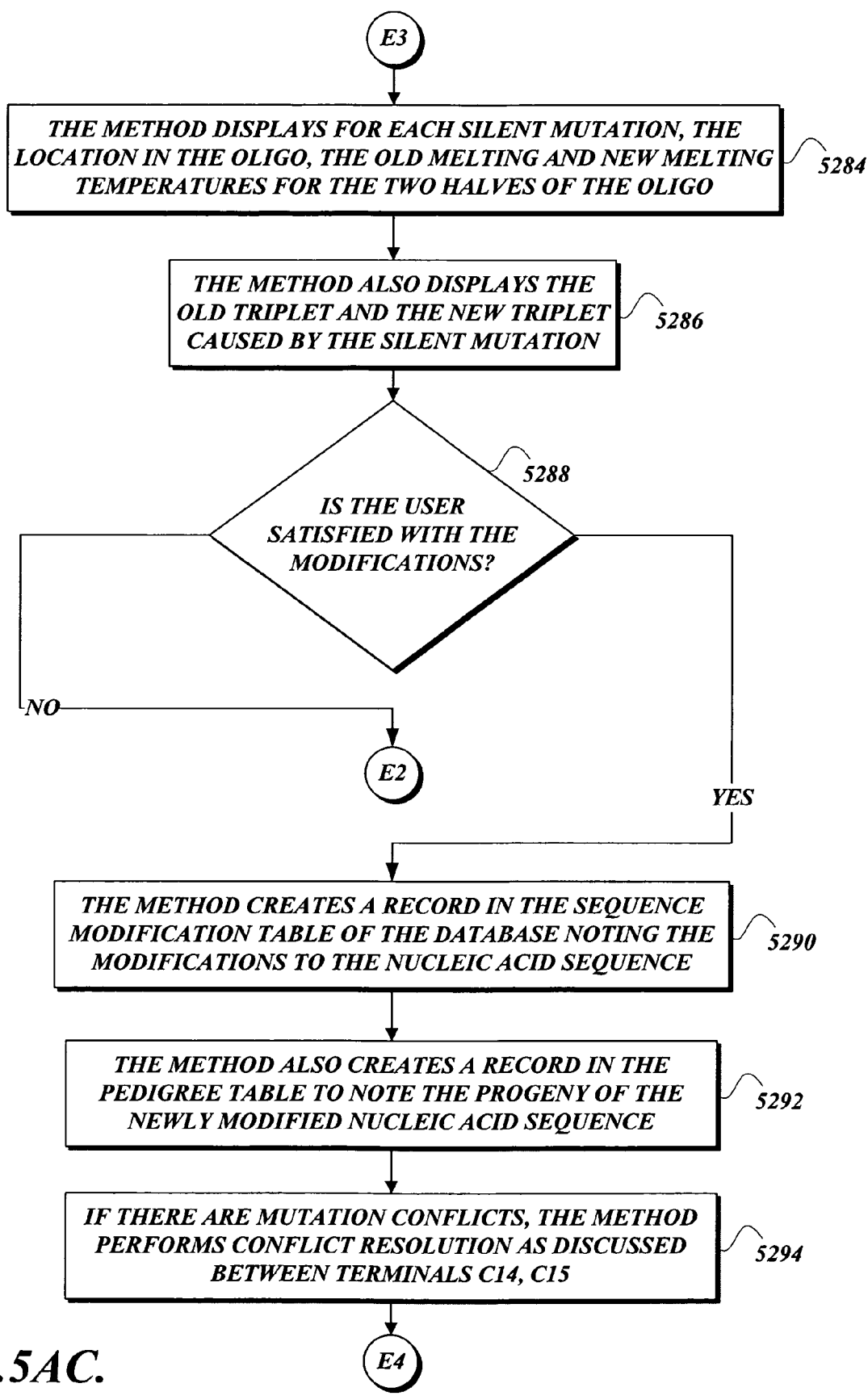
Figure 5A:
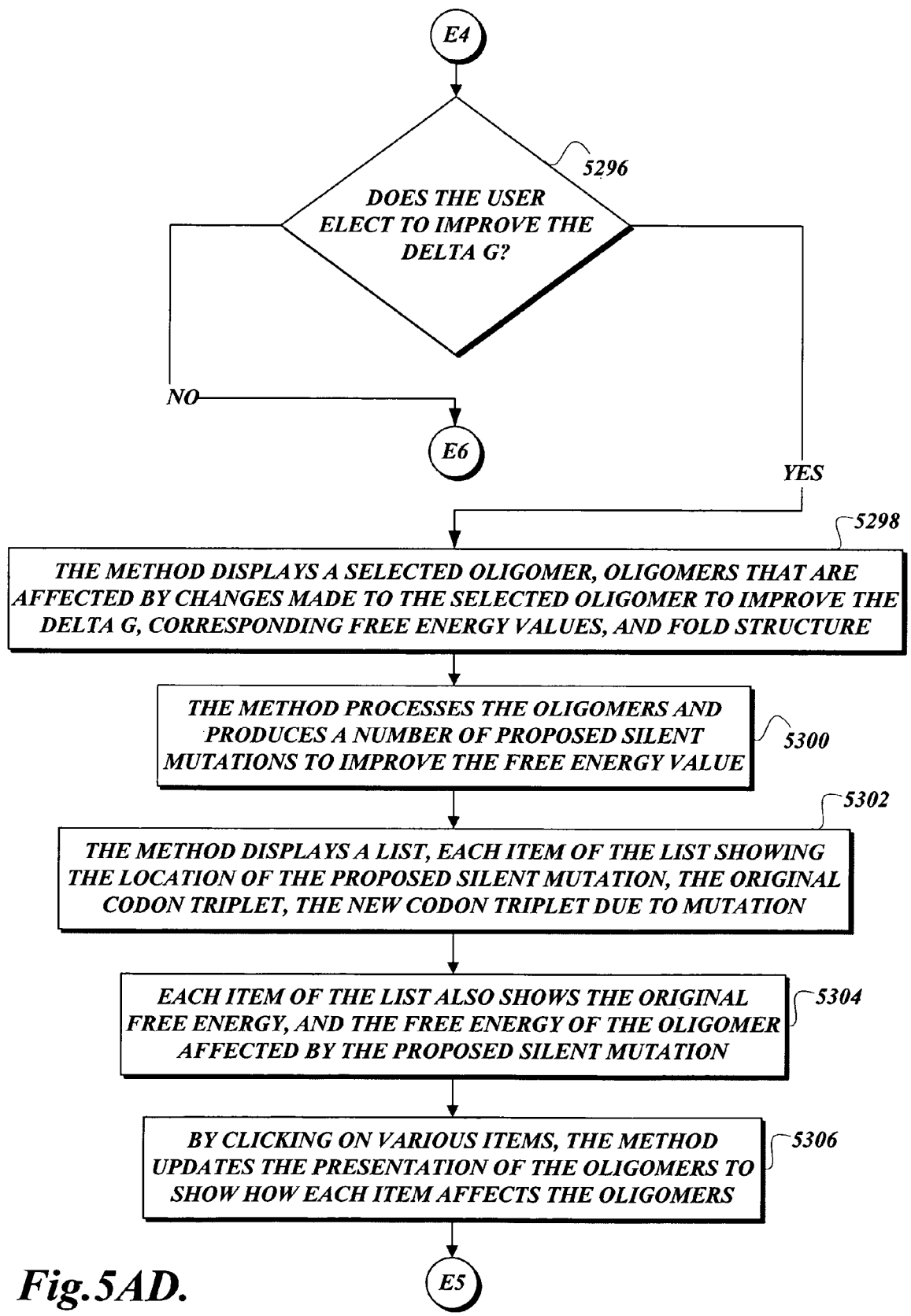
Figure 5A:
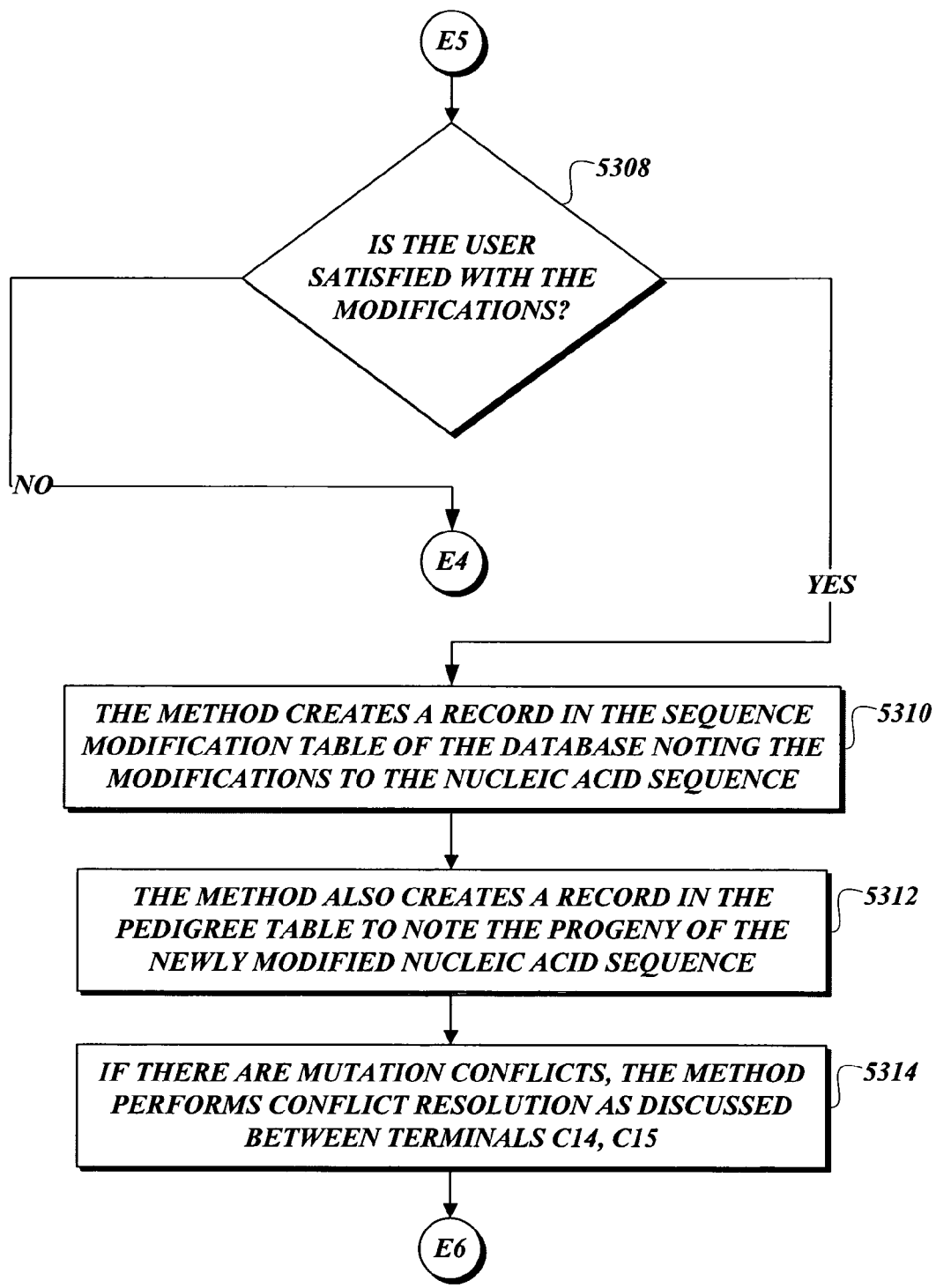
Figure 5A:
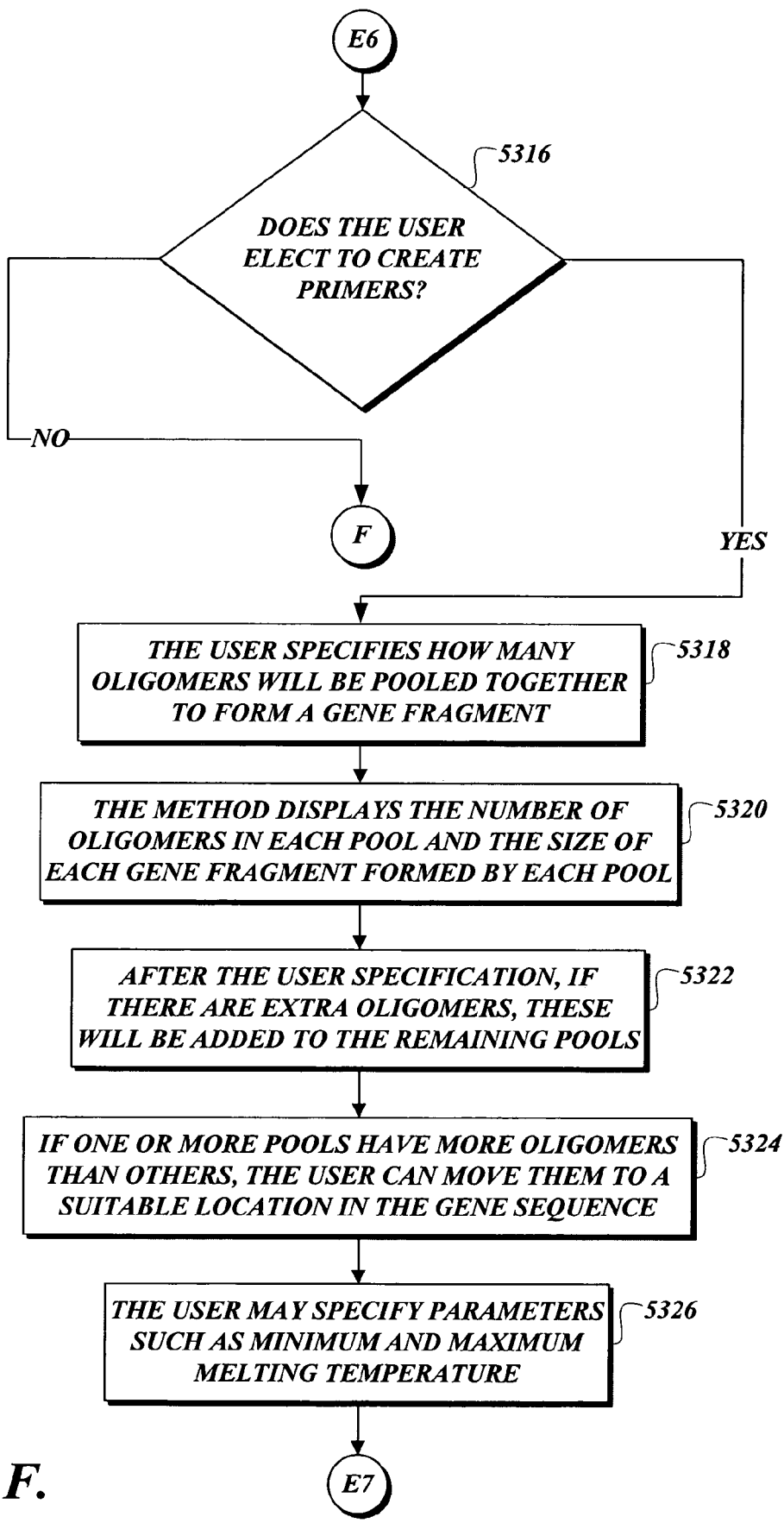
Figure 5A:
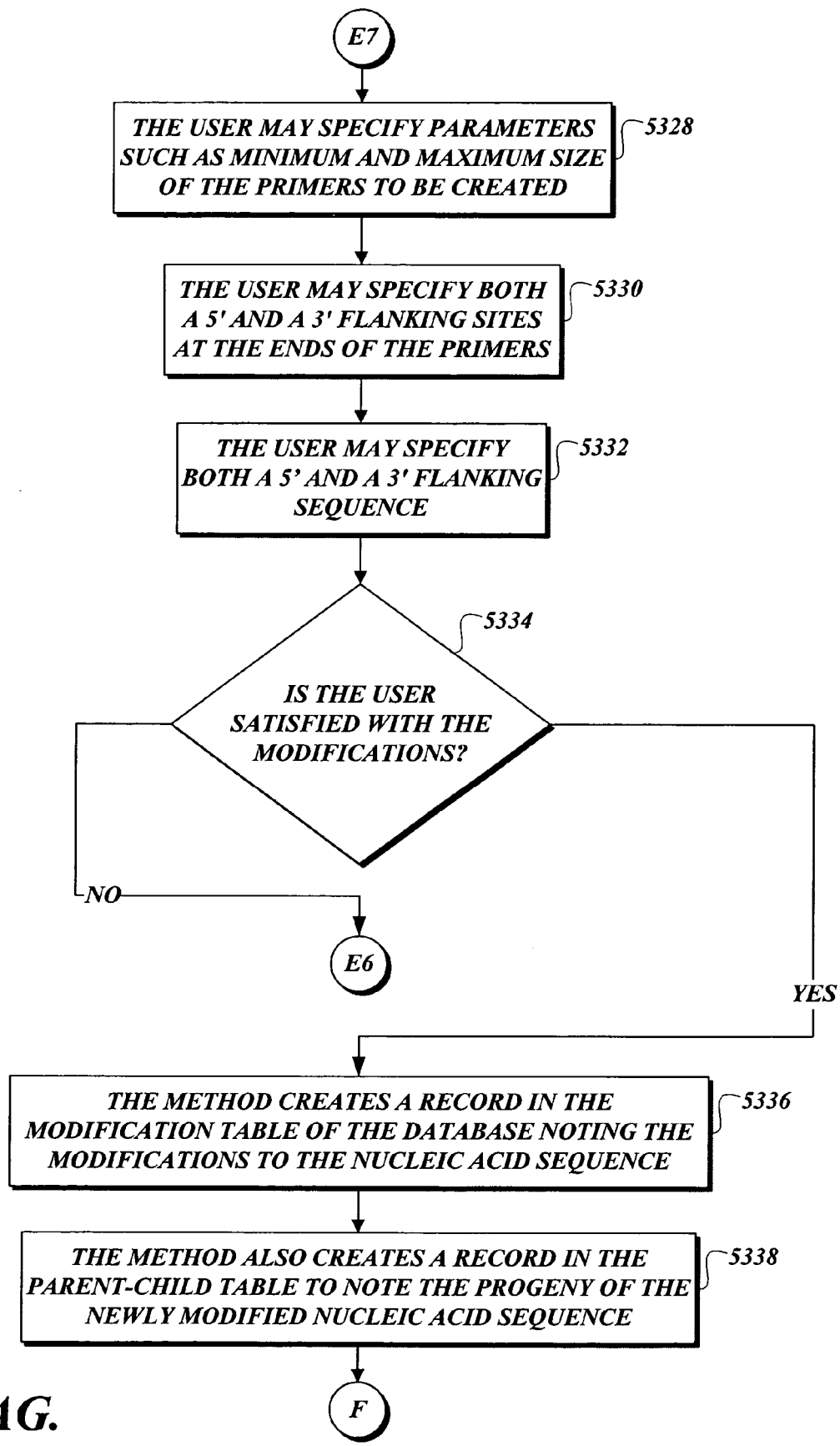

From Terminal C23 (FIG. 5Y), the method proceeds to decision block 5244 where a test is performed to determine whether the user is satisfied with the modifications. If the answer to the test at decision block 5244 is No, the method continues to Terminal C21 and jumps back to decision block 5224 where the above-identified processing steps are repeated. Otherwise, the answer to the test at decision block 5244 is Yes, and the method proceeds to block 5246 where the method creates a record in the sequence modification table of the databases 114 noting the modifications of the nucleic acid sequence. At block 5248, the method also creates a record in the pedigree table to note the progeny of the newly modified nucleic acid sequence. If there are mutation conflicts, the method performs conflict resolution as discussed between Terminals C14, C15. See block 5250. The method then continues to Terminal C21 and loops back to decision block 5224 where the above-identified processing steps are repeated.

From Terminal D (FIG. 5A), the method 5000 proceeds to a set of method steps 5006 defined between a continuation terminal ("Terminal E") and an exit terminal ("Terminal F"). From Terminal E, the method proceeds to decision block 5252 where a test is performed to determine whether the user elects to create oligonucleotides for whole gene synthesis. If the answer to the test at decision block 5252 is No, the method continues to exit Terminal F and terminates execution. Otherwise, the answer to the test at decision block 5252 is Yes, and the method proceeds to block 5254 where the user specifies the number of iterations to create oligonucleotides (more iterations take time but may inhibit further adjustments to get the desired minimum melting temperature). At block 5256, the user optionally specifies certain parameters by which to create the oligonucleotides, such as the maximum oligonucleotide size, the minimum oligonucleotide size, and the minimum first size. At block 5258, the user may optionally specify additional parameters by which to create the oligonucleotides, such as the maximum mid size, minimum mid size, the maximum last size, and the minimum last size. At block 5260, the user optionally specifies further parameters by which to create the oligonucleotides, such as the size of the overlap, and the number of keep sets. The user optionally specifies whether mid sizes would be automatically created and whether shift cut sets would be automatically created at block 5262. The method then continues to another continuation terminal ("Terminal E1").

From Terminal E1 (FIG. 5AA), the method proceeds to decision block 5264 where a test is performed to determine whether the user wishes to proceed to create oligonucleotides. If the answer to the test at decision block 5264 is No, the method continues to Terminal E and loops back to decision block 5252, where the above-identified processing steps are repeated. Otherwise, the answer to the test at decision block 5264 is Yes, and the method proceeds to block 5266 where the method creates oligonucleotides. The method then displays a list of oligonucleotides showing each oligonucleotide sequence, its melting temperature, and the minimum melting temperature and variances. See block 5268. At decision block 5270, a test is performed to determine whether the user is satisfied with the created oligonucleotides. If the answer to the test at decision block 5270 is No, the method proceeds to Terminal E and loops back to decision block 5252 where the above-identified processing steps are repeated. Otherwise, the answer to the test at decision block 5270 is Yes, and the method proceeds to another continuation terminal ("Terminal E2").

From Terminal E2, the method proceeds to another decision block 5272 where a test is performed to determine whether the user elects to improve the melting temperature of the oligonucleotides. If the answer to the test at decision block 5272 is No, the method proceeds to another continuation terminal ("Terminal E4"). If the answer to the test at decision block 5272 is Yes, the method automatically populates a dialog box with an oligo sequence previously selected by the user for analysis. See block 5274. The user optionally may change the oligo sequence before analysis for improving its melting temperature. See block 5276. The method displays the melting temperatures for each half of the oligonucleotide sequence. See block 5278. At block 5280, the method also displays a list of proposed silent mutations that would improve the melting temperatures. The method then continues to another continuation terminal ("Terminal E3").

From Terminal E3 (FIG. 5AC), the method displays, for each silent mutation, the location in the oligonucleotide, and the old melting and new melting temperatures for the two halves of the oligonucleotide. See block 5284. The method also displays the old triplet and the new triplet caused by the silent mutation. See block 5286. A test is performed at decision block 5288 to determine whether the user is satisfied with the modifications. If the answer to the test at decision block 5288 is No, the method continues to Terminal E2 and loops back to decision block 5272 where the above-identified processing steps are repeated. Otherwise, the method proceeds to block 5290 where the method creates a record in the sequence modification table of the database, noting the modifications to the nucleic acid sequence. See block 5290. The method also creates a record in the pedigree table to note the progeny of the newly modified nucleic acid sequence. See block 5292. If there are mutations conflicts, the method performs conflict resolution as discussed between Terminals C14, C15. See block 5294. The method then continues to another continuation terminal ("Terminal E4").

From Terminal E4 (FIG. 5AD), the method proceeds to decision block 5296 where a test is performed to determine whether the user has elected to improve the delta g. If the answer is No to the test at decision block 5296, the method proceeds to a continuation terminal ("Terminal E6"). If the answer to the test at decision block 5296 is Yes, the method continues to block 5298 where the method displays a selected oligonucleotide, oligonucleotides that are affected by changes made to the selected oligonucleotide to improve the delta g, corresponding free energy values, and fold structure. At block 5300, the method processes the oligonucleotides and produces a number of proposed silent mutations to improve the free energy value. At block 5302, the method displays a list, each item of the list showing the location of the proposed silent mutation, the original codon triplet, and the new codon triplet due to mutation. At block 5304, each item on the list also shows the original free energy and the free energy of the oligonucleotide affected by the proposed silent mutation. At block 5306, by clicking on various items, the method updates the presentation of the oligonucleotides to show how each item affects the oligonucleotides. The method then continues to another continuation terminal ("Terminal E5").

From Terminal E5 (FIG. 5AE), the method proceeds to decision block 5308 where a test is performed to determine whether the user is satisfied with the modifications. If the answer to the test at decision block 5308 is No, the method proceeds to Terminal E4 and jumps back to decision block 5296 where the above-identified processing steps are repeated. Otherwise, the answer to the test at decision block 5308 is Yes, and the method continues to block 5310 where it creates a record in the sequence modification table of the database noting the modifications to the nucleic acid sequence. At block 5312, the method also creates a record in the pedigree table to note the progeny of the newly-modified nucleic acid sequence. If there are mutation conflicts, the method performs conflict resolution as discussed between Terminals C14, C15. See block 5314. The method then continues to another continuation terminal ("Terminal E6").

From Terminal E6 (FIG. 5AF), the method proceeds to decision block 5316 where a test is performed to determine whether the user elects to create primers. If the answer to the test at decision block 5316 is No, the method proceeds to exit Terminal F and terminates execution. Otherwise, the answer to the test at decision block 5316 is Yes, and the method proceeds to block 5318 where the user specifies how many oligonucleotides will be pooled together to form a gene fragment. At block 5320, the method displays the number of oligonucleotides in each pool and the size of each gene fragment formed by each pool. After the user's specification, if there are extra oligonucleotides, these will be added to the remaining pools. See block 5322. At block 5324, if one or more pools have more oligonucleotides than others, the user can move them to a suitable location in the gene sequence. At block 5326, the user may specify parameters such as minimum and maximum melting temperature. The method then continues to another continuation terminal ("Terminal E7").

From Terminal E7 (FIG. 5AG), the user may specify parameters such as the minimum and maximum size of the primers to be created. See block 5328. At block 5330, the user may specify both a 5' and a 3' flanking site at the end of the primers. The user may also specify both a 5' and a 3' flanking sequence. See block 5332. At block 5334, a test is performed to determine whether the user is satisfied with the modifications. If the answer to the test at decision block 5334 is No, the method proceeds to Terminal E6 and jumps back to decision block 5316 where the above-identified processing steps are repeated. Otherwise, the answer to the test at decision block 5334 is Yes, and the method proceeds to block 5336 where the method creates a record in the sequence modification table of the database noting the modifications to the nucleic acid sequence. At block 5338, the method also creates a record in the pedigree table to note the progeny of the newly modified nucleic acid sequence. The method then continues to Terminal F and terminates execution.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method for synthesizing gene sequences, comprising:
    back translating an amino acid sequence to a nucleic acid sequence by a computer; and
    introducing stop codons into the nucleic acid sequence of alternate reading frames via silent mutations in a primary reading frame and outputting to a display coupled to the computer.

2. The method of claim 1, further comprising displaying a list, each item on the list showing a piece of information that is a particular location of a base in the nucleic acid sequence where a stop codon may be found, another piece of information that indicates whether the stop codon exists at the particular location, and a further piece of information that is a triplet coding a codon at the particular location of the base prior to a silent mutation.

3. The method of claim 1, further comprising displaying a new triplet that codes a stop codon if the stop codon does not exist at the particular location, the new triplet being a codon at the particular location of the base after silent mutation of the triplet indicated by the further piece of information.

4. The method of claim 3, further comprising producing the new triplet prior to displaying the new triplet by looking at a set of codons that is appropriate to substitute for the triplet at the particular location of a base in the nucleic acid sequence prior to silent mutation, the act of producing including obtaining the participating probability of each member of the set of codons and removing codons whose participating probability indicates rare codons.

5. The method of claim 4, wherein producing includes normalizing participating probabilities of the remaining members of the set of codons.

6. The method of claim 5, wherein producing includes selecting a member of the set of codons according to its participating probability.

7. The method of claim 6, wherein introducing includes introducing stop codons in a second and a third frame of a top strand and a first frame of a bottom strand of the nucleic acid sequence, the top strand being a strand that contains coding for the primary reading frame, the bottom strand being a complement of the top strand.

8. The method of claim 7, further comprising selecting an item from the list and introducing a stop codon at the particular location of a base in the nucleic acid sequence.

* * * * *